US010959609B1

(12) United States Patent
Swift et al.

(10) Patent No.: US 10,959,609 B1
(45) Date of Patent: Mar. 30, 2021

(54) ILLUMINATED SUCTION DEVICE

(71) Applicant: OBP Medical Corporation, Lawrence, MA (US)

(72) Inventors: Jeffrey Ralph Swift, Boca Grande, FL (US); Adrienne Clark, Waltham, MA (US); Peter L. Domenicali, Prescott Valley, AZ (US); Jason Swift, Newburyport, MA (US); Matthew Traub, Andover, MA (US)

(73) Assignee: OBP MEDICAL CORPORATION, Lawrence, MA (US)

( * ) Notice: Subject to any disclaimer, the term of this patent is extended or adjusted under 35 U.S.C. 154(b) by 0 days.

(21) Appl. No.: 16/815,556

(22) Filed: Mar. 11, 2020

Related U.S. Application Data

(60) Provisional application No. 62/968,805, filed on Jan. 31, 2020.

(51) Int. Cl.
*A61B 1/06* (2006.01)
*A61M 1/00* (2006.01)

(52) U.S. Cl.
CPC .............. *A61B 1/06* (2013.01); *A61B 1/0684* (2013.01); *A61M 1/0031* (2013.01); *A61M 1/0039* (2013.01); *A61M 1/0088* (2013.01); *A61M 2205/587* (2013.01); *A61M 2205/6063* (2013.01); *A61M 2205/8206* (2013.01)

(58) Field of Classification Search
CPC ................................ A61B 1/06; A61B 1/0684
See application file for complete search history.

(56) References Cited

U.S. PATENT DOCUMENTS

| 559,122 A | 4/1896 | Daily |
| 659,182 A | 10/1900 | Pilling |
| 2,235,979 A | 3/1941 | Brown |
| 2,247,458 A | 6/1941 | Shepard |
| 2,482,971 A | 9/1949 | Golson |
| 2,592,190 A | 4/1952 | Rubens et al. |
| 3,324,850 A | 6/1967 | Gunning et al. |
| 3,332,414 A | 7/1967 | Gasper |
| 3,532,088 A | 10/1970 | Fiore |
| 3,592,199 A | 7/1971 | Ostensen |
| 3,595,222 A | 7/1971 | Vellacott |

(Continued)

FOREIGN PATENT DOCUMENTS

| CN | 2239235 Y | 11/1996 |
| CN | 2265156 Y | 10/1997 |

(Continued)

OTHER PUBLICATIONS

International Search Report for International application No. PCT/US2016/016154 dated May 19, 2016 for corresponding U.S. Appl. No. 14/614,413, which is enclosed.

(Continued)

*Primary Examiner* — Nicholas W Woodall
(74) *Attorney, Agent, or Firm* — Cowan, Liebowitz & Latman, P.C.; Anastasia Zhadina

(57) ABSTRACT

An illuminated medical device comprising an outer housing, and an illumination assembly comprising at least one direct light source oriented to emit light radially away from a central axis of the medical device and at least one reflector configured to reflect light from the at least one direct light source toward a target area external to the outer housing.

30 Claims, 71 Drawing Sheets

(56) References Cited

U.S. PATENT DOCUMENTS

| | | |
|---|---|---|
| 3,638,644 A | 2/1972 | Reick |
| 3,675,641 A | 7/1972 | Fiore |
| 3,716,047 A | 2/1973 | Moore et al. |
| 3,729,006 A | 4/1973 | Wilder et al. |
| 3,762,400 A | 10/1973 | McDonald |
| 3,769,968 A | 11/1973 | Blount et al. |
| 3,789,835 A | 2/1974 | Whitman |
| 3,815,585 A | 6/1974 | Fiore |
| 3,826,248 A | 7/1974 | Gobels |
| 3,851,642 A | 12/1974 | McDonald |
| 3,934,578 A | 1/1976 | Heine |
| 3,945,371 A | 3/1976 | Adelman |
| 3,978,850 A | 9/1976 | Moore et al. |
| 4,067,323 A | 1/1978 | Troutner |
| 4,156,424 A | 5/1979 | Burgin |
| 4,210,133 A | 7/1980 | Castaneda |
| 4,226,228 A | 10/1980 | Shin et al. |
| 4,263,899 A | 4/1981 | Burgin |
| 4,300,541 A | 11/1981 | Burgin |
| 4,337,763 A | 7/1982 | Petrassevich |
| 4,432,351 A | 2/1984 | Hoary |
| 4,492,220 A | 1/1985 | Hayes |
| 4,502,468 A | 3/1985 | Burgin |
| 4,527,553 A | 7/1985 | Upsher |
| 4,546,761 A | 10/1985 | McCullough |
| 4,551,129 A * | 11/1985 | Coleman ............ A61B 3/0008 600/249 |
| 4,562,832 A | 1/1986 | Wilder |
| 4,566,439 A | 1/1986 | Burgin |
| 4,574,784 A | 3/1986 | Soloway |
| 4,597,383 A | 7/1986 | Van Der Bel |
| 4,607,623 A | 8/1986 | Bauman |
| 4,619,248 A | 10/1986 | Walsh |
| 4,638,792 A | 1/1987 | Burgin |
| 4,766,887 A | 8/1988 | Cecil, Jr. et al. |
| 4,807,600 A | 2/1989 | Hayes |
| 4,884,559 A | 12/1989 | Collins |
| 4,905,670 A | 3/1990 | Adair |
| 4,934,352 A | 6/1990 | Sullivan, Jr. |
| 4,971,036 A | 11/1990 | Collins |
| 5,018,507 A | 5/1991 | Montaldi |
| 5,026,368 A | 6/1991 | Adair |
| 5,054,906 A | 10/1991 | Lyons, Jr. |
| 5,063,908 A | 11/1991 | Collins |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,179,938 A | 1/1993 | Lonky |
| 5,222,271 A | 6/1993 | Eganhouse |
| D337,384 S | 7/1993 | Schucman |
| 5,318,009 A | 6/1994 | Robinson |
| 5,329,938 A | 7/1994 | Lonky |
| 5,427,152 A | 6/1995 | Weber |
| 5,438,976 A | 8/1995 | Nash |
| 5,465,709 A | 11/1995 | Dickie et al. |
| 5,499,964 A | 3/1996 | Beck et al. |
| 5,512,038 A | 4/1996 | O'Neal et al. |
| 5,553,627 A | 9/1996 | Newkirk |
| 5,588,952 A * | 12/1996 | Dandolu ............ A61M 1/008 362/572 |
| 5,695,492 A | 12/1997 | Brown |
| 5,716,329 A | 2/1998 | Dieter |
| 5,785,648 A | 7/1998 | Min |
| 5,840,013 A | 11/1998 | Lee et al. |
| 5,846,249 A | 12/1998 | Thompson |
| 5,865,729 A | 2/1999 | Meehan |
| 5,873,820 A | 2/1999 | Norell |
| 5,879,304 A | 3/1999 | Schuchman et al. |
| 5,888,195 A | 3/1999 | Schneider |
| 5,899,854 A | 5/1999 | Slishman |
| 5,916,150 A | 6/1999 | Sillman |
| 5,967,971 A | 10/1999 | Bolser |
| 6,001,077 A | 12/1999 | Ellman et al. |
| 6,004,265 A | 12/1999 | Hsu et al. |
| 6,036,638 A | 3/2000 | Nwawka |
| 6,036,713 A | 3/2000 | Kieturakis |
| 6,048,308 A | 4/2000 | Strong |
| 6,080,105 A | 6/2000 | Spears |
| 6,130,520 A | 10/2000 | Wawro et al. |
| 6,176,824 B1 | 1/2001 | Davis |
| 6,186,944 B1 | 2/2001 | Tsai |
| 6,217,512 B1 | 4/2001 | Salo et al. |
| 6,231,505 B1 | 5/2001 | Martin |
| 6,231,506 B1 | 5/2001 | Hu et al. |
| 6,254,247 B1 | 7/2001 | Carson |
| 6,277,067 B1 | 8/2001 | Blair |
| 6,319,199 B1 | 11/2001 | Sheehan et al. |
| 6,346,085 B1 | 2/2002 | Schiffman |
| 6,359,644 B1 | 3/2002 | Salvati |
| 6,361,489 B1 | 3/2002 | Tsai |
| 6,379,296 B1 | 4/2002 | Baggett |
| 6,379,299 B1 | 4/2002 | Borodulin et al. |
| 6,394,111 B1 | 5/2002 | Jacobs et al. |
| 6,394,950 B1 | 5/2002 | Weiss |
| 6,413,208 B1 | 7/2002 | Schollhorn et al. |
| 6,416,465 B2 | 7/2002 | Brau |
| 6,428,180 B1 | 8/2002 | Karram et al. |
| 6,432,045 B2 | 8/2002 | Lemperle et al. |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller et al. |
| 6,487,440 B2 | 11/2002 | Deckert et al. |
| 6,504,985 B2 | 1/2003 | Parker et al. |
| 6,523,973 B2 | 2/2003 | Galli |
| 6,524,259 B2 | 2/2003 | Baxter-Jones et al. |
| 6,569,091 B2 | 5/2003 | Diokno et al. |
| 6,589,168 B2 | 7/2003 | Thompson |
| 6,595,917 B2 | 7/2003 | Nieto |
| 6,616,603 B1 | 9/2003 | Fontana |
| 6,626,825 B2 | 9/2003 | Tsai |
| 6,663,576 B2 | 12/2003 | Gombrich et al. |
| 6,676,598 B2 | 1/2004 | Rudischhauser et al. |
| 6,719,688 B2 | 4/2004 | Pecherer et al. |
| 6,761,687 B1 | 7/2004 | Doshi |
| 6,830,547 B2 | 12/2004 | Weiss |
| 6,896,653 B2 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,223,223 B2 | 5/2007 | Lindsay |
| 7,276,025 B2 | 10/2007 | Roberts et al. |
| 7,306,559 B2 | 12/2007 | Williams |
| 7,492,116 B2 | 2/2009 | Oleynikov et al. |
| 7,631,981 B2 | 12/2009 | Miller et al. |
| 7,736,304 B2 | 6/2010 | Pecherer |
| 7,758,203 B2 | 7/2010 | McMahon et al. |
| 7,878,973 B2 | 2/2011 | Yee et al. |
| 7,909,759 B2 | 3/2011 | Pecherer |
| 7,967,809 B2 | 6/2011 | Jay-Robinson |
| 8,012,089 B2 | 9/2011 | Bayat |
| 8,047,987 B2 | 11/2011 | Grey et al. |
| 8,052,702 B2 | 11/2011 | Hess et al. |
| 8,088,066 B2 | 1/2012 | Grey et al. |
| 8,096,945 B2 | 1/2012 | Buchok et al. |
| 8,142,352 B2 | 3/2012 | Vivenzio et al. |
| 8,142,353 B2 | 3/2012 | Pecherer et al. |
| 8,157,728 B2 | 4/2012 | Danna et al. |
| 8,162,826 B2 | 4/2012 | Pecherer et al. |
| 8,251,898 B2 | 8/2012 | Pecherer |
| 8,292,805 B2 | 10/2012 | Vayser et al. |
| 8,317,693 B2 | 11/2012 | Grey et al. |
| 8,388,523 B2 | 3/2013 | Vivenzio et al. |
| 8,394,017 B2 | 3/2013 | Kieffer |
| 8,435,175 B2 | 5/2013 | McMahon et al. |
| 8,512,234 B2 | 8/2013 | Grey et al. |
| 8,512,237 B2 | 8/2013 | Bastia |
| 8,555,892 B2 | 10/2013 | Traub |
| 8,596,847 B2 | 12/2013 | Vayser et al. |
| 8,628,879 B2 | 1/2014 | Pecherer et al. |
| 8,651,704 B1 * | 2/2014 | Gordin ............ F21V 33/0092 362/294 |

(56) References Cited

U.S. PATENT DOCUMENTS

| | | |
|---|---|---|
| 8,795,162 B2 | 8/2014 | Vayser et al. |
| 8,821,385 B2 | 9/2014 | Naito |
| 8,870,761 B2 | 10/2014 | Vayser et al. |
| D719,652 S | 12/2014 | Swift |
| 8,979,745 B2 | 3/2015 | Swift |
| 9,044,161 B2 | 6/2015 | Vayser et al. |
| 9,050,048 B2 | 6/2015 | Nadershahi |
| 9,072,452 B2 | 7/2015 | Vayser et al. |
| D745,669 S | 12/2015 | Swift |
| 9,241,617 B2 | 1/2016 | Grey et al. |
| D752,217 S | 3/2016 | Swift |
| 9,271,709 B2 | 3/2016 | Grey et al. |
| 9,271,710 B2 | 3/2016 | Grey et al. |
| 9,282,878 B2 | 3/2016 | Grey et al. |
| D753,295 S | 4/2016 | Vivenzio et al. |
| 9,307,897 B2 | 4/2016 | Swift |
| 9,308,054 B2 | 4/2016 | Vayser et al. |
| 9,332,898 B2 | 5/2016 | McMahon et al. |
| 9,468,366 B2 | 10/2016 | Grey et al. |
| 9,510,737 B2 | 12/2016 | Vayser et al. |
| 9,532,706 B2 | 1/2017 | McMahon et al. |
| 9,629,529 B1 | 4/2017 | Indovina et al. |
| 9,636,182 B2 | 5/2017 | Vayser et al. |
| 9,718,130 B1 | 8/2017 | Vayser et al. |
| 9,763,743 B2 | 9/2017 | Lin et al. |
| 9,808,231 B2 | 11/2017 | Miraki et al. |
| 9,814,377 B2 | 11/2017 | Lia et al. |
| 9,820,638 B2 | 11/2017 | Cheng |
| 9,820,729 B2 | 11/2017 | Miles et al. |
| 9,826,892 B2 | 11/2017 | Dresher et al. |
| 9,833,295 B2 | 12/2017 | Vayser et al. |
| 9,833,308 B2 | 12/2017 | Dye |
| 9,844,364 B2 | 12/2017 | Grey et al. |
| 9,861,349 B2 | 1/2018 | Nadershahi et al. |
| 9,867,531 B2 | 1/2018 | Pacey et al. |
| 9,877,639 B2 | 1/2018 | Grey et al. |
| 9,877,644 B2 | 1/2018 | Greenstein et al. |
| D809,660 S | 2/2018 | Nguyen et al. |
| 9,883,792 B2 | 2/2018 | McMahon et al. |
| 9,888,957 B2 | 2/2018 | Wolf et al. |
| 9,907,544 B2 | 3/2018 | Nadershahi et al. |
| 9,913,682 B2 | 3/2018 | Wolf et al. |
| 9,918,618 B2 | 3/2018 | Molnar |
| 9,918,802 B2 | 3/2018 | Coppersmith et al. |
| 9,931,028 B2 | 4/2018 | Lia et al. |
| 9,943,295 B2 | 4/2018 | King |
| 9,949,814 B2 | 4/2018 | Alexander et al. |
| 9,955,858 B2 | 5/2018 | Pamnani et al. |
| 9,968,262 B2 | 5/2018 | Greenstein et al. |
| 9,968,346 B2 | 5/2018 | Alexander et al. |
| 9,980,710 B2 | 5/2018 | Seifert et al. |
| 9,986,901 B2 | 6/2018 | Grey et al. |
| 9,986,903 B2 | 6/2018 | Nadershahi et al. |
| 9,986,988 B2 | 6/2018 | Ferro et al. |
| 9,999,345 B2 | 6/2018 | Vayser et al. |
| 10,004,392 B2 | 6/2018 | Millard et al. |
| 10,004,393 B2 | 6/2018 | Kucklick |
| 10,028,648 B2 | 7/2018 | Goldfain et al. |
| 10,028,649 B2 | 7/2018 | Salvati et al. |
| 10,028,780 B2 | 7/2018 | Wolf et al. |
| 10,045,686 B2 | 8/2018 | Ou Yang et al. |
| 10,045,731 B2 | 8/2018 | Prasad et al. |
| 10,052,432 B2 | 8/2018 | Dexter et al. |
| 10,064,611 B2 | 9/2018 | Ross et al. |
| 10,064,613 B2 | 9/2018 | Davis et al. |
| 10,068,173 B2 | 9/2018 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 10,166,016 B2 | 1/2019 | Shimizu et al. |
| 10,172,601 B2 | 1/2019 | Ahn |
| 10,174,933 B2 | 1/2019 | Phillips, Jr. et al. |
| 10,188,298 B2 | 1/2019 | Greenstein et al. |
| 10,213,271 B2 | 2/2019 | Duggal et al. |
| 10,219,800 B2 | 3/2019 | Tsubouchi |
| 10,220,445 B2 | 3/2019 | Vayser et al. |
| 10,226,555 B2 | 3/2019 | Vayser et al. |
| 10,238,462 B2 | 3/2019 | Wood et al. |
| D846,119 S | 4/2019 | Greeley et al. |
| 10,278,571 B2 | 5/2019 | Poormand |
| 10,292,782 B2 | 5/2019 | Haverich et al. |
| 10,292,784 B2 | 5/2019 | Duggal et al. |
| 10,342,525 B2 | 7/2019 | Wilson |
| 2001/0029044 A1 | 10/2001 | Gombrich et al. |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0115909 A1 | 8/2002 | Bolser |
| 2002/0156350 A1 | 10/2002 | Nieto |
| 2002/0165435 A1 | 11/2002 | Weiss |
| 2002/0198471 A1 | 12/2002 | Baxter-Jones et al. |
| 2003/0095781 A1 | 5/2003 | Williams |
| 2003/0105387 A1 | 6/2003 | Frumovitz et al. |
| 2003/0139673 A1 | 7/2003 | Vivenzio et al. |
| 2003/0158502 A1 | 8/2003 | Baxter-Jones et al. |
| 2003/0176772 A1 | 9/2003 | Yang |
| 2003/0187331 A1 | 10/2003 | Faludi et al. |
| 2004/0004846 A1* | 1/2004 | Steen ............... A61B 3/0008 362/555 |
| 2004/0026829 A1 | 2/2004 | Van Der Weegen |
| 2004/0054260 A1 | 3/2004 | Klaassen et al. |
| 2004/0141175 A1 | 7/2004 | Baldwin et al. |
| 2004/0183482 A1 | 9/2004 | Roberts et al. |
| 2004/0184288 A1 | 9/2004 | Bettis |
| 2004/0186355 A1 | 9/2004 | Strong |
| 2005/0065496 A1 | 3/2005 | Simon et al. |
| 2005/0085699 A1 | 4/2005 | Weiss |
| 2005/0085723 A1 | 4/2005 | Huebner |
| 2005/0093718 A1* | 5/2005 | Martin ............... H05B 45/00 340/981 |
| 2005/0125015 A1 | 6/2005 | McNally-Heintzelman et al. |
| 2005/0159649 A1 | 7/2005 | Patel |
| 2005/0192482 A1 | 9/2005 | Carpenter |
| 2005/0215858 A1 | 9/2005 | Vail, III |
| 2005/0240081 A1 | 10/2005 | Eliachar |
| 2005/0277811 A1 | 12/2005 | Richards et al. |
| 2006/0084843 A1 | 4/2006 | Sommerich et al. |
| 2006/0155276 A1 | 7/2006 | Walulik et al. |
| 2006/0189847 A1 | 8/2006 | Yee et al. |
| 2006/0200186 A1 | 9/2006 | Marchek et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0066872 A1 | 3/2007 | Morrison et al. |
| 2007/0100212 A1 | 5/2007 | Pimenta et al. |
| 2007/0208226 A1 | 9/2007 | Grey et al. |
| 2007/0230164 A1 | 10/2007 | Vivenzio et al. |
| 2007/0230167 A1 | 10/2007 | McMahon et al. |
| 2007/0255110 A1 | 11/2007 | Wax et al. |
| 2007/0270866 A1 | 11/2007 | Von Jako |
| 2007/0287888 A1 | 12/2007 | Lovell et al. |
| 2008/0002426 A1 | 1/2008 | Vayser et al. |
| 2008/0113312 A1 | 5/2008 | Ortega |
| 2008/0221569 A1 | 9/2008 | Moore et al. |
| 2008/0228038 A1 | 9/2008 | McMahon et al. |
| 2008/0269564 A1 | 10/2008 | Gelnett |
| 2008/0269565 A1 | 10/2008 | McMahon et al. |
| 2008/0278936 A1 | 11/2008 | Kurth et al. |
| 2009/0018400 A1 | 1/2009 | Raymond et al. |
| 2009/0069634 A1 | 3/2009 | Larkin |
| 2009/0097236 A1 | 4/2009 | Miller et al. |
| 2009/0112068 A1 | 4/2009 | Grey et al. |
| 2009/0275803 A1 | 11/2009 | Krauter et al. |
| 2009/0287192 A1 | 11/2009 | Vivenzio et al. |
| 2009/0312610 A1 | 12/2009 | Buchok et al. |
| 2010/0036382 A1 | 2/2010 | Bonnadier |
| 2010/0041955 A1 | 2/2010 | Grey et al. |
| 2010/0097794 A1* | 4/2010 | Teng ............... F21V 9/67 362/231 |

(56) References Cited

U.S. PATENT DOCUMENTS

| | | | |
|---|---|---|---|
| 2010/0190129 A1* | 7/2010 | Paz | A61C 1/088 433/29 |
| 2010/0191062 A1 | 7/2010 | Kieffer | |
| 2010/0292533 A1 | 11/2010 | Kasahara et al. | |
| 2011/0193484 A1* | 8/2011 | Harbers | F21V 7/06 315/129 |
| 2011/0275894 A1 | 11/2011 | Mackin | |
| 2012/0055470 A1 | 3/2012 | Pecherer et al. | |
| 2012/0059226 A1 | 3/2012 | Funt | |
| 2012/0078060 A1 | 3/2012 | Swift | |
| 2012/0116170 A1 | 5/2012 | Vayser et al. | |
| 2012/0232352 A1 | 9/2012 | Lin et al. | |
| 2013/0018230 A1 | 1/2013 | Su et al. | |
| 2013/0021798 A1 | 1/2013 | Chen et al. | |
| 2013/0041229 A2 | 2/2013 | Hahn et al. | |
| 2013/0092421 A1 | 4/2013 | Kajiya | |
| 2013/0102850 A1 | 4/2013 | Fiorella | |
| 2013/0102887 A1 | 4/2013 | Thompson et al. | |
| 2013/0109910 A1 | 5/2013 | Alexander et al. | |
| 2013/0158345 A1 | 6/2013 | Majlessi | |
| 2013/0197313 A1 | 8/2013 | Wan | |
| 2013/0245657 A1 | 9/2013 | Deville et al. | |
| 2013/0267786 A1 | 10/2013 | Vayser et al. | |
| 2013/0281784 A1 | 10/2013 | Ray | |
| 2013/0324801 A1 | 12/2013 | Grey et al. | |
| 2014/0088371 A1 | 3/2014 | Vayser et al. | |
| 2014/0179998 A1 | 6/2014 | Pacey | |
| 2014/0202459 A1 | 7/2014 | Iqbal | |
| 2014/0228875 A1 | 8/2014 | Saadat | |
| 2014/0257039 A1 | 9/2014 | Feldman | |
| 2014/0275790 A1 | 9/2014 | Vivenzio et al. | |
| 2014/0309499 A1 | 10/2014 | Swift | |
| 2014/0316211 A1 | 10/2014 | Hermle | |
| 2014/0323800 A1 | 10/2014 | Dye | |
| 2014/0364695 A1 | 12/2014 | Nadershahi et al. | |
| 2014/0371536 A1 | 12/2014 | Miller et al. | |
| 2015/0018625 A1 | 1/2015 | Miraki et al. | |
| 2015/0157469 A1 | 6/2015 | Prado et al. | |
| 2015/0238070 A1 | 8/2015 | Lia et al. | |
| 2015/0285382 A1 | 10/2015 | Kienreich et al. | |
| 2015/0297217 A1 | 10/2015 | Huitema et al. | |
| 2016/0000305 A1 | 1/2016 | Elbaz et al. | |
| 2016/0030128 A1 | 2/2016 | Duggal et al. | |
| 2016/0038032 A1 | 2/2016 | Dan | |
| 2016/0066915 A1 | 3/2016 | Baber et al. | |
| 2016/0081833 A1 | 3/2016 | Leblanc et al. | |
| 2016/0095506 A1 | 4/2016 | Dan et al. | |
| 2016/0100751 A1 | 4/2016 | Davis et al. | |
| 2016/0151058 A1 | 6/2016 | Ferro et al. | |
| 2016/0302657 A1 | 10/2016 | Hussey et al. | |
| 2017/0007228 A1 | 1/2017 | Costabile | |
| 2017/0020621 A1 | 1/2017 | Huldin et al. | |
| 2017/0059400 A1* | 3/2017 | Murphy | F21V 17/107 |
| 2017/0065282 A1 | 3/2017 | Mathis et al. | |
| 2017/0079518 A1 | 3/2017 | Elbaz et al. | |
| 2017/0172404 A1 | 6/2017 | McMahon et al. | |
| 2017/0172555 A1 | 6/2017 | Shimizu et al. | |
| 2017/0181605 A1 | 6/2017 | Lalli et al. | |
| 2017/0181607 A1 | 6/2017 | Lalli et al. | |
| 2017/0181615 A1 | 6/2017 | Vella et al. | |
| 2017/0181616 A1 | 6/2017 | Vella et al. | |
| 2017/0224206 A1 | 8/2017 | Vayser | |
| 2017/0231712 A1 | 8/2017 | Vayser | |
| 2017/0300623 A1 | 10/2017 | Rosenblatt et al. | |
| 2017/0303903 A1 | 10/2017 | De Koning et al. | |
| 2017/0347871 A1 | 12/2017 | Wallace et al. | |
| 2017/0360423 A1 | 12/2017 | Stevenson et al. | |
| 2018/0000469 A1 | 1/2018 | Wood et al. | |
| 2018/0008137 A1 | 1/2018 | Poormand | |
| 2018/0008138 A1 | 1/2018 | Thommen et al. | |
| 2018/0008368 A1 | 1/2018 | Duggal et al. | |
| 2018/0014721 A1 | 1/2018 | Rullo et al. | |
| 2018/0014842 A1 | 1/2018 | Shener-Irmakoglu | |
| 2018/0014900 A1 | 1/2018 | Vayser et al. | |
| 2018/0036095 A1 | 2/2018 | Vayser et al. | |
| 2018/0042596 A1 | 2/2018 | Tsubouchi | |
| 2018/0064316 A1 | 3/2018 | Charles et al. | |
| 2018/0064317 A1 | 3/2018 | Tesar | |
| 2018/0078301 A1 | 3/2018 | Vayser | |
| 2018/0116581 A1 | 5/2018 | Prasad et al. | |
| 2018/0125336 A1 | 5/2018 | Goldfarb et al. | |
| 2018/0125347 A1 | 5/2018 | Czyzewski et al. | |
| 2018/0132710 A1 | 5/2018 | Pacey et al. | |
| 2018/0132970 A1 | 5/2018 | Ritter | |
| 2018/0153391 A1 | 6/2018 | McMahon et al. | |
| 2018/0156448 A1 | 6/2018 | Phillips, Jr. et al. | |
| 2018/0206832 A1 | 7/2018 | Greeley et al. | |
| 2018/0228376 A1 | 8/2018 | Greenstein et al. | |
| 2018/0228483 A1 | 8/2018 | Duggal et al. | |
| 2018/0235444 A1 | 8/2018 | Tsai | |
| 2018/0235592 A1 | 8/2018 | Kass et al. | |
| 2018/0249902 A1 | 9/2018 | Grey et al. | |
| 2018/0263480 A1 | 9/2018 | Lalli et al. | |
| 2018/0271581 A1 | 9/2018 | Ou Yang et al. | |
| 2018/0280011 A1 | 10/2018 | Ferro et al. | |
| 2018/0296082 A1 | 10/2018 | Salvati et al. | |
| 2018/0317746 A1 | 11/2018 | Lalli et al. | |
| 2018/0317752 A1 | 11/2018 | Cybulski et al. | |
| 2018/0317902 A1 | 11/2018 | Green et al. | |
| 2018/0328572 A1 | 11/2018 | Kennedy et al. | |
| 2019/0038273 A1 | 2/2019 | Perler et al. | |
| 2019/0049655 A1 | 2/2019 | Zagatsky et al. | |
| 2019/0076138 A1 | 3/2019 | Opperman | |
| 2019/0083079 A1 | 3/2019 | Shimizu et al. | |
| 2019/0133432 A1 | 5/2019 | Tsai | |
| 2019/0143006 A1 | 5/2019 | Vayser et al. | |
| 2019/0143414 A1 | 5/2019 | Vayser et al. | |
| 2019/0150422 A1 | 5/2019 | Welch | |
| 2019/0150725 A1 | 5/2019 | Ramanujam et al. | |
| 2019/0150739 A1 | 5/2019 | Wawro et al. | |
| 2019/0150786 A1 | 5/2019 | Vassallo et al. | |
| 2019/0167111 A1 | 6/2019 | Greenstein et al. | |
| 2019/0167378 A1 | 6/2019 | Wood et al. | |
| 2019/0190293 A1 | 6/2019 | Wawro et al. | |
| 2019/0223708 A1 | 7/2019 | Recanati et al. | |
| 2019/0254512 A1 | 8/2019 | Spiertz | |
| 2019/0335988 A1 | 11/2019 | Lia et al. | |
| 2019/0343379 A1 | 11/2019 | Altamura | |
| 2019/0365217 A1 | 12/2019 | Hegenberger | |
| 2020/0008694 A1 | 1/2020 | Karla et al. | |
| 2020/0046216 A1 | 2/2020 | Moein | |
| 2020/0069171 A1 | 3/2020 | Miller et al. | |
| 2020/0107714 A1 | 4/2020 | Bar-Or et al. | |
| 2020/0253467 A1 | 8/2020 | Lees, Jr. et al. | |
| 2020/0337541 A1 | 10/2020 | Vivenzio et al. | |

FOREIGN PATENT DOCUMENTS

| | | |
|---|---|---|
| CN | 2516109 Y | 10/2002 |
| CN | 2629738 Y | 8/2004 |
| CN | 1565664 A | 1/2005 |
| CN | 2668152 Y | 1/2005 |
| CN | 1717195 A | 1/2006 |
| CN | 101179982 A | 5/2008 |
| CN | 201055387 Y | 5/2008 |
| CN | 203591245 U | 5/2008 |
| CN | 102415869 A | 4/2012 |
| CN | 302536685 S | 8/2013 |
| CN | 103925266 A | 7/2014 |
| CN | 203898367 U | 10/2014 |
| CN | 102573700 B | 12/2014 |
| DE | 2128855 A | 12/1972 |
| DE | 202004002963 U1 | 5/2004 |
| DE | 202005019780 U1 | 5/2006 |
| DE | 600 33 612 T2 | 12/2007 |
| DE | 202010017638 U | 5/2012 |
| EP | 0190014 A2 | 8/1986 |
| EP | 1074224 A2 | 7/2001 |
| FR | 2490478 A1 | 3/1982 |
| GB | 2505463 A | 5/2014 |
| RU | 2187972 C2 | 8/2002 |
| RU | 2308873 C2 | 10/2007 |
| WO | 9825512 A1 | 6/1998 |
| WO | 0137739 A1 | 5/2001 |

(56) References Cited

FOREIGN PATENT DOCUMENTS

| WO | 01/62137 A2 | 8/2001 |
|---|---|---|
| WO | 03082123 A2 | 10/2003 |
| WO | 2004064624 A1 | 8/2004 |
| WO | 2006107877 A2 | 10/2006 |
| WO | 2006107878 A2 | 10/2006 |
| WO | 2009137017 A2 | 11/2009 |
| WO | 2013-044151 A1 | 3/2013 |
| WO | 2014-041172 A1 | 3/2014 |
| WO | 2006121530 A2 | 11/2016 |
| WO | 2016196788 A1 | 12/2016 |

OTHER PUBLICATIONS

International Search Report, for International application No. PCT/US2016/035508 dated Sep. 15, 2016 for corresponding U.S. Appl. No. 15/171,581, which is enclosed.
International Search Report for International application No. PCT/US2016/036833 dated Jan. 19, 2017.
Office Action issued in U.S. Appl. No. 15/171,581, which is enclosed.
PCT Search Report issued in PCT Application No. PCT/US2017/042617, which is enclosed.
Nov. 1, 2017 Chinese Office Action, which is enclosed without an English Translation, that issued in Chinese Patent Application No. 201510543086.7.
Jul. 16, 2018 Chinese Office Action, which is enclosed without an English Translation, that issued in Chinese Patent Application No. 201510543086.7.
Solvey, Techinical Data Sheet, Ixef 1022 polyarylamide, Feb. 13, 2015, pp. 1-5.
http://www.makeitfrom.com/material-properties/Polyetheretheketone-PEEK, printed on Oct. 9, 2016, pp. 1-9.
The above documents were cited in a European Search Report dated Nov. 23, 2018, which is enclosed, that issued in the corresponding European Patent Application No. 16747107.7.
The above patent was cited in a Oct. 29, 2018 Chinese Office Action, which is enclosed without an English Translation, that issued in Chinese Patent Application No. 201711159829.6.
International Search Report of PCT/US2018/054925, dated Oct. 9, 2018, which is enclosed.
Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.
Supplementary European Search Report dated Apr. 24, 2019, which is enclosed, that issued in European Patent Application No. 16804432.9.
OBP Medical—OfficeSPEC, Premier Speculum for In-Office Procedures published Nov. 30, 2009 (1 page).
OBP Medical—ER-SPEC Obgyn Brochure published Nov. 19, 2014 (2 pages).
OBP Medical—ER-SPEC Brochure, Light Source Now 10x Brighter published Oct. 30, 2012 (1 page).
OBP Medical—ER-SPEC Product Presentation published Apr. 16, 2014 (12 pages).
OBP Medical—ER-SPEC Brochure published Apr. 11, 2013 (2 pages).
OBP Medical—ER-SPEC Brochure published Feb. 4, 2013 (2 pages).
OBP Medical—ER-SPEC Brochure, Light Source Now 10x Brighter published Jan. 23, 2013 (1 page).
Redefining illumination, Eikon LT Adapt SE for optimal precision and protection (2019), Stryker, www.stryker.com/surgical (3 pages).

* cited by examiner

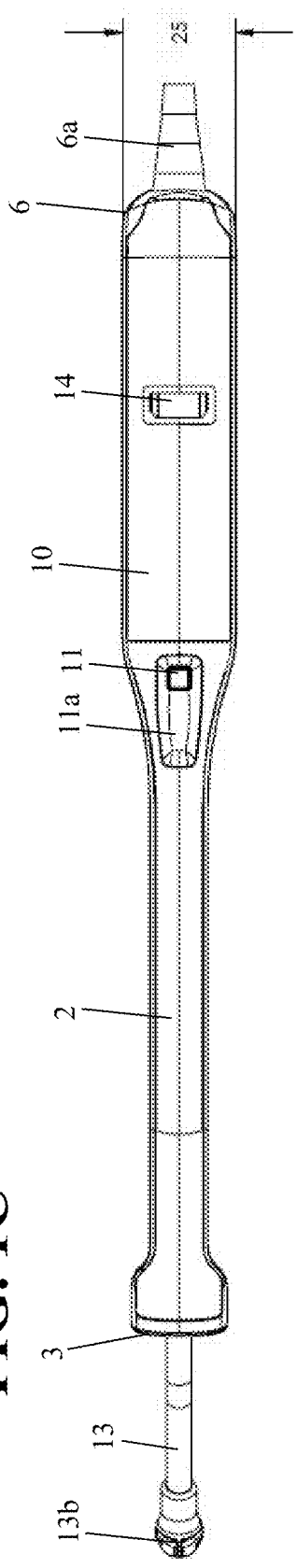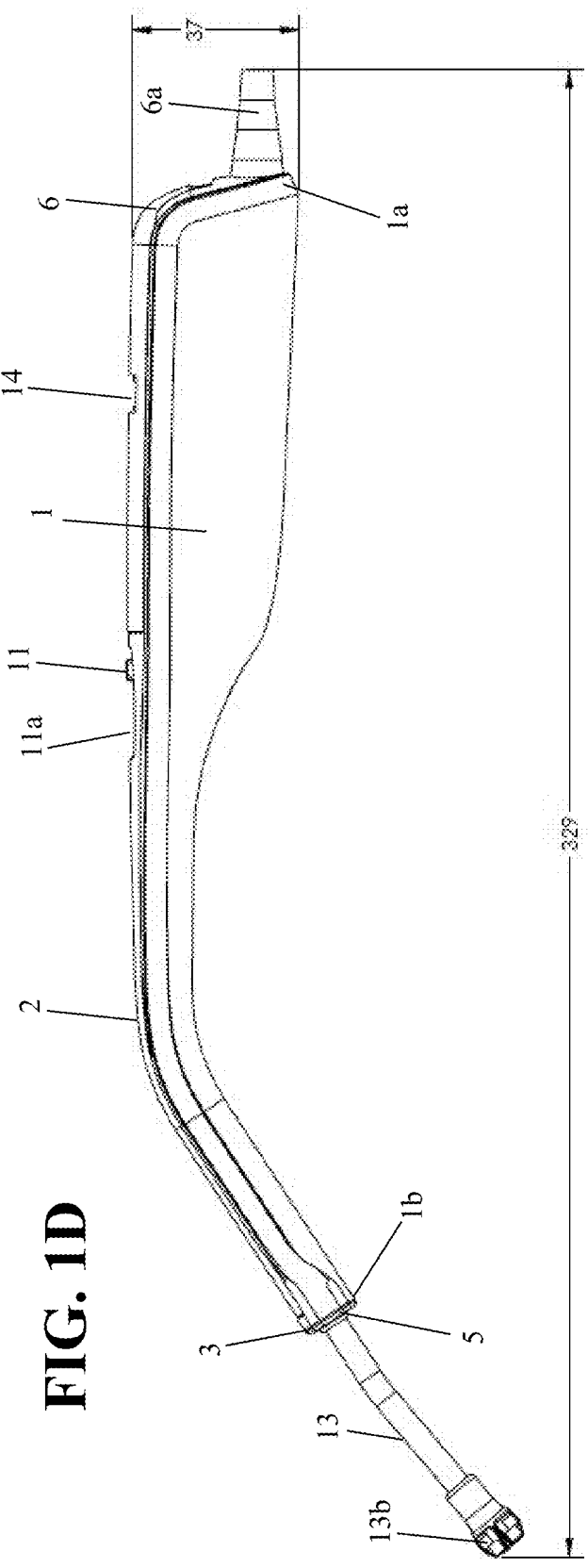

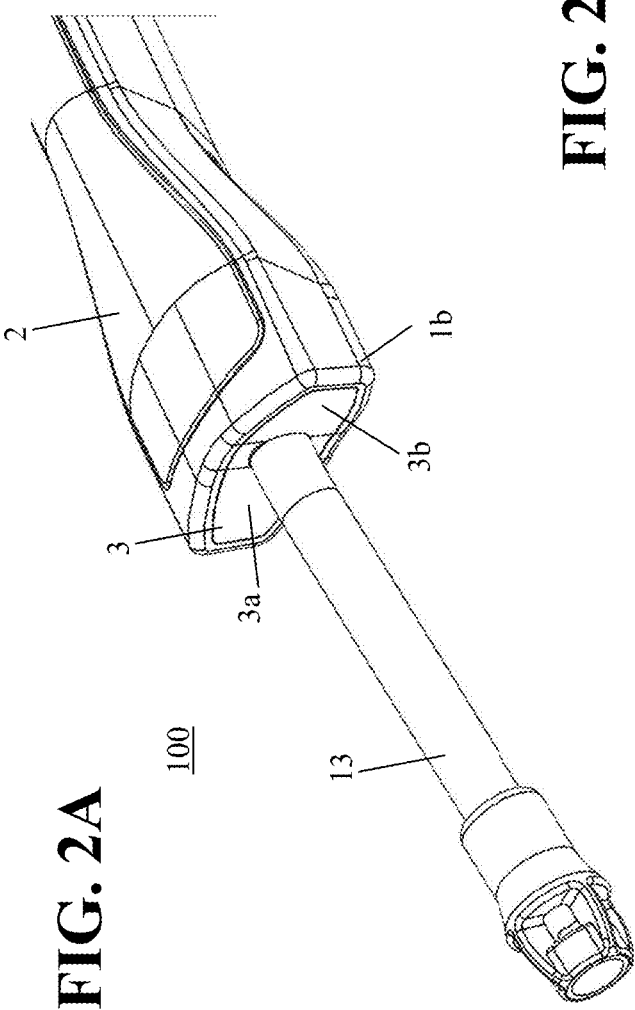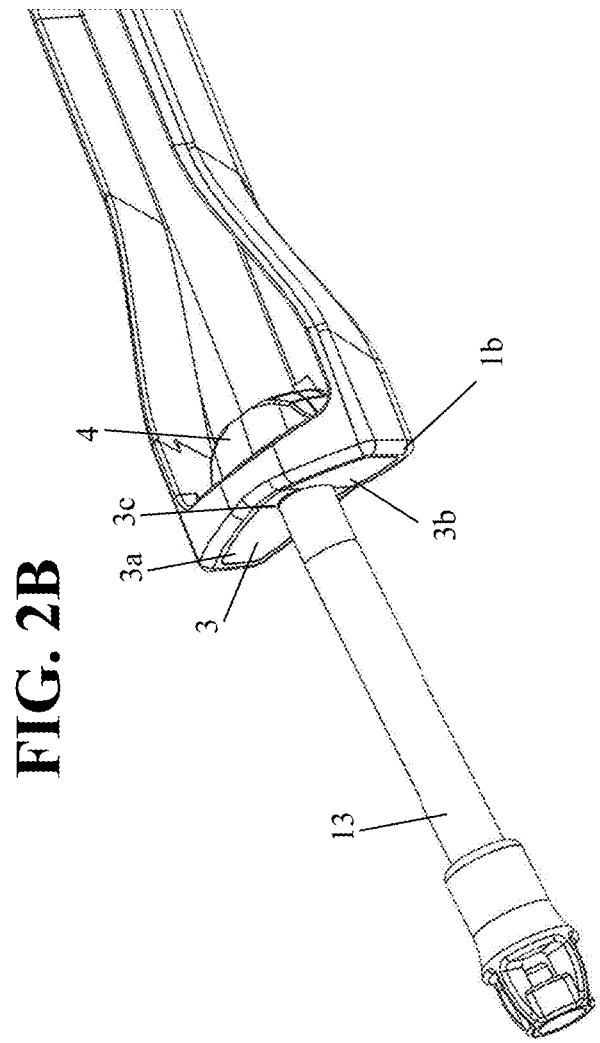

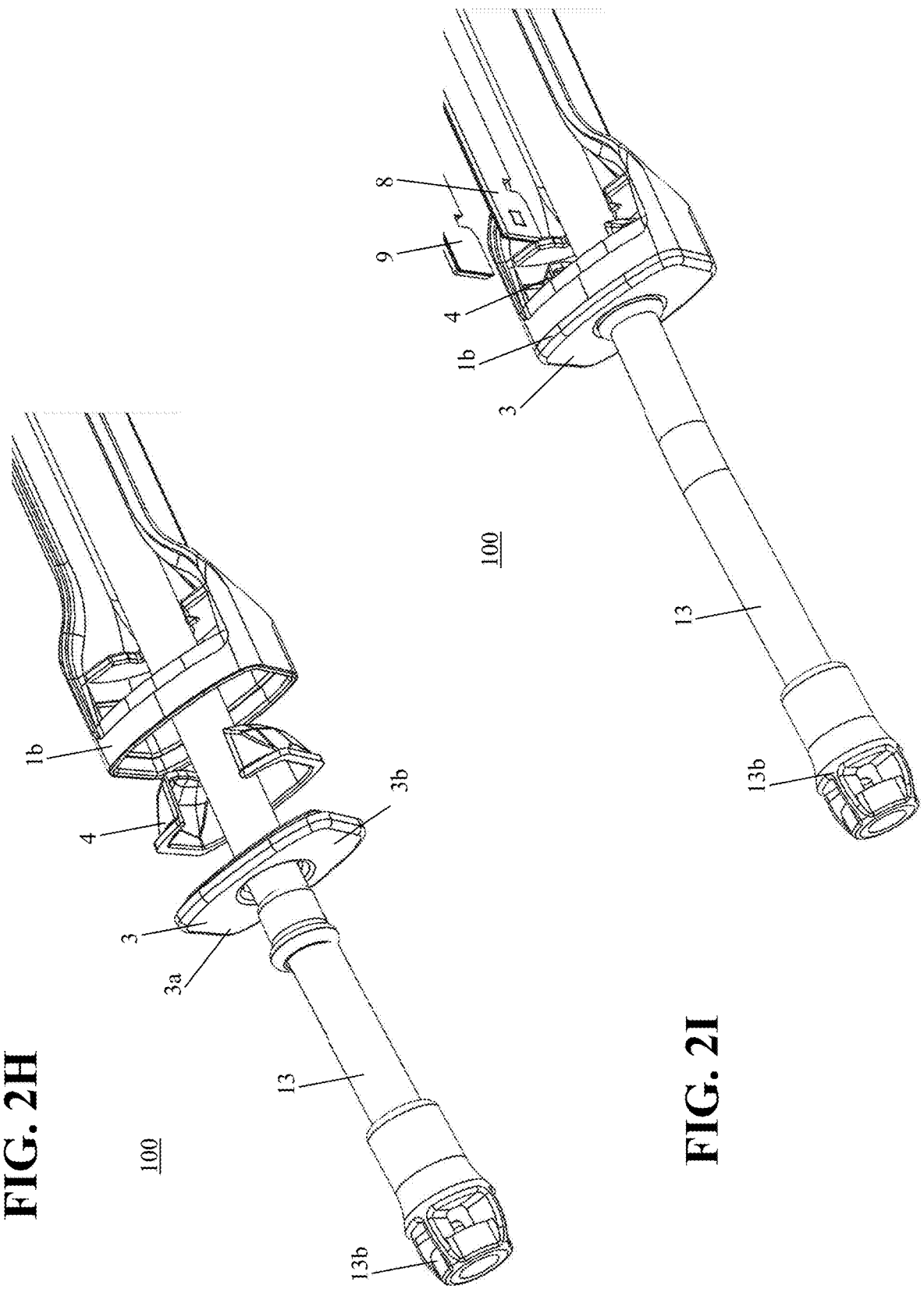

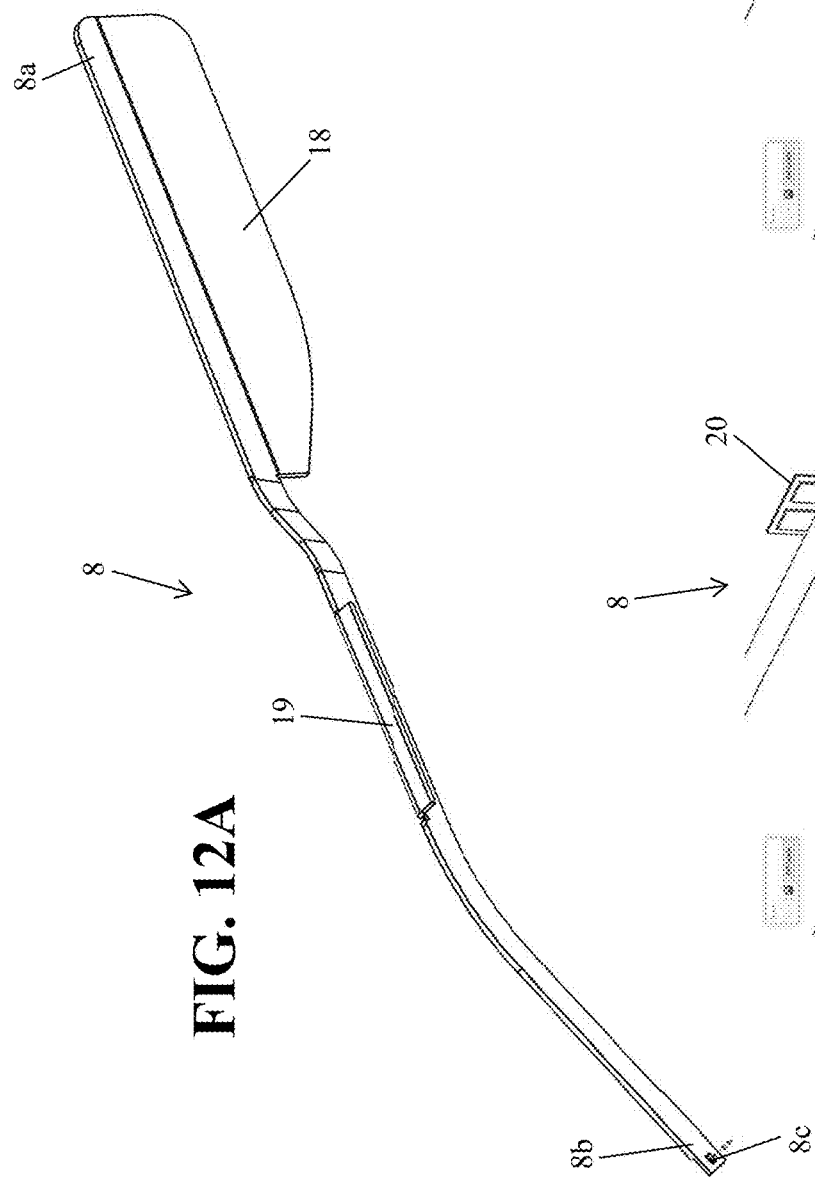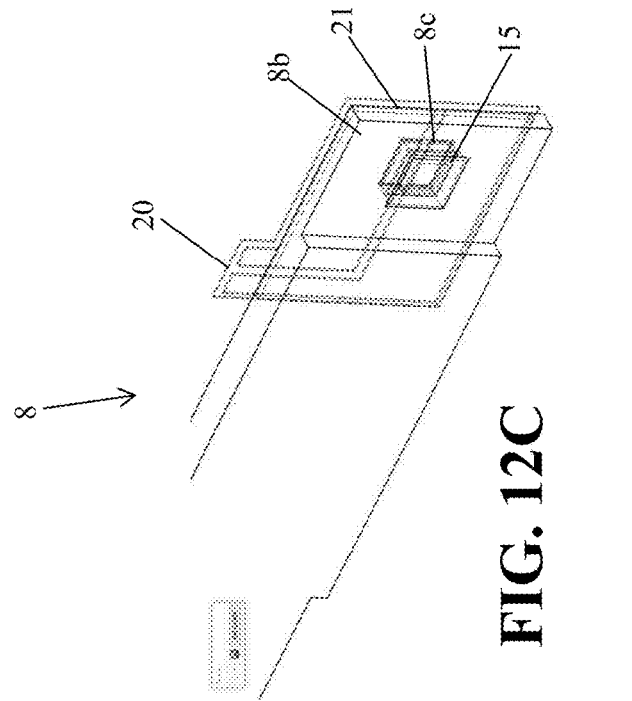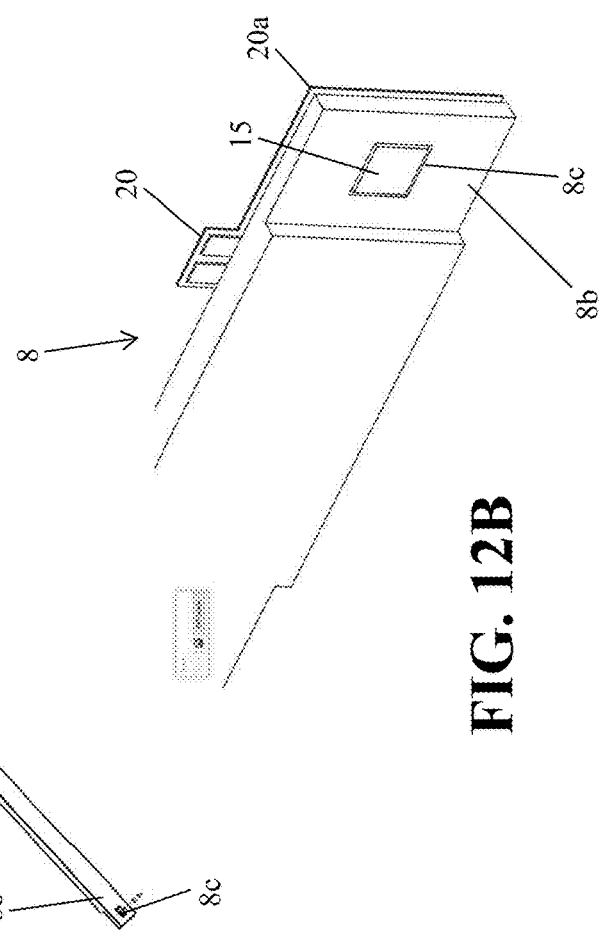
FIG. 12A
FIG. 12B
FIG. 12C

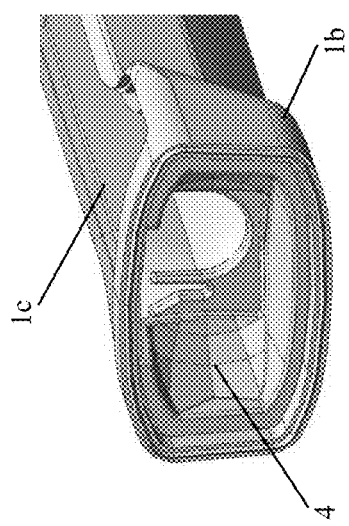
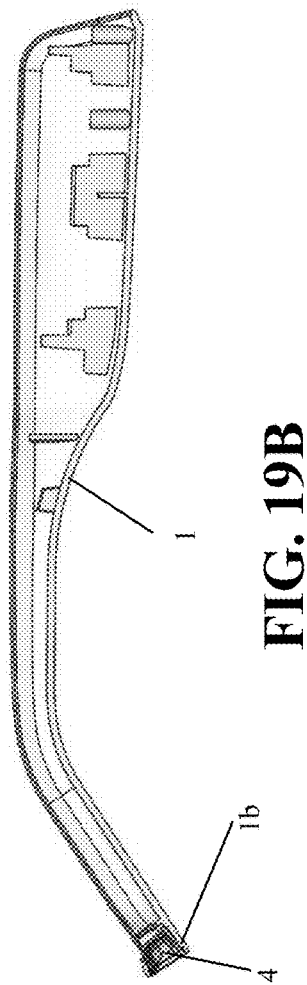
FIG. 19A
FIG. 19B

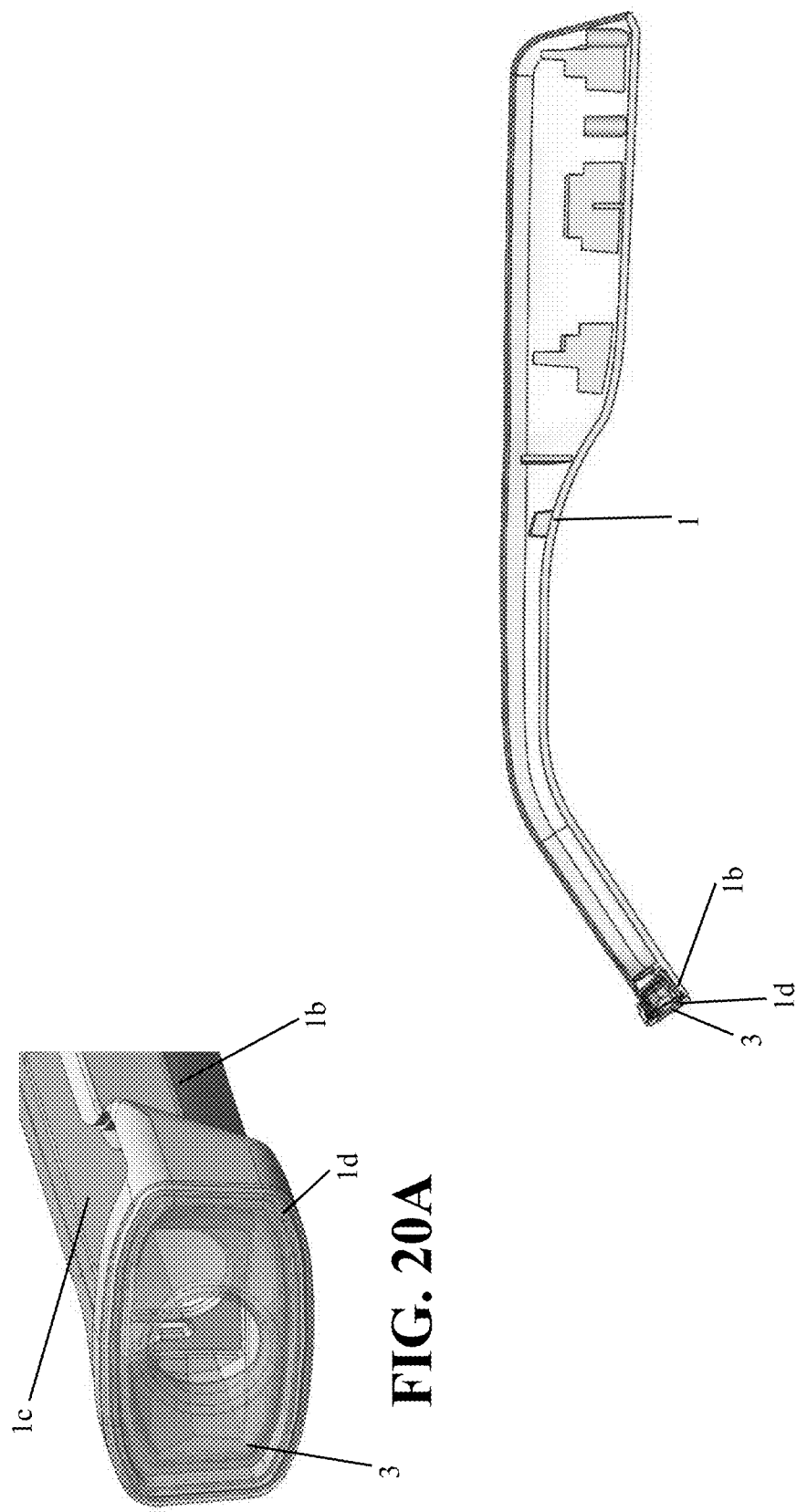

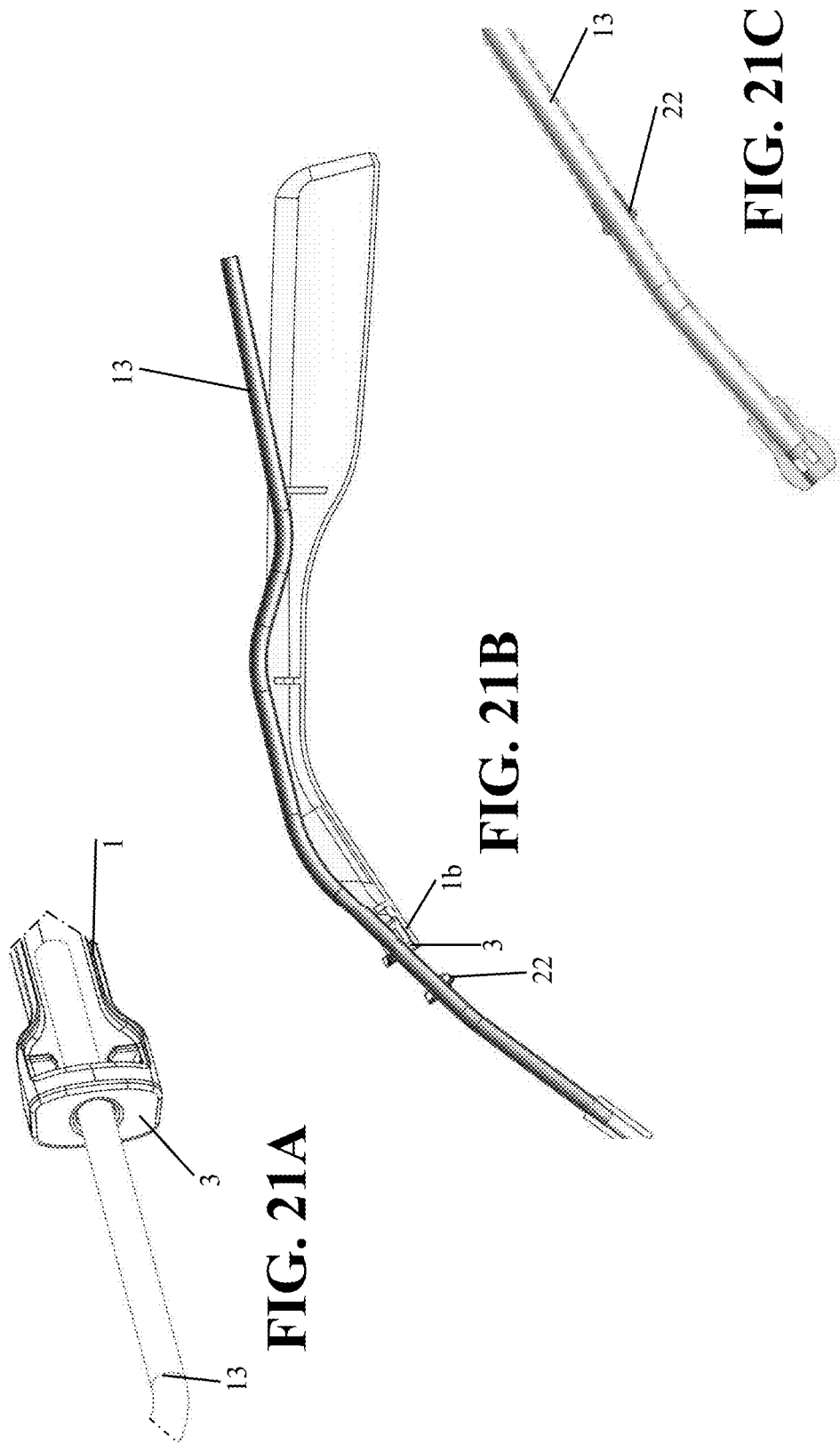

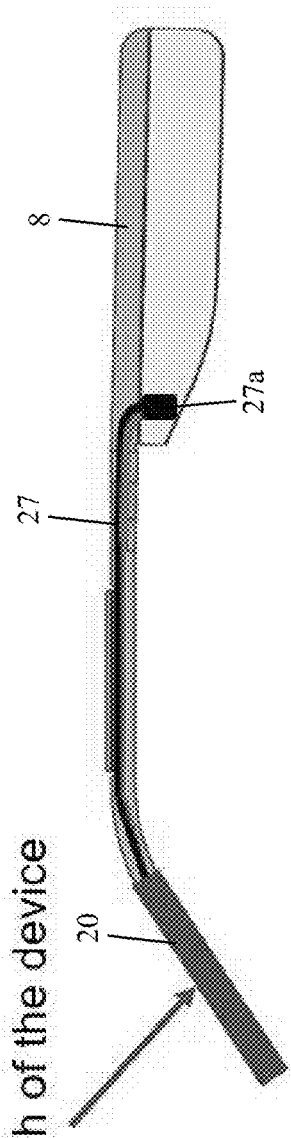
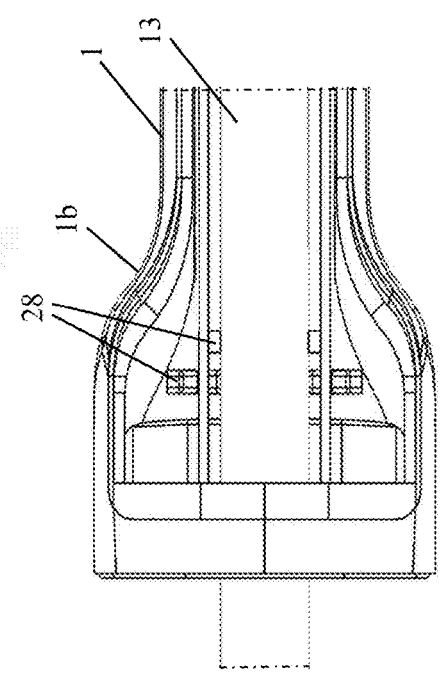
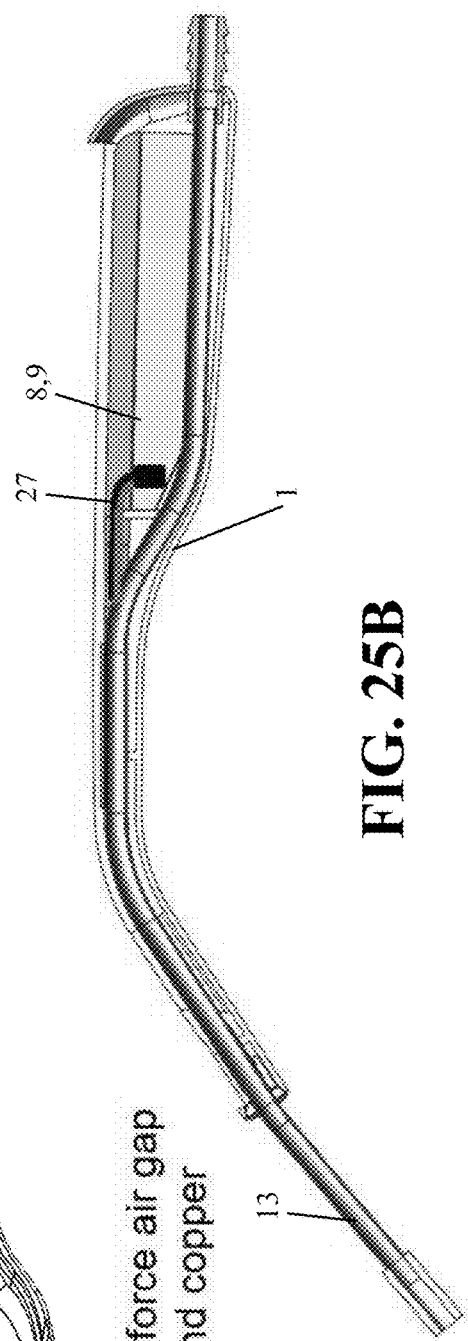
FIG. 24 — Flex circuit with wires soldered to run the length of the device
FIG. 25A — Ribs in housing force air gap between tube and copper
FIG. 25B

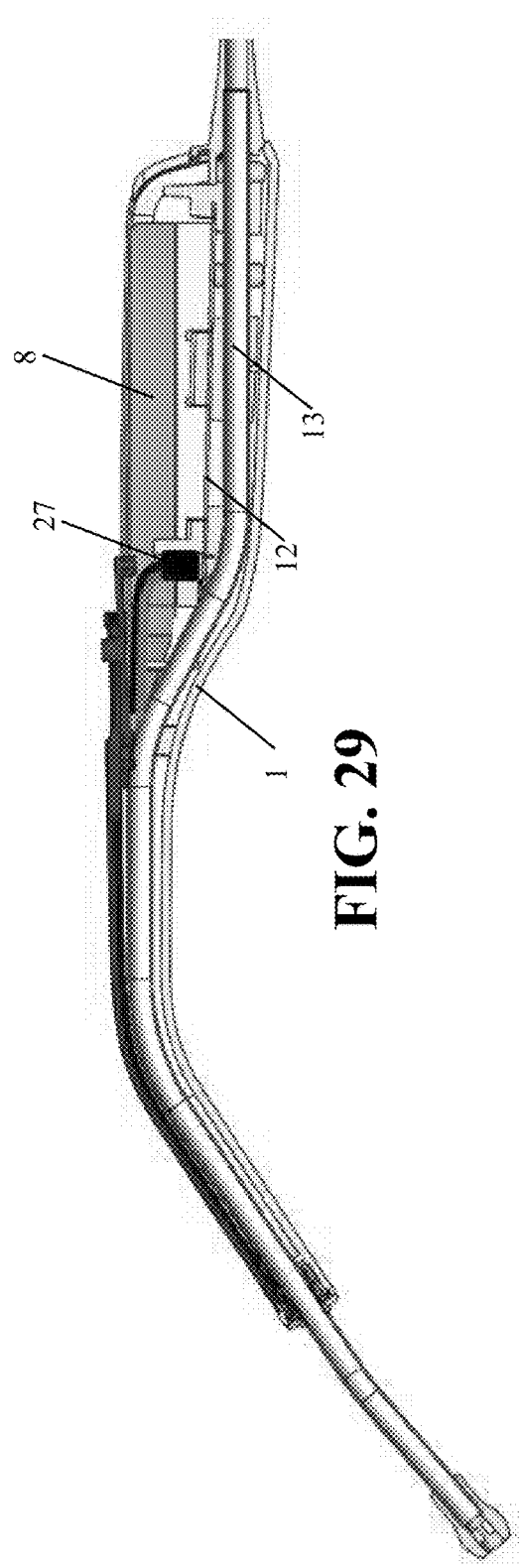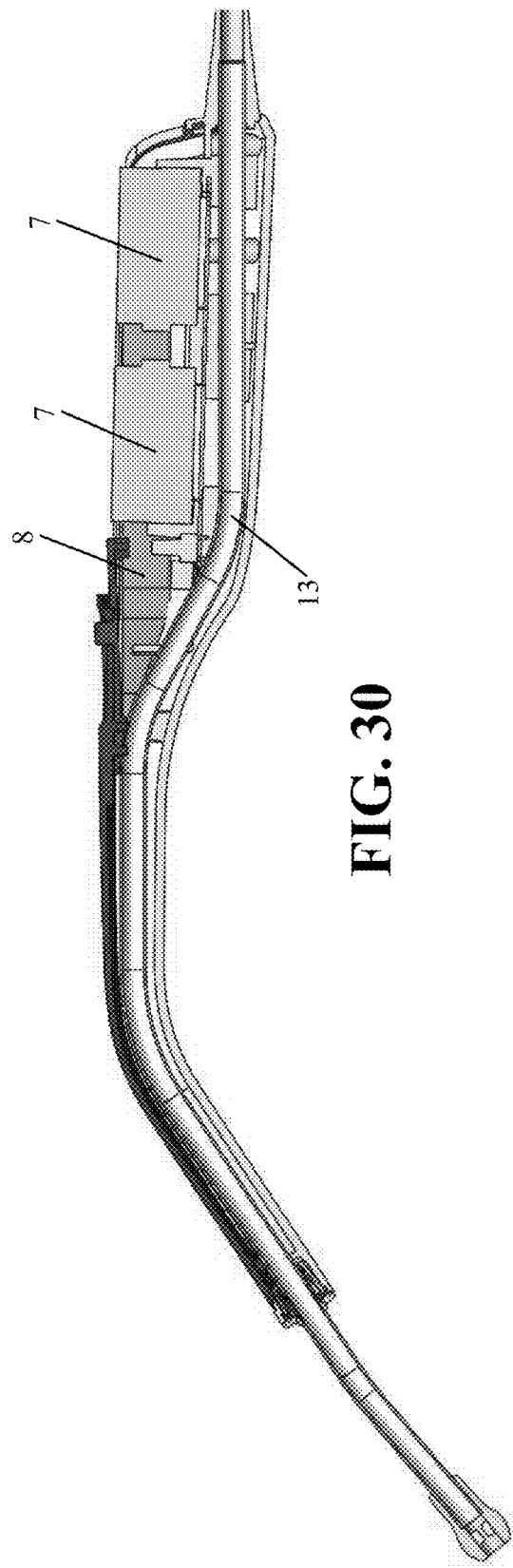

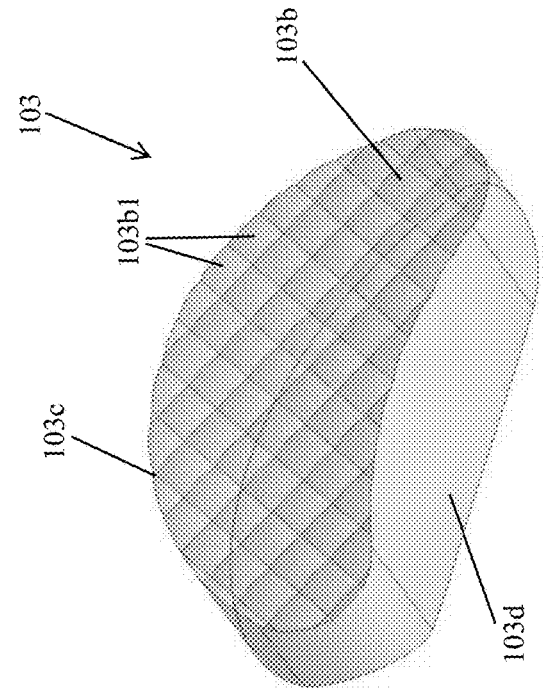
FIG. 32D
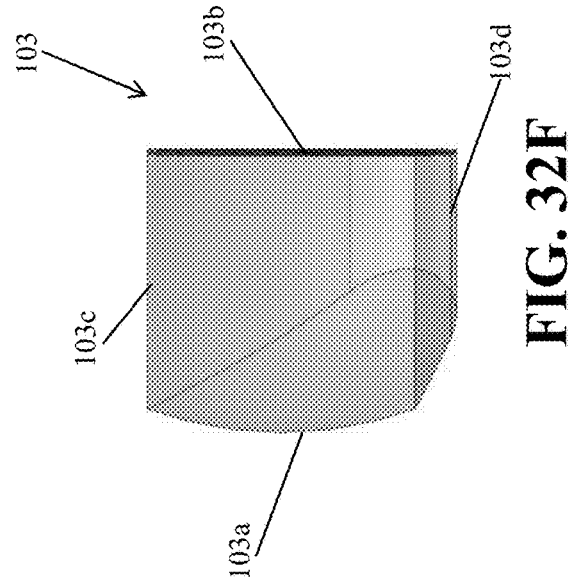
FIG. 32F
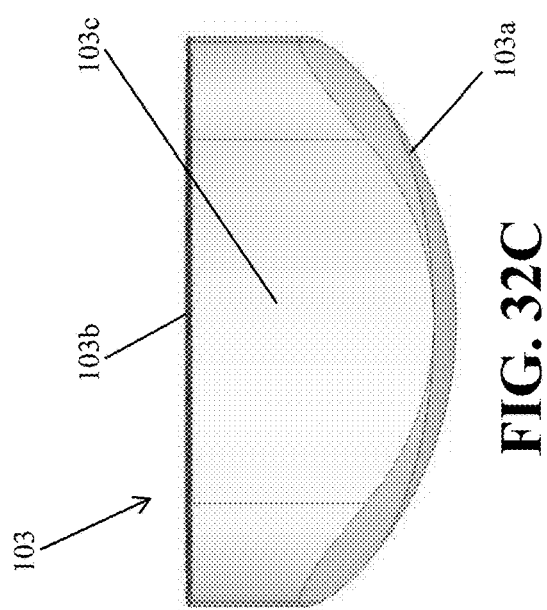
FIG. 32C
FIG. 32E

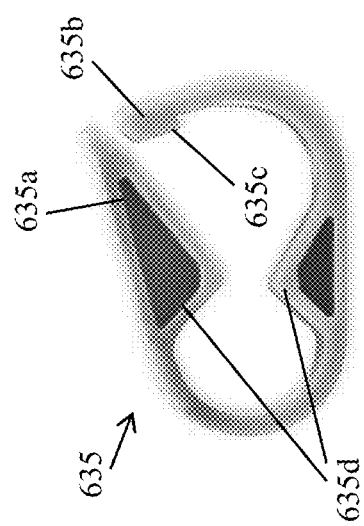
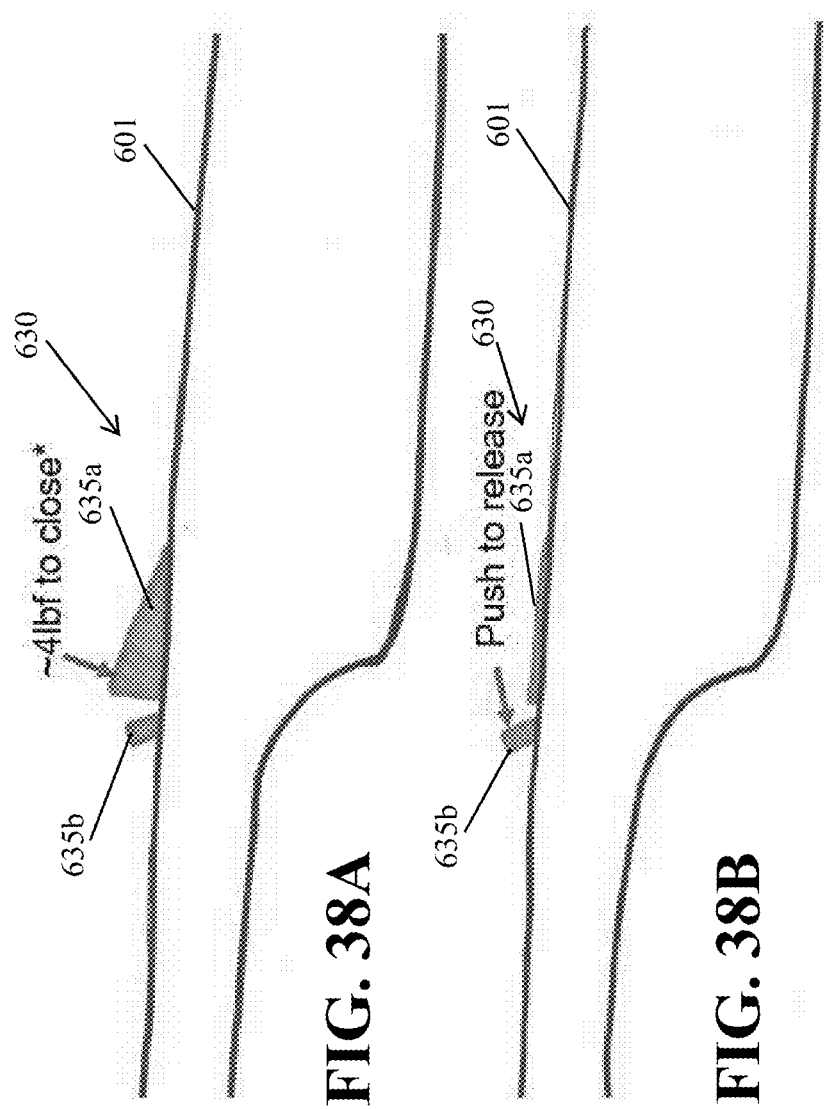
FIG. 38C
FIG. 38A
FIG. 38B

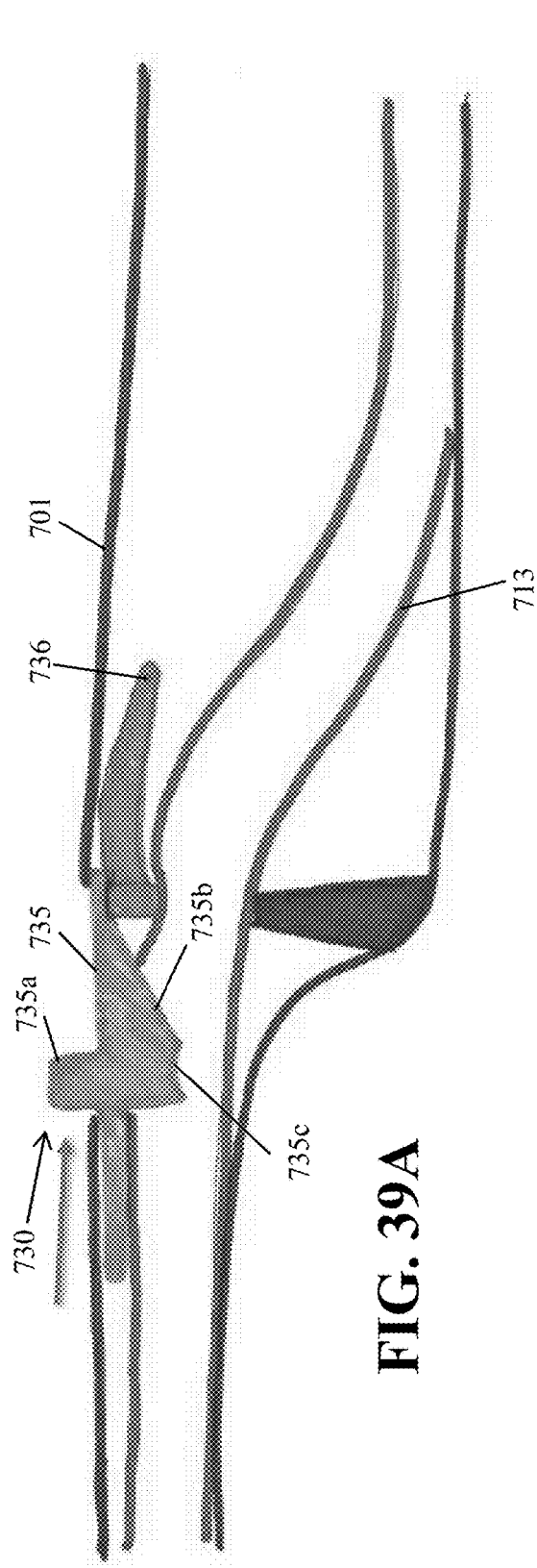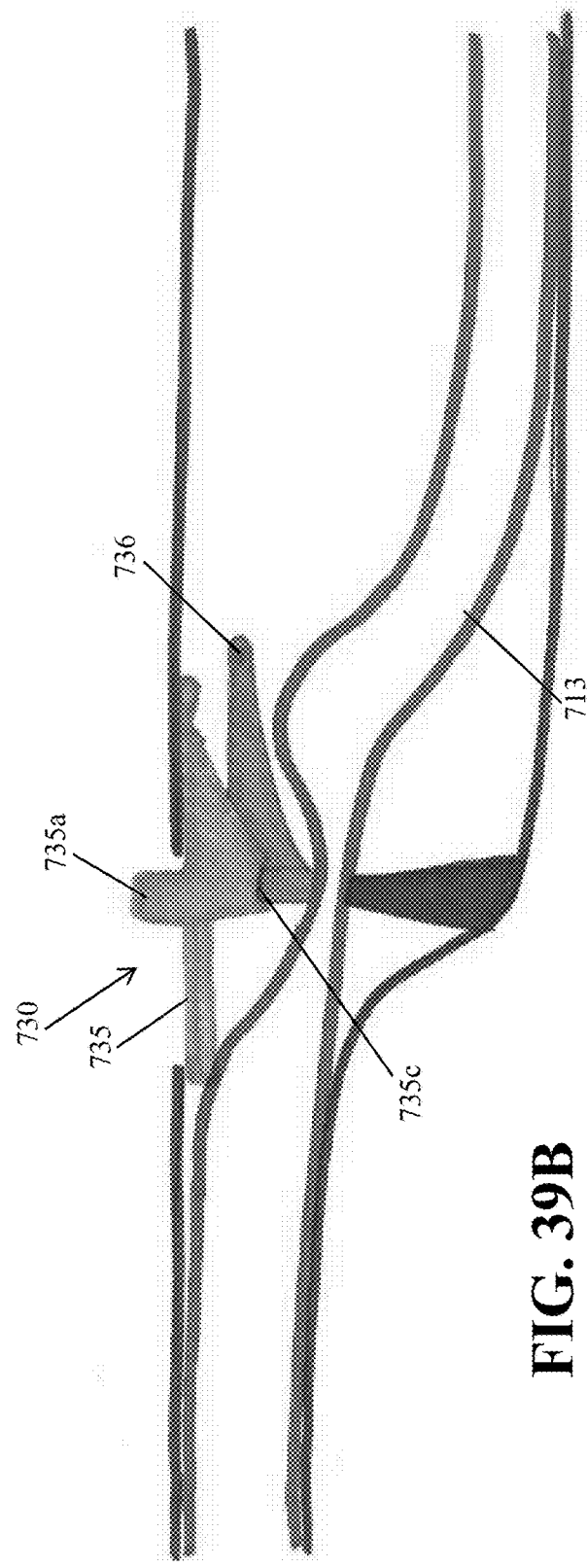
FIG. 39A
FIG. 39B

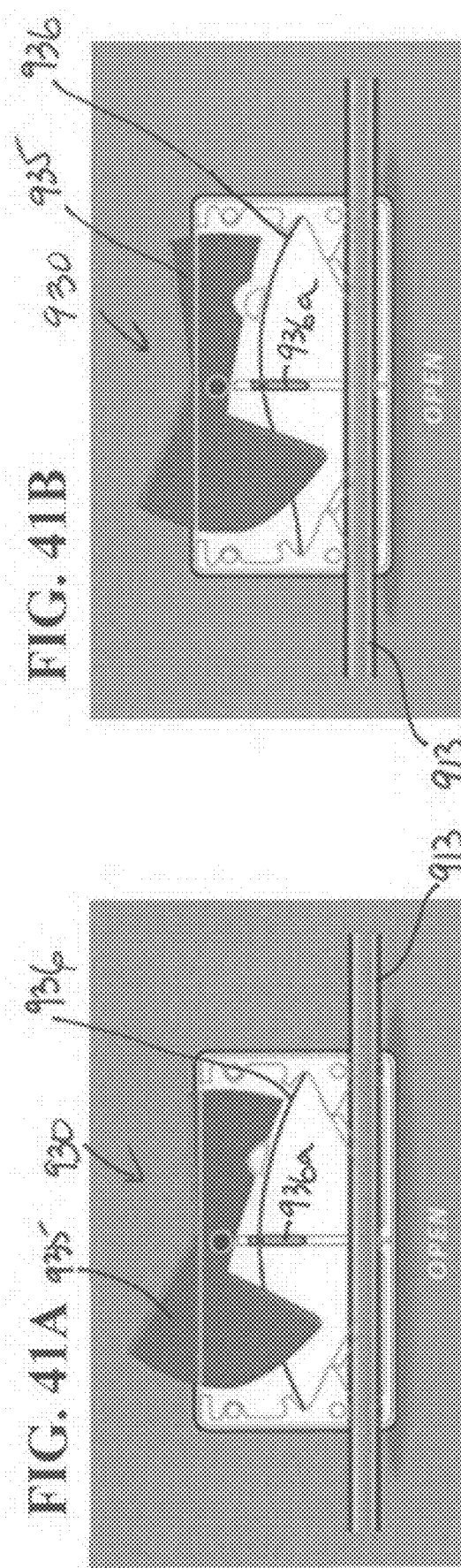
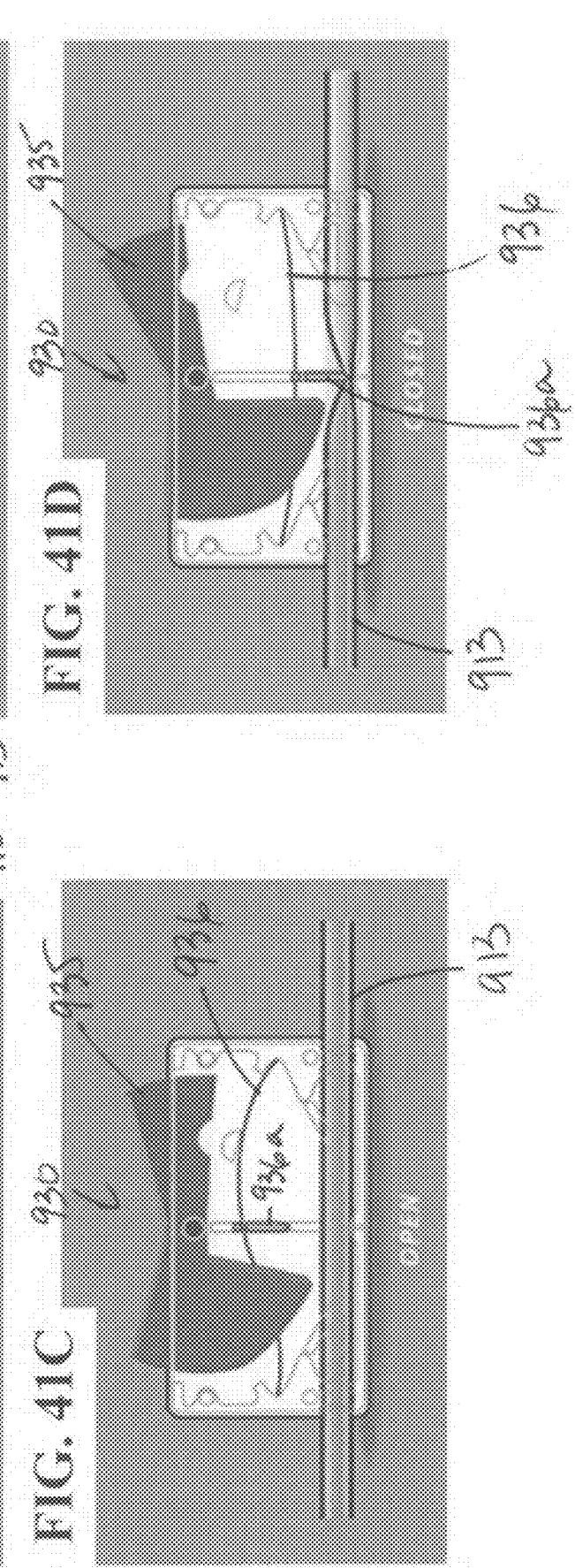
FIG. 41A  FIG. 41B  FIG. 41C  FIG. 41D

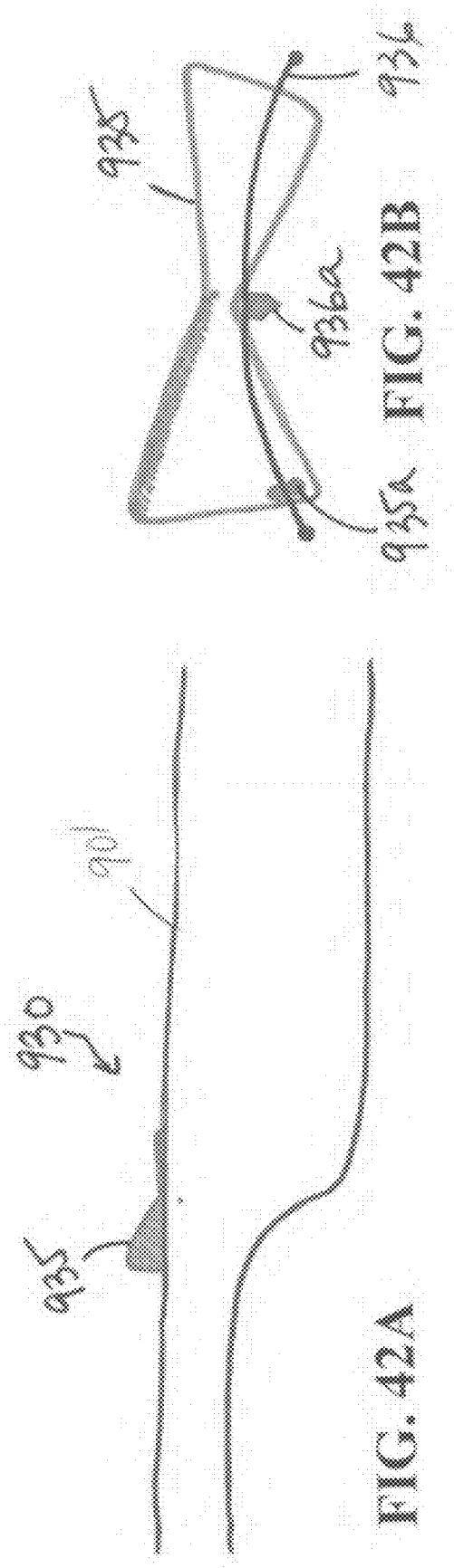
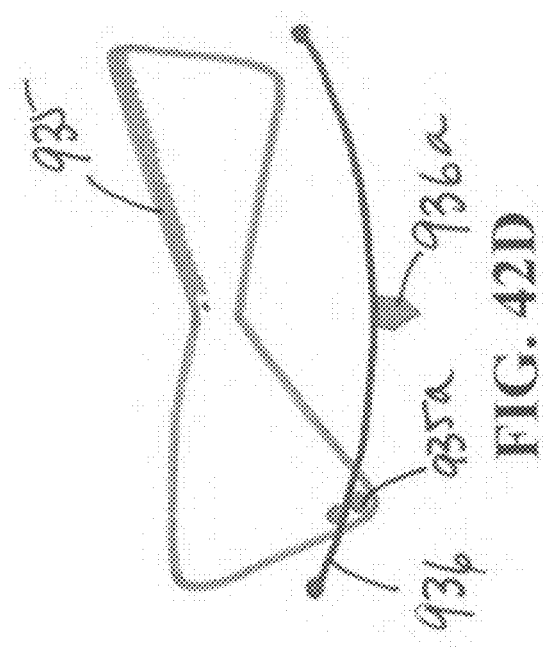
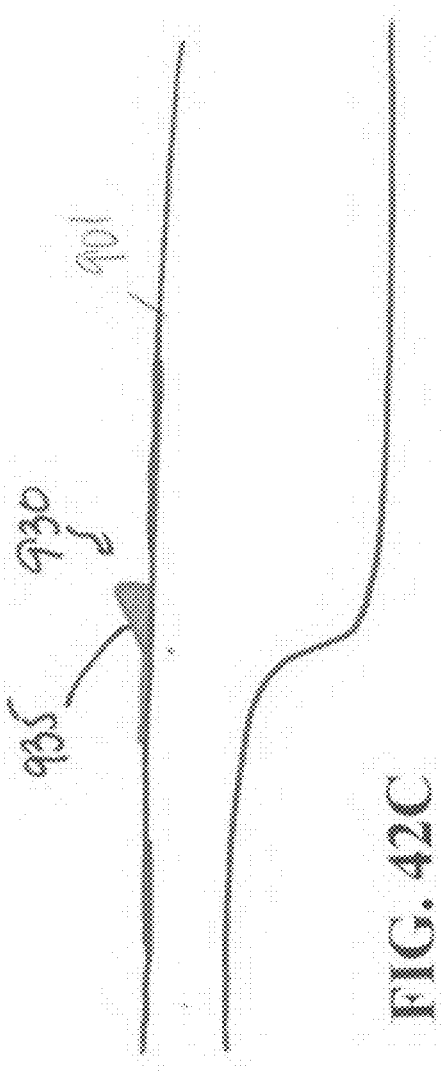
FIG. 42A  FIG. 42B  FIG. 42C  FIG. 42D

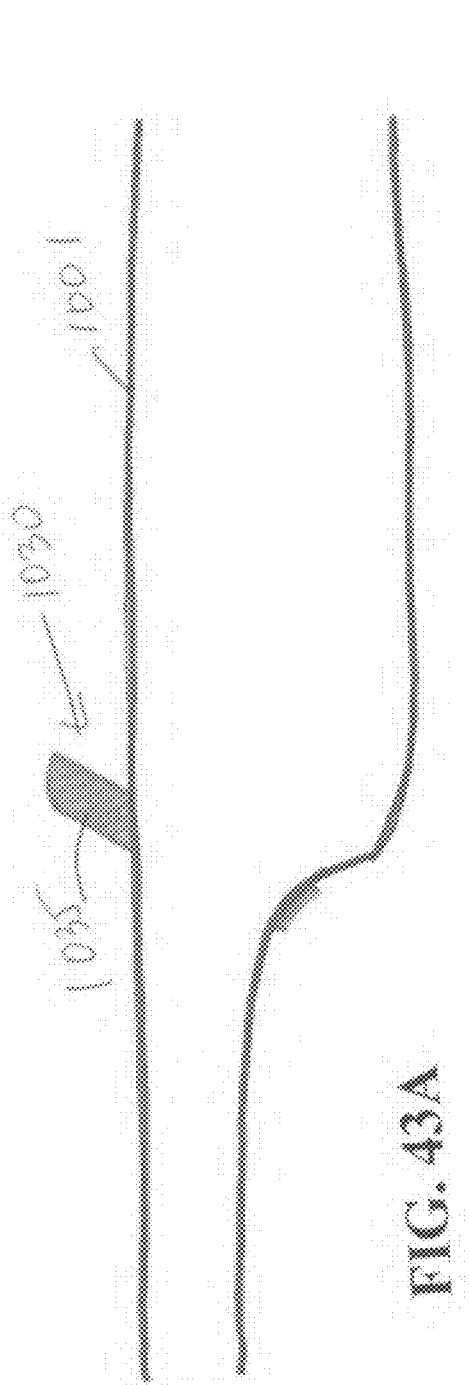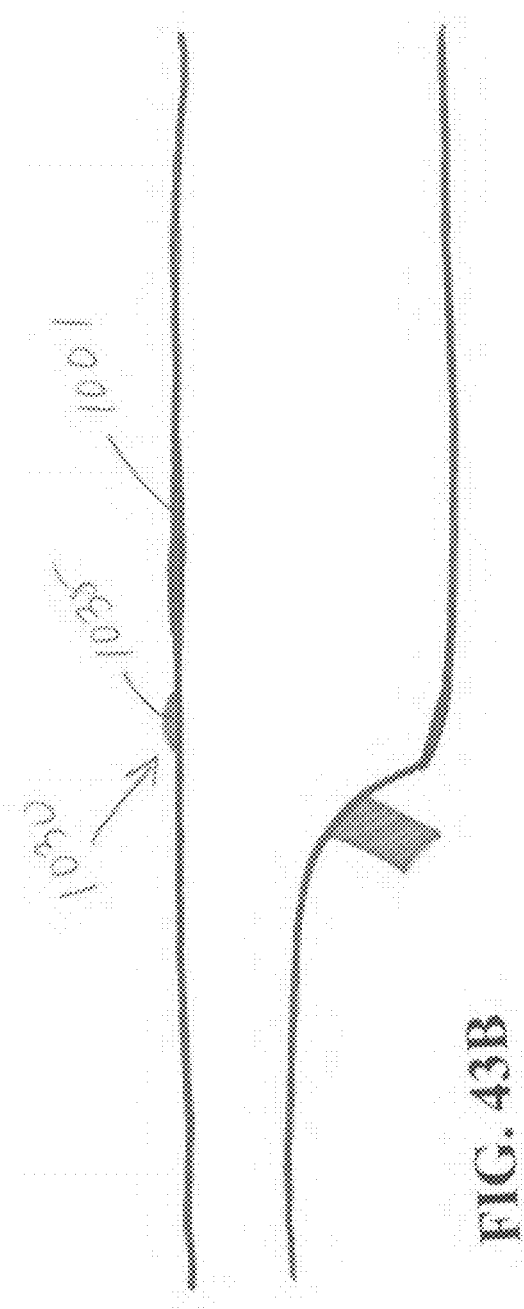

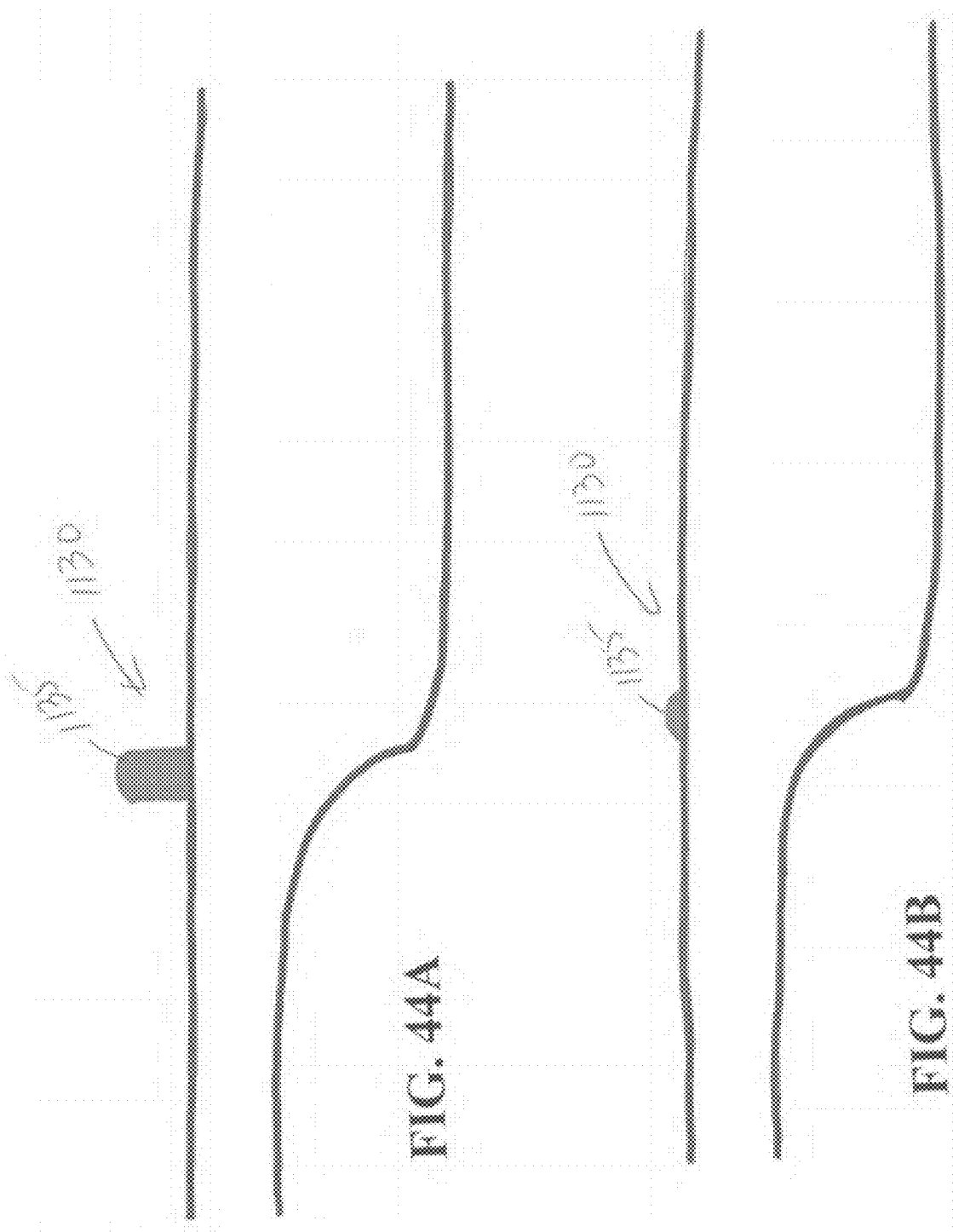

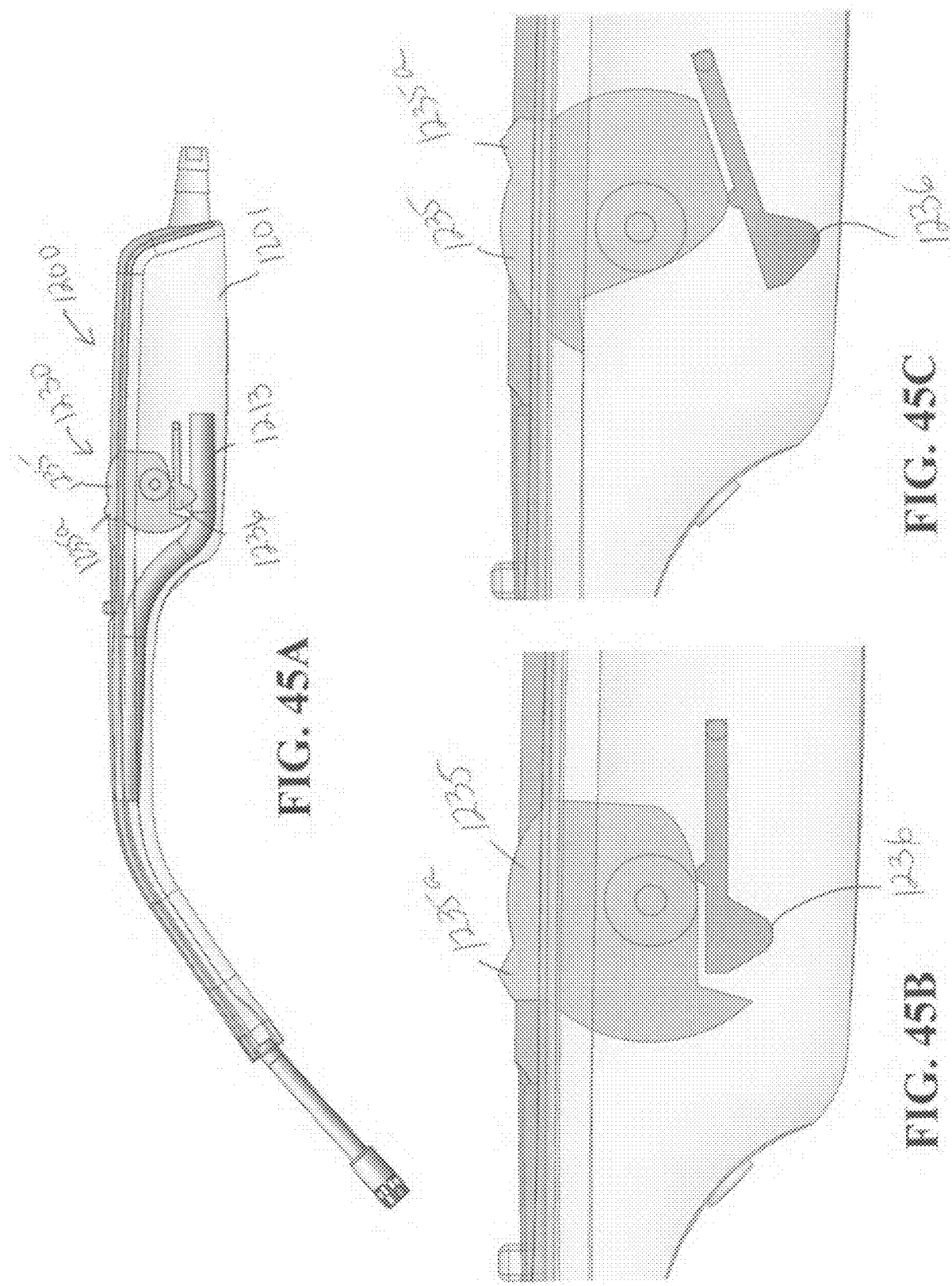

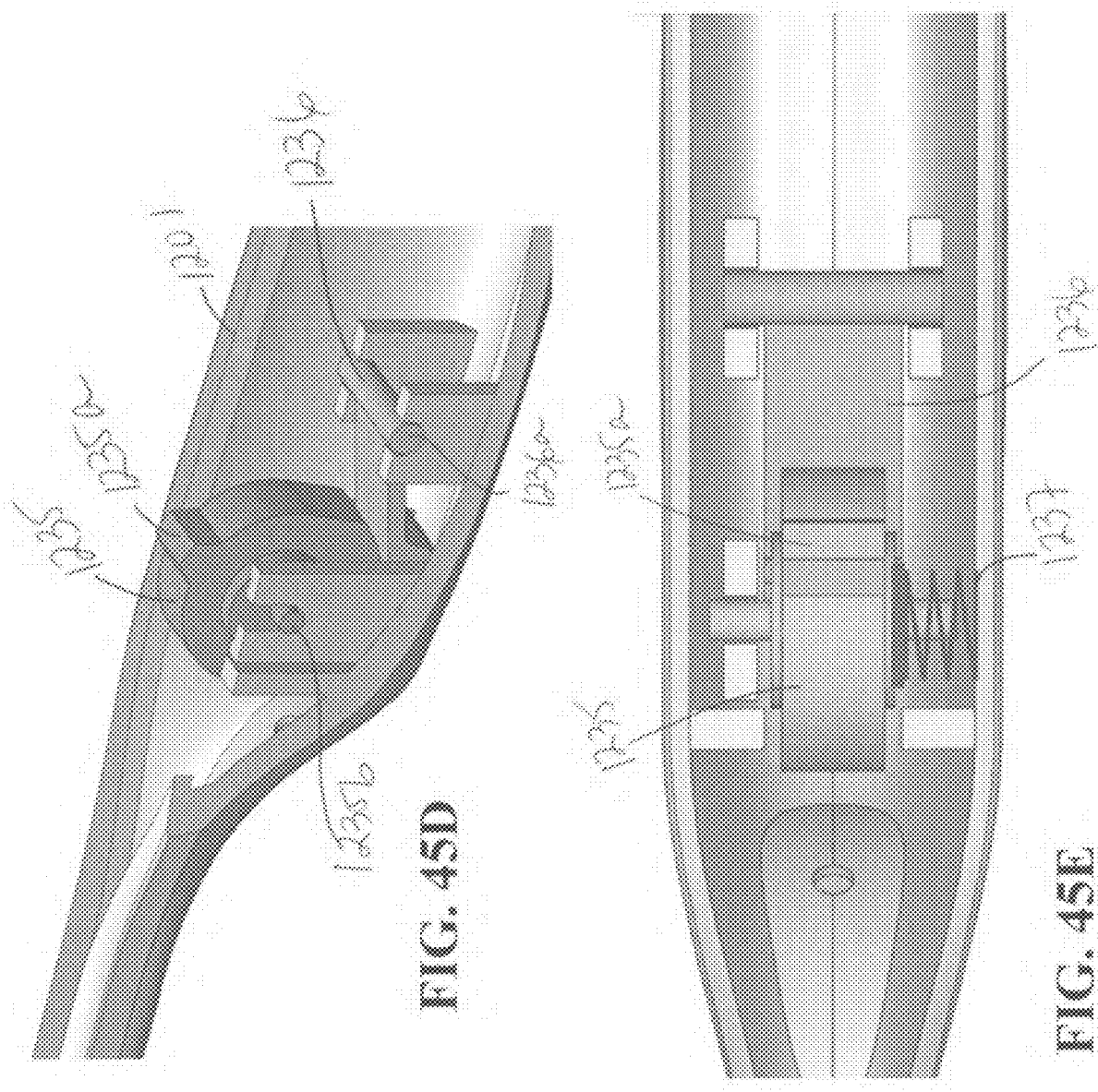

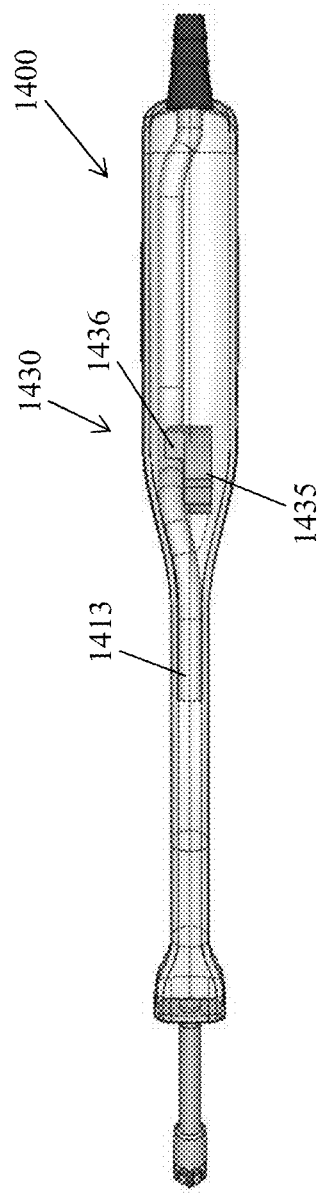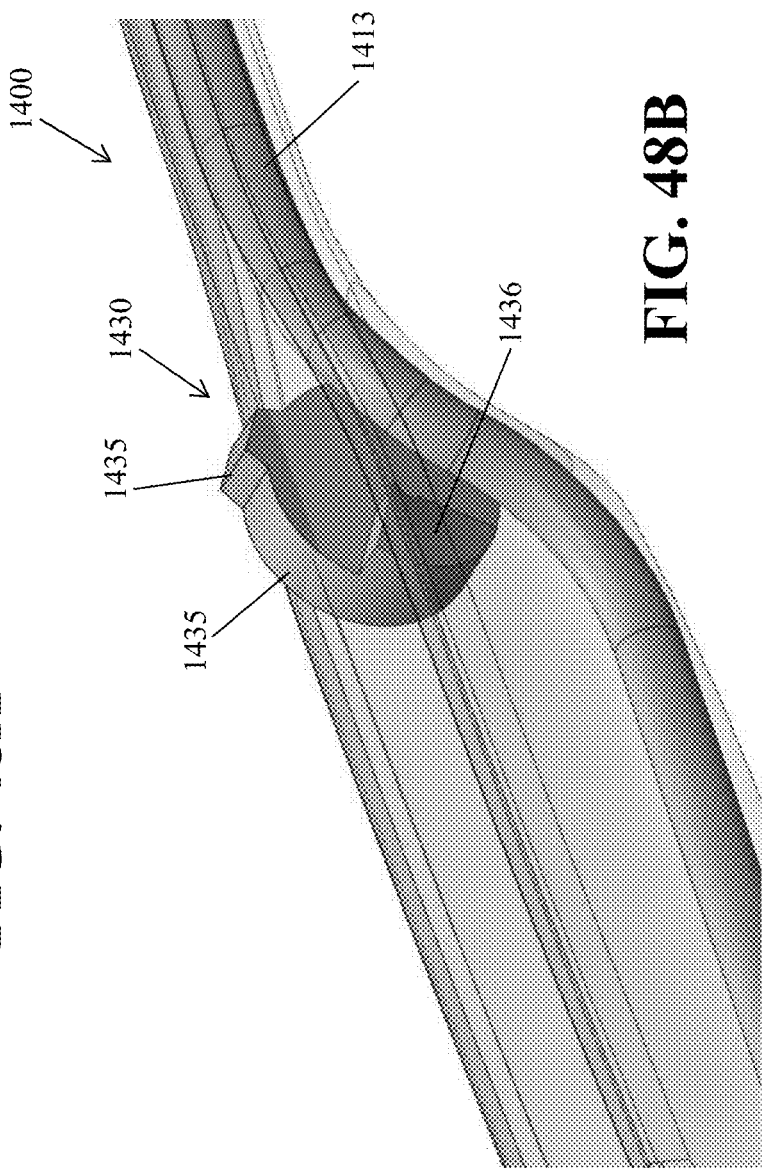
FIG. 48A
FIG. 48B

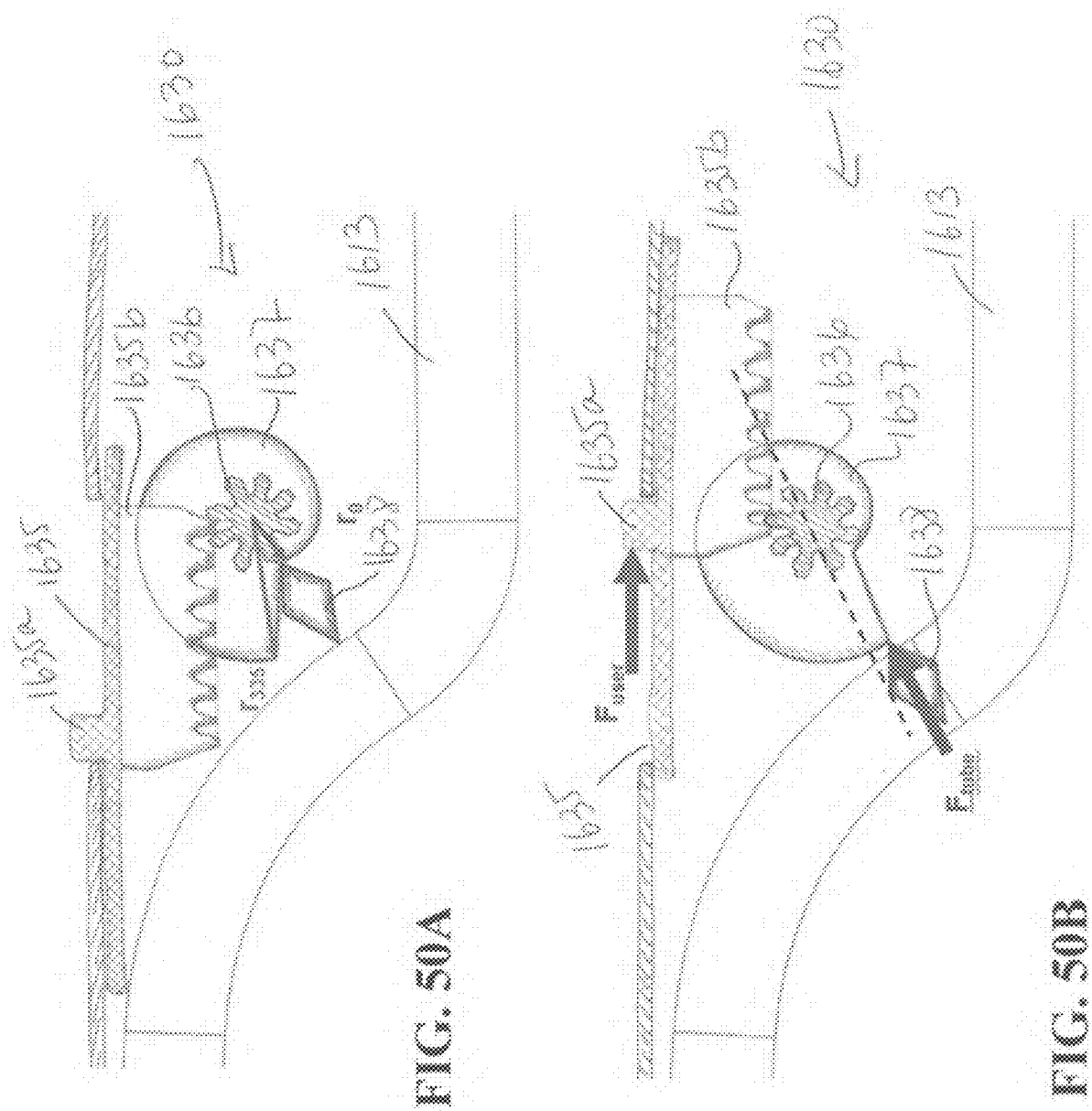

ILLUMINATED SUCTION DEVICE

FIELD OF THE INVENTION

Embodiments described herein relate to a surgical instrument with a compact illumination assembly for improved lighting and heat dissipation features. The surgical instrument described in the illustrative embodiments herein is especially well suited for the removal of body fluids such as blood from a surgical wound and for simultaneously illuminating an area of the wound so that the same can be visualized by a surgeon.

INTRODUCTION

It is often necessary during the course of a surgical procedure for body fluids, such as blood, to be removed from the area of the surgical wound in order that the same may be visualized by the surgeon. The arrangements hitherto provided for the removal of such fluids from and for the illumination of surgical wounds have left much to be desired.

It is often necessary to maintain a surgical suction device in place in the wound in order to permit the surgeon to visualize the point at which the bleeding has occurred. Particularly when such a suction device is in place, it is extremely difficult and often impossible to prevent the suction device from interfering with the desired visualization and illumination.

Hand-held suction devices are routinely used during surgical procedures. These devices are typically connected to a standard suction source in the operating room, enabling the physician to dynamically and efficiently remove blood, bone fragments, or fluid previously irrigated into the surgical site. These suction devices are sometimes also used to provide low force retraction of fat, muscle, or other structures during the procedure. The surgeon holds the suction device from its proximal end, manipulating the distal portion of the suction device during the surgical procedure in order to provide suction at the desired location. Hand-held suction devices are widely available in a variety of distal tip configurations suited to various surgical applications.

A Yankauer suction device is a medical instrument that provides suction to a wound or other surgical incision to remove fluids from the area. Conventional Yankauer suction devices come in a metal version and a plastic version, which is usually a sterile, single-use suction tool used to remove mucus from the mouth, primarily from the throat. A tail end of the Yankauer suction device is connected to a tubing (which provides the suction) that can work with suction machine devices, and a tip end is inserted into the area to be evacuated. The devices may come with several style tips. Some have a hole at the tip end and some have additional holes on the sides.

Illuminated Yankauer suction devices available for surgical use fall into two categories: first, a suction device with illumination supplied by a fiber-optic light guide connected to the device, with light guided through the light guide to an aperture near the distal end of the suction device, from which the light is directed toward the surgical field; and second, illumination supplied by an LED installed on the instrument and powered by batteries, with unmodified luminance from the LED being aimed toward the surgical field. U.S. patent application Ser. No. 15/646,372, assigned to the same assignee herein and incorporated herein by reference, is an example of an illuminated suction device falling into the second category.

The first category of suction devices is constrained by the need for its umbilical cord, i.e., light guide, tethering it to a large, heavy, expensive, relatively non-portable, AC-powered light source. The limited flexibility of the light guide tends to hamper the use of the tool by the surgeon. The second category of suction devices have an LED coupled to the top, i.e., 12 o'clock, position on the tube of the suction device and relies on the native luminance pattern of the LED to project an acceptable pattern of illuminance onto the target surgical field. The target surgical field or target area (target surface) is typically defined as a relatively flat surface in contact with, and substantially perpendicular to, the tip of the suction tube. In addition, the luminance pattern is constrained by the limited shapes of the LEDs and the limited space available on the suction tube for attaching the LED in a way that would avoid blocking the view of the surgical field during use and avoid increasing the size of the suction tube.

With both categories of existing illuminated suction tube surgical instruments, the illuminance pattern at the target surface is the most intense at the center, with a radial decline in illuminance when measuring away from the center. In addition, the illuminance pattern at the target surface displays a darker shaded portion just under the tip of the suction tube. This is because typically illuminated suction tools have their light-emitting aperture located above the suction tube, i.e., at 12 o'clock when the tube is viewed as a clock face. Therefore, typically the suction tube itself casts a shadow at a 6 o'clock position on the target surface.

SUMMARY OF THE INVENTION

The present invention provides an improved illuminated medical device, such as a Yankauer suction device, which provides a uniform illuminance pattern over a circular target area and eliminates formation of a shadow from the medical device in the illuminated target area. The target area (target surface) is a surface in contact with or near the distal tip of the suction tube and substantially perpendicular to the distal tip of the suction tube.

Moreover, the illuminated medical device of the present invention provides bright illumination, without increasing the bulk of the device so that the device can be inserted into small spaces and so that the illumination assembly does not obscure the surgeon's field of view. Specifically, the illuminated medical device of the present invention achieves an improved level of illuminance for a sufficient time duration, while keeping the size and weight of the onboard energy source (typically batteries) reasonably small for a hand-held tool. In addition, the device of the present invention includes heat dissipation features that prevent the illumination assembly from heating the device and avoid potential injury to patient tissues. Other features of the illuminated medical device of the present invention are described in the detailed description.

In accordance with the present invention, an illuminated medical device comprises an outer housing, and an illumination assembly comprising at least one direct light source oriented to emit light radially away from a central axis of the medical device and at least one reflector configured to reflect light from the at least one direct light source toward a target area external to the outer housing. The illumination assembly does not include a waveguide. The medical device includes a proximal end and a distal end, and wherein the target area is adjacent the distal end of the medical device.

In certain embodiments, the at least one reflector is a concave reflector, and may be a multi-faceted reflector, and wherein the direct light source is positioned within a concavity of the at least one reflector. In some embodiments, the illumination assembly further includes at least one lens for refracting light reflected from the at least one reflector toward the target area. In some illustrative embodiments, the at least one direct light source includes a first direct light source oriented to emit light radially away from the central axis of the medical device in a first direction and a second direct light source oriented to emit light radially away from the central axis of the medical device in a second direction different from the first direction, and wherein the at least one reflector reflects light emitted from the first direct light source and light emitted from the second direct light source toward the same target area. The first direction may be opposite to the second direction.

In some embodiments, the illuminated medical device is a suction device further comprising a suction tube extending from the outer housing and wherein the target area is adjacent to a distal end of the suction tube.

The present invention is also directed to an illuminated suction device comprising an outer housing having a suction tube extending therethrough, and an illumination assembly including a plurality of direct light sources and a built-in power source for supplying power to the plurality of direct light sources, said power source being housed within the outer housing. In some embodiments, each of the plurality of direct light sources is provided at a different location around the suction tube. In certain embodiments, the plurality of direct light sources include a first direct light source provided adjacent to one side of the suction tube and a second direct light source provided adjacent to another side of the suction tube. In certain embodiments, the illumination assembly further includes one or more optical elements including one or more of a reflector and a lens.

In some arrangements of the illumination assembly, each of the plurality of direct light sources emits light radially away from the suction tube and the one or more optical elements are configured to direct light emitted from the plurality of direct light sources toward a target area adjacent to a distal tip of the suction tube. The one or more optical elements include at least one concave reflector configured to reflect light emitted from the at least one direct light source toward the target area.

In some embodiments, the outer housing includes a proximal end and a distal end, the suction tube extends from the proximal end of the outer housing and beyond the distal end of the outer housing, and the built-in power source is provided adjacent the proximal end of the outer housing.

In some embodiments, the illuminated suction device further comprises a heat sinking assembly for dissipating heat generated by the plurality of direct light sources, the heat sinking assembly comprising one or more heat sinking members thermally connected to the direct light sources. The heat sinking assembly may include a plurality of heat sinking members, each said heat sinking member being thermally connected with a direct light source and each said heat sinking member comprising a metallic plate having a high thermal conductivity.

The present invention is also directed to an illuminated suction device comprising an outer housing having a suction tube extending therefrom, and an illumination assembly including one or more direct light sources and one or more optical elements, said illumination assembly being configured to provide substantially shadowless, substantially uniform light to a target area adjacent a distal end of the suction tube. In some embodiments, the one or more optical elements include one or more of a reflector and a lens. In some embodiments, the illumination assembly includes a plurality of direct light sources and the one or more optical elements includes at least one concave reflector for reflecting light emitted from the plurality of direct light sources toward the target area, with the plurality of direct light sources being positioned within a concavity of the at least one concave reflector. Each of the direct light sources is oriented so as to emit light radially in a direction away from a central axis of the suction tube. In one arrangement, the plurality of direct light sources include a first light source positioned adjacent a first side of the suction tube and a second light source positioned adjacent a second side of the suction tube opposite of the first side. The one or more optical elements may further include at least one lens for refracting light reflected from the at least one concave reflector.

Applicant's invention is also directed to an illuminated medical device comprising: an outer housing, an illumination assembly at least partially enclosed by the outer housing and including a plurality of direct light sources for providing illumination from the outer housing, and a heat sinking assembly comprising a plurality of heat sinking members, each heat sinking member being thermally coupled with at least one of the direct light sources.

In some embodiments, each heat sinking member comprises a metallic plate member including one or more through openings, each of said through openings being configured to accommodate one of the direct light sources. In some embodiments, the plurality of direct light sources are mounted on one or more flexible circuits and each flexible circuit is thermally coupled to a corresponding heat sinking member using adhesive thermal tape. In some arrangements, each heat sinking member extends along a substantial portion of a length of the outer housing. In some arrangements, each heat sinking member extends along a substantial portion of the length of the outer housing and at its proximal end expands a really to effect a relatively large amount of thermal transfer to the outer housing.

In some embodiments, the medical device is a suction device including a suction tube extending from the outer housing. The suction tube extends within the outer housing and along at least a substantial portion of a length of the outer housing, and the outer housing includes projections therein for maintaining an air gap between the suction tube and the plurality of heat sinking members.

Other arrangements and features of the invention are contemplated and described herein below.

BRIEF DESCRIPTION OF THE DRAWINGS

The above and other features and aspects of the present invention will become more apparent upon reading the following detailed description in conjunction with the accompanying drawings, in which:

FIGS. 1A-1G show different views of the illuminated suction device of the present invention;

FIG. 2A shows a close-up view of a distal end of the suction device with an illumination assembly in accordance with the present invention;

FIG. 2B shows the distal end of the suction device of FIG. 2A with a top cover/spine removed to expose the illumination assembly;

FIG. 2H shows the distal end of the suction device of FIG. 2E with an exploded view of the illumination assembly;

FIG. 2I shows the distal end of the suction device of FIG. 2E with the top cover/spine removed and with heat sinking members removed therefrom;

FIG. 12A shows an exemplary heat sinking member for dissipating heat;

FIGS. 12B-12D show assembly of the heat sinking member with the illumination assembly shown in FIGS. 2A-2D;

FIGS. 19A-31 show an exemplary sequence of assembling the illuminated suction device of FIGS. 1A-1G;

FIGS. 37A-52B show different embodiments of flow control assemblies that can be incorporated into the suction device of FIGS. 1A-1G and 32A-36B or into other medical devices incorporating suction features.

DETAILED DESCRIPTION OF EXEMPLARY EMBODIMENTS

Figure 1A:
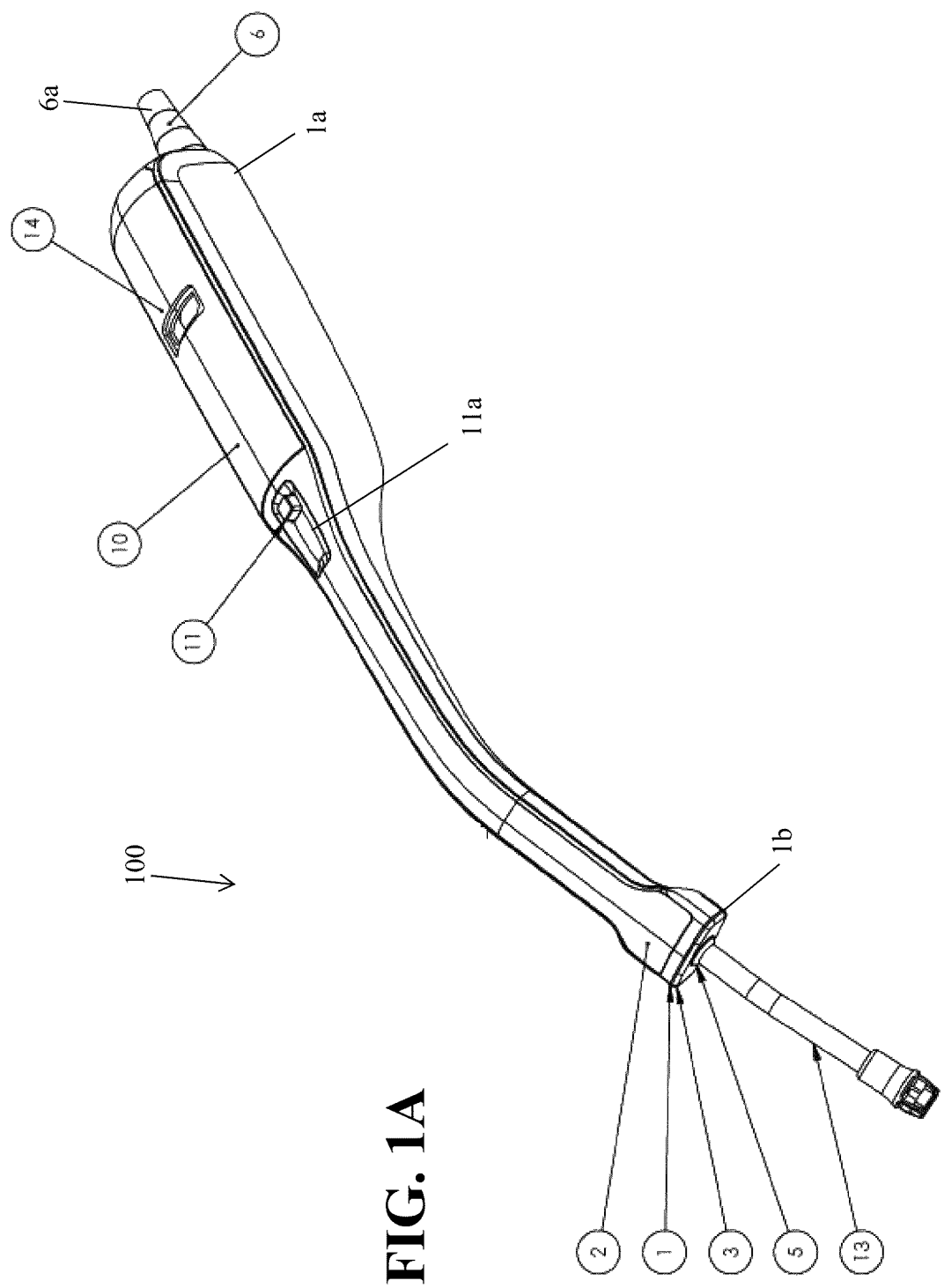
Figure 1B:
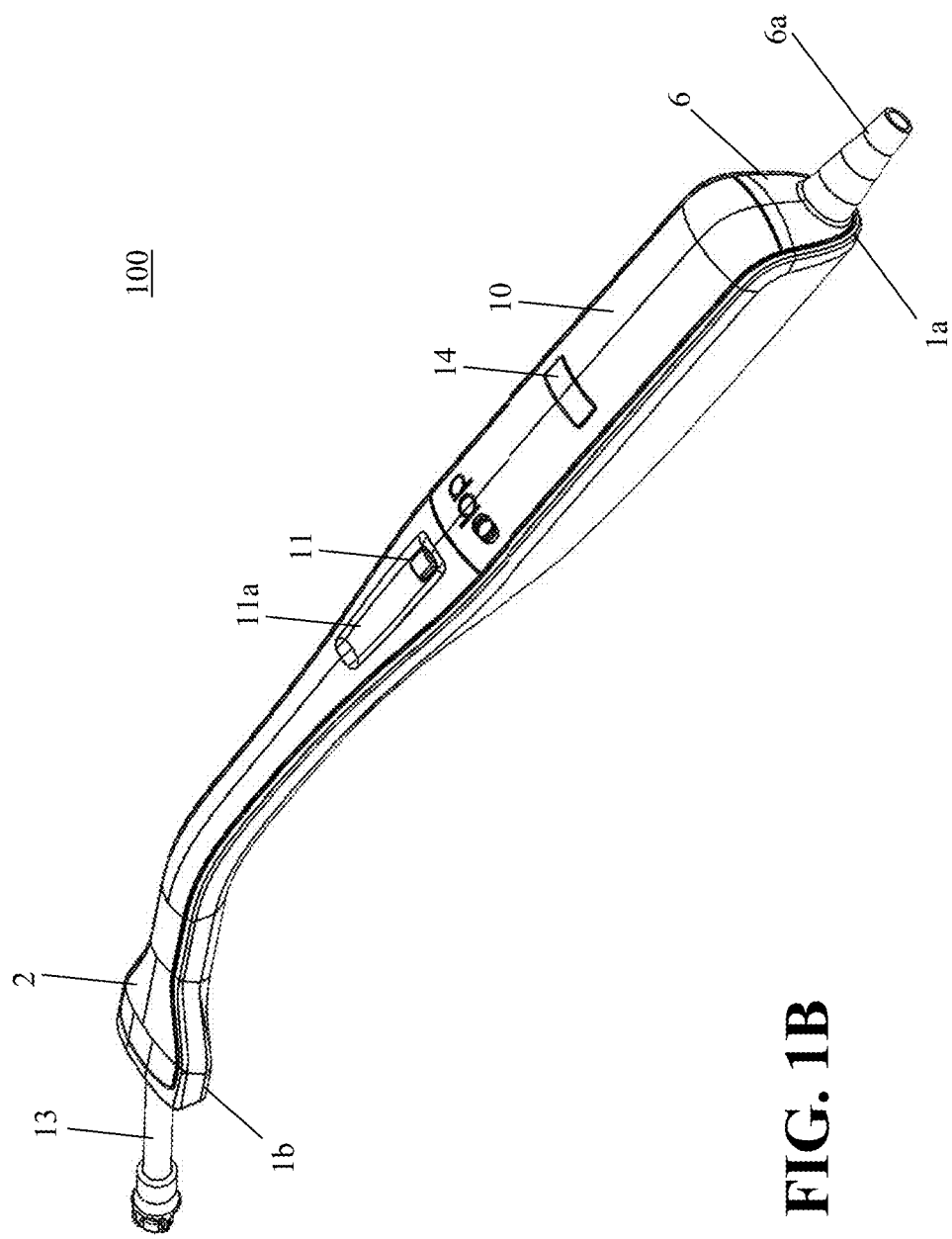
Figure 1G:
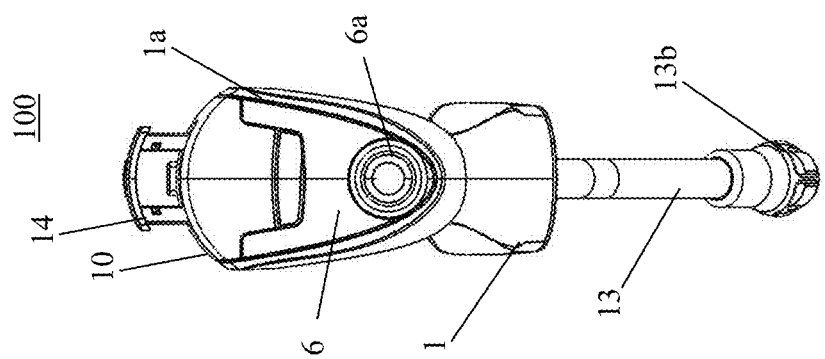
Figure 1F:
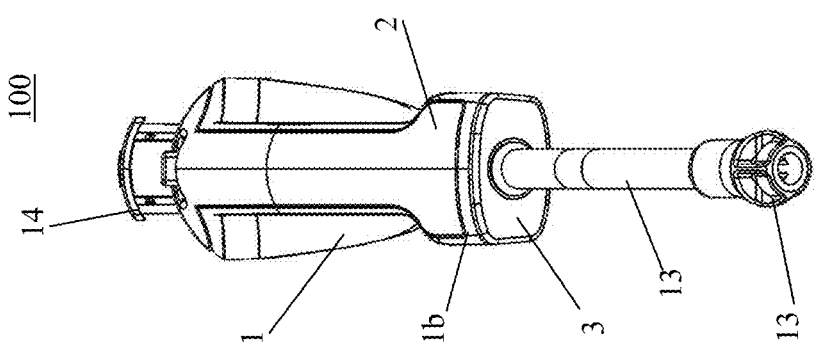

Drawings have been used herein to depict select exemplary embodiments. For the sake of clear illustration, many practical details are explained together in the description below. However, it should be appreciated that those details should not be used to limit the scope of any claims that issue in connection with this application. In some embodiments, certain details are not essential.

Moreover, for the sake of drawing simplification, some customary structures and elements in the drawings have been shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art. It should be further understood that terms, such as those defined in commonly used dictionaries, should be interpreted as having a meaning that is consistent with their meaning in the context of the relevant art and the present description, and should not be interpreted in an idealized or overly formal sense unless expressly so defined herein.

The present invention is directed to a medical device, which can be a suction device, such as a Yankauer suction device. The exemplary embodiments described below are directed to an illuminated suction device that has an improved illumination assembly and other features, such as heat dissipation, lens sealing, etc. It is understood that the features described below with respect to the illuminated suction device may also be applied to other medical devices. For example, the illumination assembly and heat dissipation features described below may be used in other medical devices, such as retractors, laryngoscopes, electrocautery devices, speculums, and other medical devices that use illumination and/or that have components that produce heat.

The illuminated suction device of the present invention provides a reasonably uniform field of illuminance over a 40-mm-diameter area on a target surface approximately normal to a surgical suction tube and with said target surface in contact with or nearby the distal tip of said suction tube. In some embodiments described below, the illuminated suction device has an illumination assembly that provides the reasonably uniform field of illuminance by means of one or more LED light sources mounted adjacent to the suction tube, along with optical elements designed to shape and distribute the visible light emitted from the LED light sources, with the optical elements also being mounted adjacent to said suction tube. Flow control assemblies that may be used in the suction device or other medical devices incorporating suction are also described below.

The suction device described below includes a suction tube having a proximal end configured to be connected via flexible tubing to a source of suction (for example, a vacuum pump) and a distal end fitted with any of a variety of tips designed to provide suitable suction action during a surgical procedure. The suction device may also include a suitable controller for controlling the suction flow and/or suction pressure.

The suction device described below further includes a source of electrical energy, typically one or more primary storage batteries, along with an electrical circuit designed to make use of the stored electrical energy to operate the one or more LED light sources, with a suitable switch/control member to control the on-off condition of, as well as the relative brightness of, the LED light source(s). The electrical circuit is typically designed to provide from two to five hours of operational time of the LED light source(s) from the energy stored in said batteries, but may be modified to provide longer or shorter operational times.

In the present invention, the aforementioned optical elements, to be described in more detail below, form an important aspect of this invention due to their role in efficiently shaping and directing the light emitted from the LED light source(s) so as to maximize the illumination level within the 40-mm-diameter area on the target surface for a given level of LED power consumption.

Another important aspect of this invention involves the size, shape, and locations of the optical elements' emitting apertures. These details of the apertures have been designed to minimize shadows cast by the suction tube, while also minimizing obscuration of the surgeon's field of view. In certain embodiments described below, this goal is achieved by locating these apertures somewhere other than at the top of the suction tube, i.e., somewhere other than at the 12 o'clock position, and keeping them within a reasonable diameter circular area, while maximizing the portion of emitted light that is transmitted through the outermost zones of the apertures. In other embodiments described below, some of the apertures may be located at locations other than the top of the suction tube, while having one of the apertures present at the top of the suction tube.

At the same time, the present invention burdens its optical design with the goal of producing a reasonably uniform field of illuminance at the target surface, with a diameter of approximately 40 millimeters. In one exemplary configuration, the suction device described below makes use of one or more optical elements, including a faceted concave reflector and/or a lens, with the one or more optical elements being so disposed as to shape the emitted light from an LED light source. In one exemplary configuration, the suction device uses both the faceted concave reflector and a lens for directing and shaping the light from each LED light source, while in other exemplary configurations, the suction device may use either the lens or the reflector for shaping and directing the light from each LED light source. In one exemplary configuration described below, the device includes two symmetrical light source channels, each including a light source, e.g., an LED, a faceted concave reflector, and a lens, with the two light source channels being symmetric about the vertical medial plane of the suction tube.

As mentioned above and described in more detail below, the present invention further includes heat dissipation features which allow for use of multiple light sources having improved brightness for longer periods of operating time without heating the device. These heat dissipation features improve patient safety and avoid the possibility of damaging patient tissues by heat generated by the illumination assembly.

The above and other features of the invention are described in more detail below.

FIGS. 1A-1G show different views of an illustrative embodiment of the suction device 100 of the present invention. The suction device includes an outer housing, comprising a body 1, a spine 2, a battery door 10 and a rear cap 6, a suction tube 13 extending within the outer housing and having a distal end extending outside of the outer housing, and an illumination assembly comprising one or more direct light sources (not visible) and one or more optical elements.

The body 1 of the outer housing forms a partial enclosure of the suction device, and in this illustrative embodiment, the body 1 includes an open proximal end 1a, which is covered by the rear cap 6, an open distal 1b end which accommodates the illumination assembly and through which the suction tube 13 extends, and an open top, which is covered by the spine 2 and the battery door 10. In certain embodiments, the body 1, the spine 2, the battery door 10 and the rear cap 6 interlock with one another, and/or are welded to one another, so as to provide fluid-tight construction. In other embodiments, the spine and one or more optical elements, such as the lens, are coupled with one another so as to provide fluid-tight construction, especially at the distal end of the body 1. As shown in FIGS. 1A-1G, the rear cap 6 includes a suction port 6a which can be connected to a vacuum source to provide suction. In some embodiments, the body 1, the spine 2, the battery door 10 and the rear cap 6 of the outer housing are formed from plastic or polymer materials, such as cyclic olefin copolymers (COC), aliphatic polyamides (PA, e.g., Nylon), polycarbonates (PC, e.g., Lexan), polymethyl methacrylate (PMMA aka Acrylic), acrylonitrile butadiene styrene (ABS), or polystyrene (PS). In other embodiments, other materials, including metallic materials, may be used for the outer housing components. The configuration of the outer housing in FIGS. 1A-1G is illustrative and is configured to allow for easy assembly of the internal components of the suction device 100. However, in other embodiments, the outer housing may be formed as a single piece or may combine some of the components of the outer housing in the present embodiment.

The suction tube 13 extends through the entire length of the body 1 and a distal portion of the suction tube 13 extends outwardly from the distal end 1b of the body 1. A proximal end (not visible) of the suction tube 13 is fluidly coupled to the vacuum port 6a in the rear cap 6. The distal end of the suction tube 13 is adapted to have one or more suction tips 13b attach thereto and the suction tips may be interchangeable. In certain embodiments, the suction tube 13 is formed from a metallic material, such as stainless steel, while in other embodiments, the suction tube 13 may be made from plastic or polymer materials, such as cyclic olefin copolymers (COC), aliphatic polyamides (PA, e.g., Nylon), polycarbonates (PC, e.g., Lexan), polymethyl methacrylate (PMMA aka Acrylic), acrylonitrile butadiene styrene (ABS), or polystyrene (PS).

As mentioned herein above, the suction device 100 includes the illumination assembly for providing illumination to the target surface. The illumination assembly includes one or more direct light sources (not visible in FIGS. 1A-1G), such as LEDs, one or more power sources housed within the outer housing and one or more optical elements for directing and/or shaping light emitted from the one or more direct light sources. As shown in FIG. 1A-1G, the one or more light sources and one or more optical elements of the illumination assembly are offset from the distal tip of the suction tube 13 by a predetermined distance. This predetermined distance may vary, but in some embodiments, the distance is around 2.0-2.5 inches from the distal tip of the suction tube 13. In the illustrative embodiment of FIGS. 1A-1G, the one or more power sources are located adjacent the battery door 10 near the proximal end of the outer housing and can be removed from the outer housing by opening the battery door 10. The battery door 10 also includes an opening for inserting a push-tab 14 of a push-tab assembly, which is used to control whether or not the illumination assembly can be turned ON by electrically disconnecting the power source(s) from circuitry of the illumination assembly in a "storage" configuration and by electrically connecting the power source(s) to the circuitry of the illumination assembly to close the circuit in a "use" configuration. The push-tab assembly also assists in removing the one or more power sources from the outer housing without requiring physical contact of the user with the one or more power sources by hooking around a portion of the one or more power sources, or otherwise physically engaging with the power source(s), when the one or more power sources are housed in the outer housing and causing the one or more power sources to be removed from the outer housing when the battery cover 10 is opened. The details of the push-tab 14 and of the push-tab assembly and how it interacts with the electrical components of the illumination assembly and the power source(s) are described in U.S. Pat. No. 10,512,519, assigned to the same assignee herein and incorporated herein by reference.

In the present illustrative embodiment, the optical elements include one or more concave reflectors 4 (not visible in FIGS. 1A-1G but shown in FIG. 2B and FIGS. 2F-2H) and one or more lenses 3, and these optical elements are used for directing and shaping the light emitted from the direct light sources. As described in more detail below, in one illustrative configuration, each light source is located adjacent to the side of the suction tube 13, with exemplary positions being at a 3 o'clock position and a 9 o'clock position with the top of the suction tube 13 being a 12 o'clock position. In addition, the light sources emit light radially with respect to the central axis of the suction tube, i.e., in a direction away from the suction tube 13. In this configuration, the concave reflectors direct the light emitted from the light sources toward the lenses 3, which shape the light so as to provide a uniform field of illuminance over a predetermined area, e.g., an area of 40 mm, on the target surface.

As described in more detail below, in some embodiments, the optical elements may include only the reflectors or only the lenses. In addition, in some embodiments, particularly the embodiments without reflectors, the light sources are oriented so as to emit light in a direction toward the distal tip of the suction tube 13. Exemplary configurations of such embodiments will be described in more detail below.

Figure 1E:
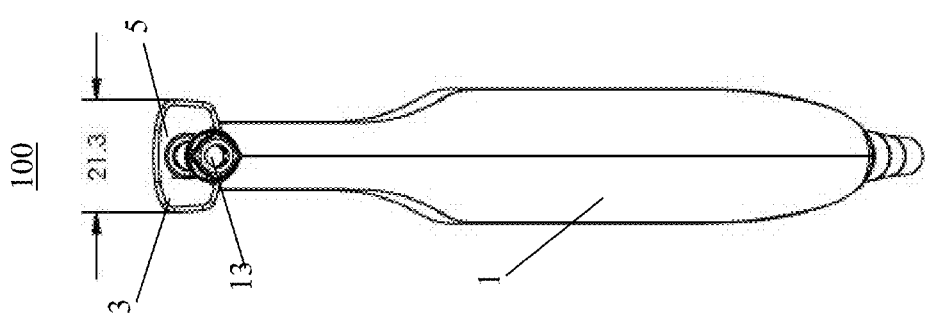

As described in more detail below, the interface between the suction tube 13 and the lenses 3 may be sealed using a sealing assembly. As shown in FIGS. 1A and 1E, a gasket 5 is used for sealing the space or interface between the suction tube 13 and the lenses 3. The sealing provides a fluid tight environment within the distal end of the outer housing and within the illumination assembly and prevents fluids from entering behind the lens and from entering the reflector 4.

The illumination assembly also includes a switch 11 or a similar operating member for controlling the ON/OFF state of the illumination assembly and in some embodiments, for also controlling the brightness and/or color of the light source(s). In the illustrative embodiment of FIGS. 1A-1G, the switch 11 is a button lever provided within a recess 11a in the spine 2. In other embodiments, the switch 11 is a slider, which moves or slides within the recess 11a from an OFF position at one end of the recess 11a to an ON position and the brightness of the light source(s) is controlled to increase as the lever slides in a direction of the other end of the recess. Other types of switches, such as a potentiometer switch described in U.S. Pat. No. 10,512,519, may be used for the illumination assembly of the present invention. As shown in FIGS. 1A-1G, the switch is provided in the spine 2 of the outer housing. However, the position of the switch 11 is not limited to the one shown and may instead be provided in other areas of the outer housing, including in the body 1 or in the rear cap 6.

The configurations of the illumination assembly described in more detail below are aimed at providing illumination with uniform brightness to the target area, while eliminating shadows. The configurations of the illumination assembly described below also aim to achieve this improved illumination without a significant increase in the size of the suction device so that the device itself and its illumination assembly do not obscure the user's view of the operating site and so that the suction device can be inserted into small incisions. FIGS. 1C-1E show exemplary dimensions of the suction device 100 of the present invention. As shown in FIG. 1D, the exemplary length of the suction device 100 is around 329 mm from the tip of the suction tube to the end of the port 6a, and the exemplary height of the outer housing at the proximal end 1a of the body 1 is about 37 mm. As shown in FIG. 1E, the exemplary width of the body 1 at the distal end 1b where the light source(s) and optical elements are housed is about 21.3 mm. Although not shown, the suction tube has an exemplary inside diameter of about 4.5 mm to minimize clogs and an outer diameter of about 5.5 mm. In certain embodiments, the inner and outer diameter of the suction tube 13 remains substantially uniform throughout its length, while in other embodiments, the diameter may change, such as to accommodate a flow control assembly or to provide sealing to the lens. The LEDs in this illustrative example are about 1.6 mm wide. However, smaller or larger LEDs may be used depending on the size restrictions of the suction device.

FIGS. 2A-2D and FIGS. 2E-2I show in more detail the configurations of the distal end 1b of the body and the optical elements of the illumination assembly in the suction device. In FIGS. 2E-2I, the configuration of the illumination assembly of the suction device of FIGS. 1A-1G is shown, while in FIGS. 2A-2D, a modified configuration of the illumination assembly is shown. Similar numbering is used for the same or similar components of the illumination assembly.

Figure 2C:
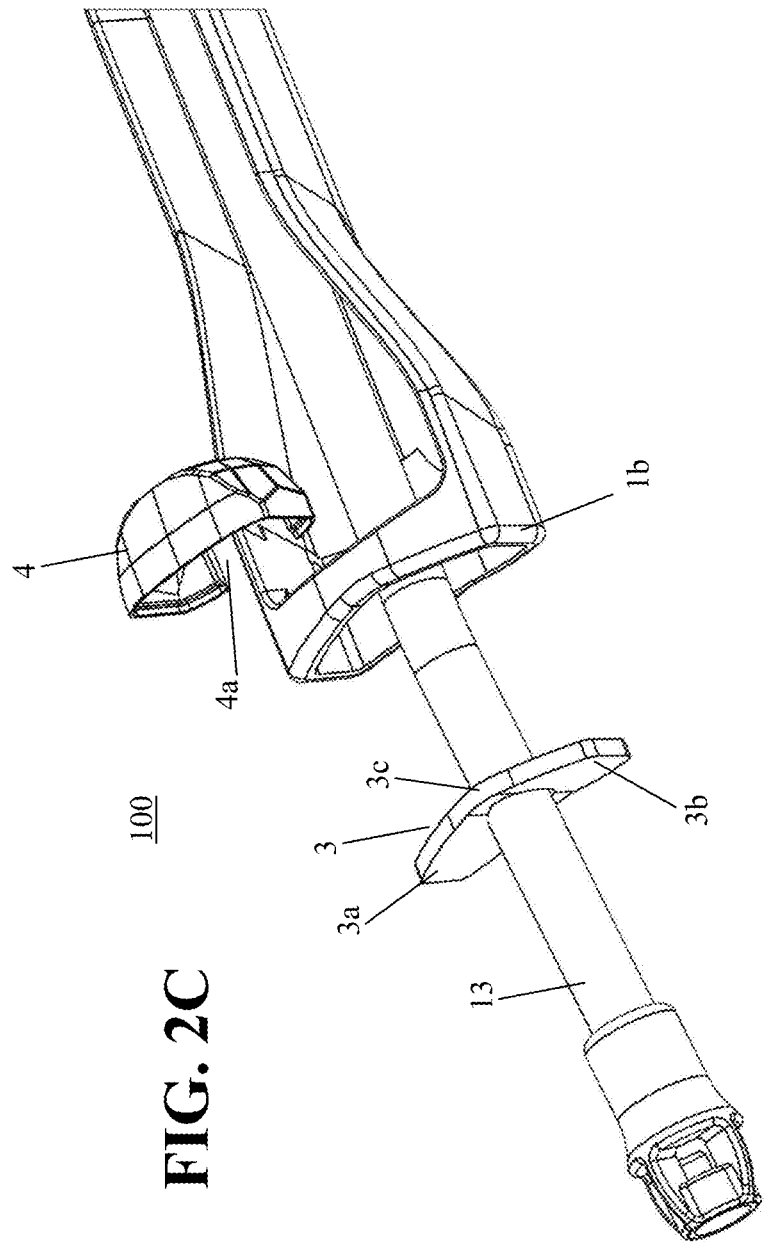
FIG. 2C shows the distal end of the suction device of FIG. 2A with an exploded view of the illumination assembly.
Figure 2D:
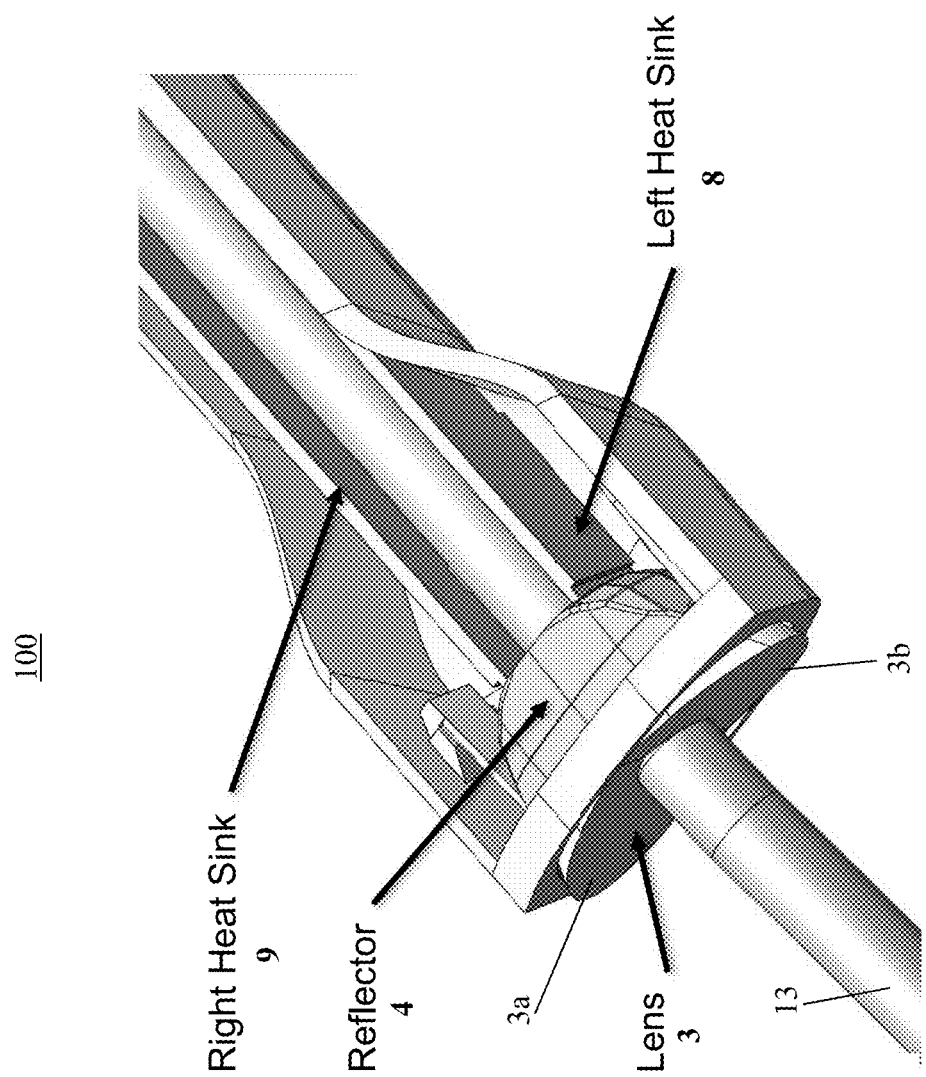
FIG. 2D shows another view of a portion of the suction device with the illumination assembly and other components exposed.
Figure 2E:
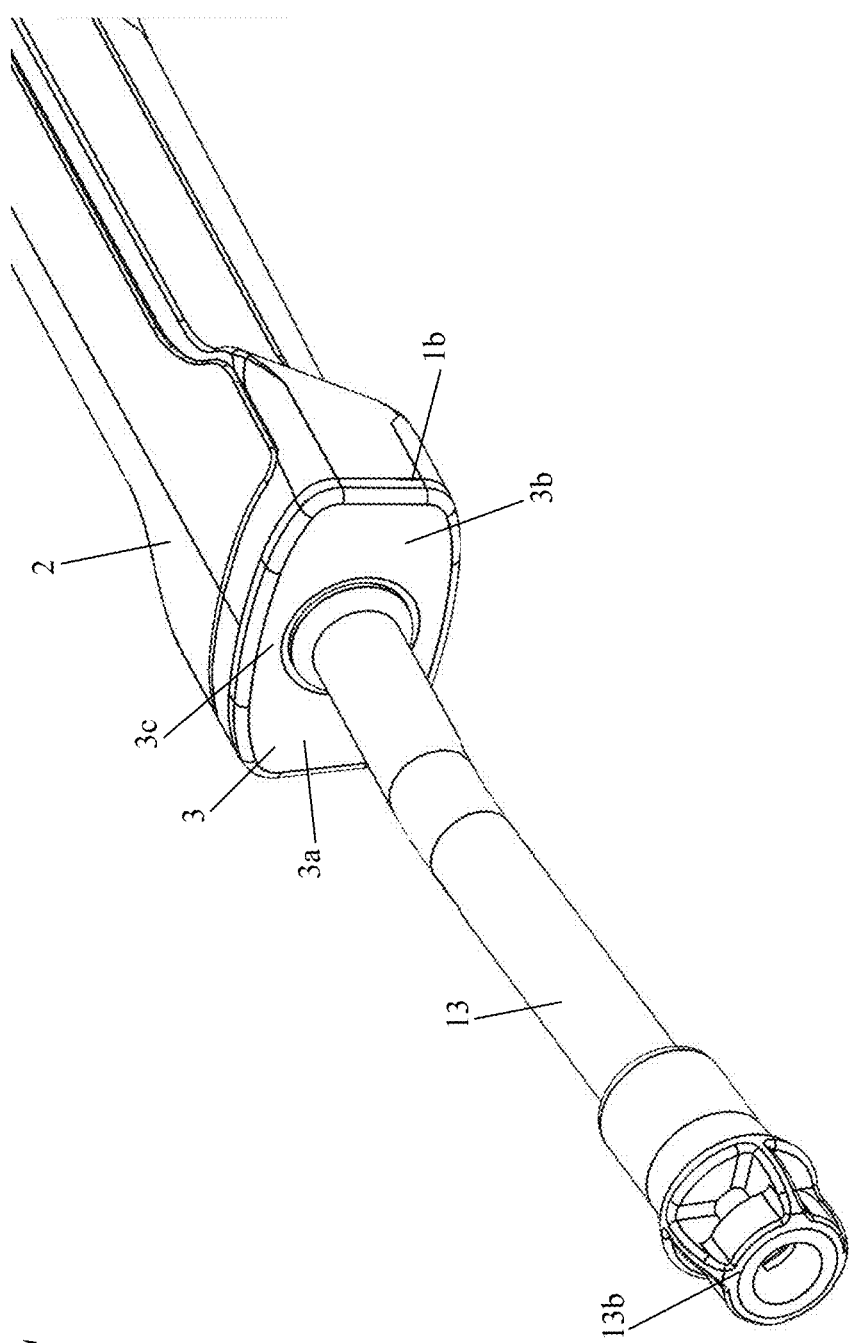
FIG. 2E shows a close-up view of a distal end of the suction device of FIGS. 1A-1G.
Figure 2G:
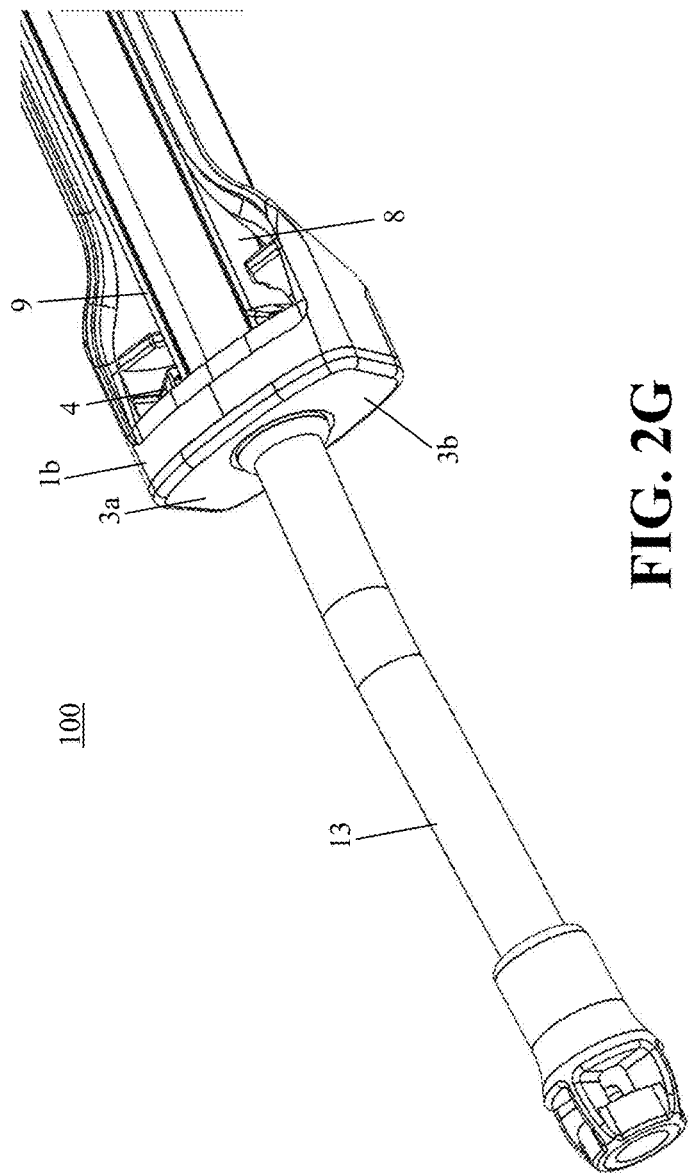
FIGS. 2F and 2G show the distal end of the suction device of FIG. 2E with a top cover/spine removed to expose the illumination assembly.
Figure 2F:
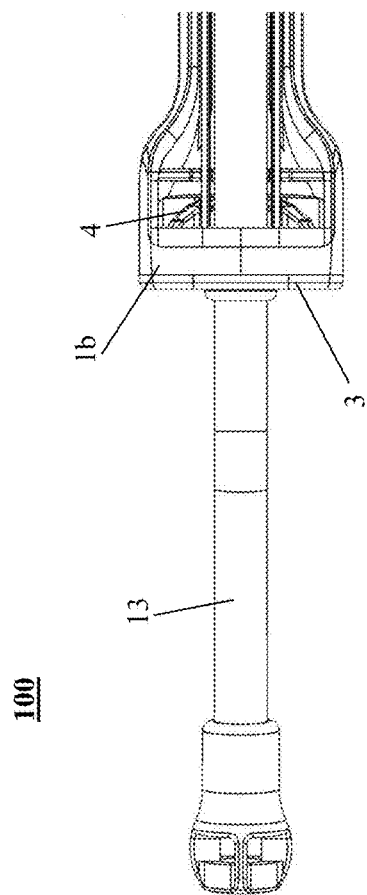
Figure 3B:
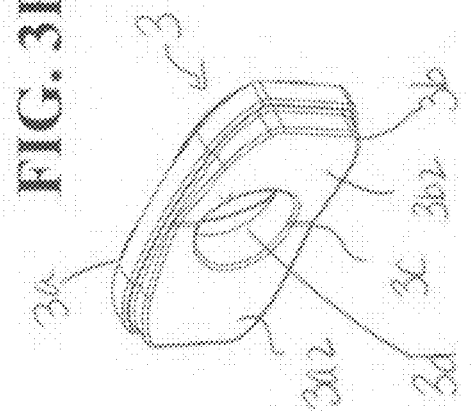
FIGS. 3A-3D show different views of an exemplary lens of the illumination assembly.
Figure 3D:
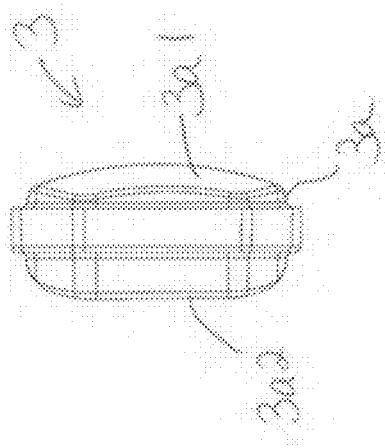
Figure 3A:
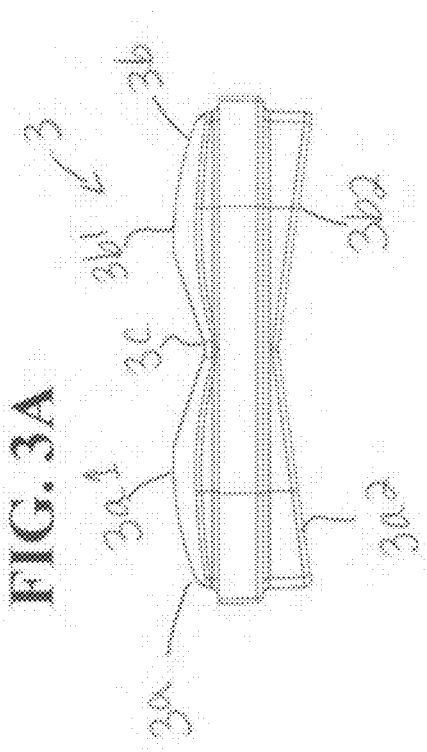
Figure 3C:
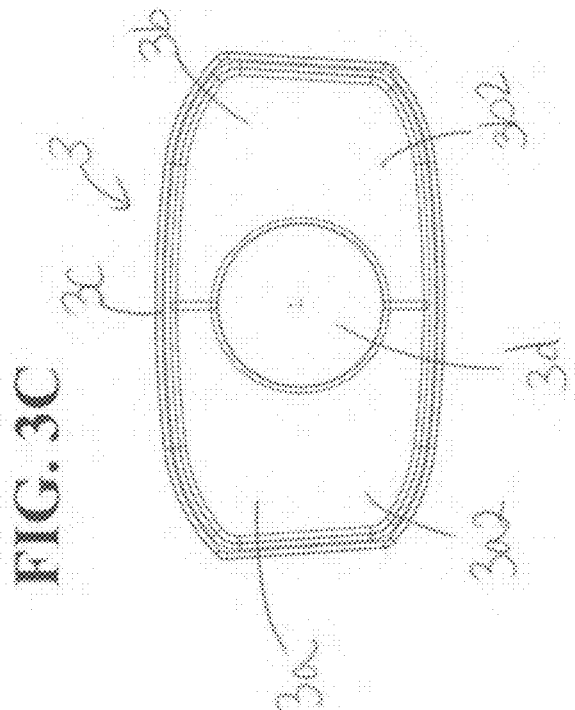
Figure 3F:
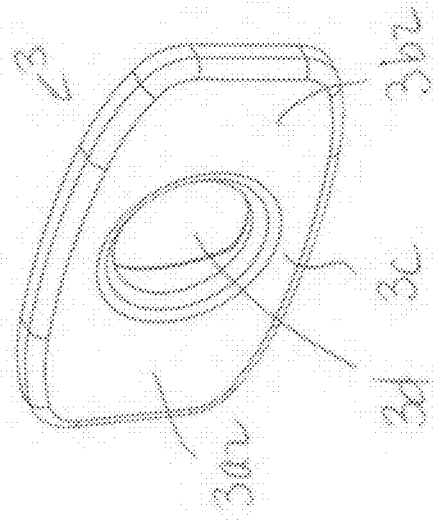
FIGS. 3E-3H show different views of another exemplary lens of the illumination assembly.
Figure 3H:
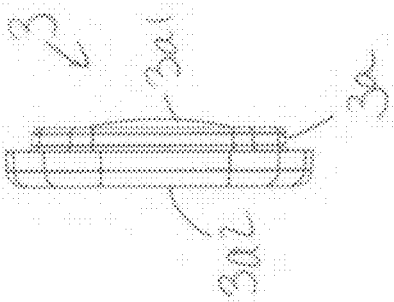
Figure 3E:
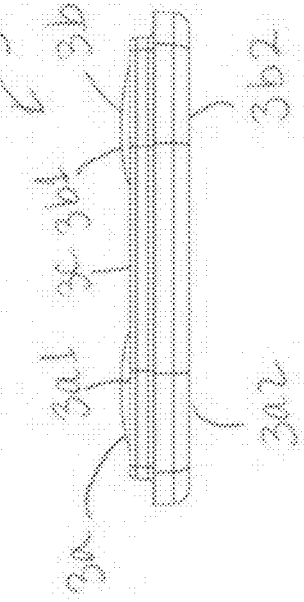
Figure 3G:
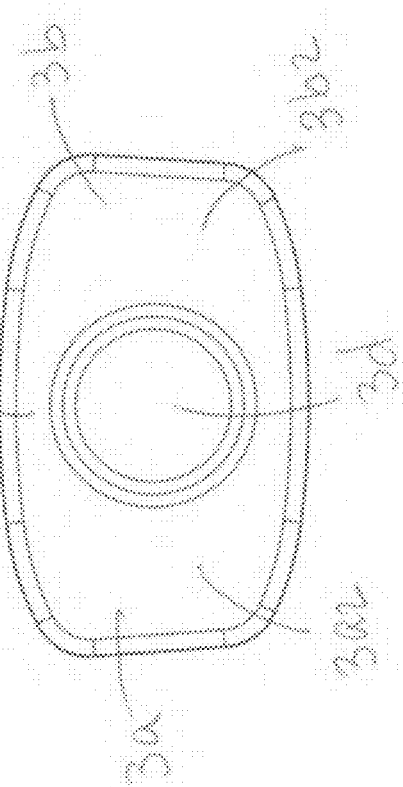

FIGS. 2A and 2E show the distal end 1b of the body 1 in an assembled state, FIGS. 2B, 2F and 2G show the distal end 1b with the spine 2 taken off to expose an internal assembled configuration of the distal end 1b, and FIGS. 2C and 2H shows an exploded view of the optical elements, i.e., the reflector 4 and the lens 3 in the distal end 1b of the body 1. FIG. 2D shows an additional view of the distal end 1b of the body with the spine 2 removed to expose the internal assembled configuration with a heat sinking assembly and FIG. 2I shows an additional view of FIG. 2H with the heat sinking assembly removed from the illumination assembly. As shown in FIGS. 2A-2D and FIGS. 2E-2I, the suction tube 13 extends through the length of the body 1 and passes through the lens 3 or between multiple lenses 3 of the illumination assembly to extend from the distal end 1b of the body 1.

In the illustrative embodiment of FIGS. 2A-2D, the illumination assembly includes a pair of light sources (not visible), such as LEDs, each of which is positioned adjacent to a side of the suction tube 13, with a top of the suction tube 13 being covered by the spine 2. The light sources are arranged so that each light source emits light radially relative to the central axis of the suction tube 13, i.e., in a direction away from the surface of the suction tube 13. In other embodiments, multiple light sources instead of a single light source may be used at each location adjacent to the suction tube 13. As shown in FIGS. 2B-2D, the optical elements of the illumination assembly include a reflector 4 and a lens 3 that includes lens portions corresponding to each light source or to each set of light sources, with the lens portions being coupled to one another via a bridge.

The reflector 4 is a concave multi-faceted reflector with a reflective surface on its concave surface. The reflector 4 is positioned so as to partially surround the light sources adjacent to the sides of the suction tube 13 and to reflect light emitted from the light sources toward the corresponding lens portions of the lens 3. The reflector 4 may be a portion of a paraboloid, a segmented approximation of a portion of a paraboloid, or a collection of specifically determined facets whose geometry has been optimized to maximally and uniformly illuminate the desired area of the target surface. In the illustrative embodiment of FIG. 2C, the reflector has an elongated, substantially ovular or rectangular shape, and includes a recess or cutout 4a therein for positioning the reflector 4 over and around the suction tube 13. When the reflector 4 is positioned over and around the suction tube 13, the suction tube 13 passes through the cutout 4a, and each light source is partially enclosed within the concave space of the reflector so that light emitted from the light sources is directed toward the reflector 4.

Figure 5B:
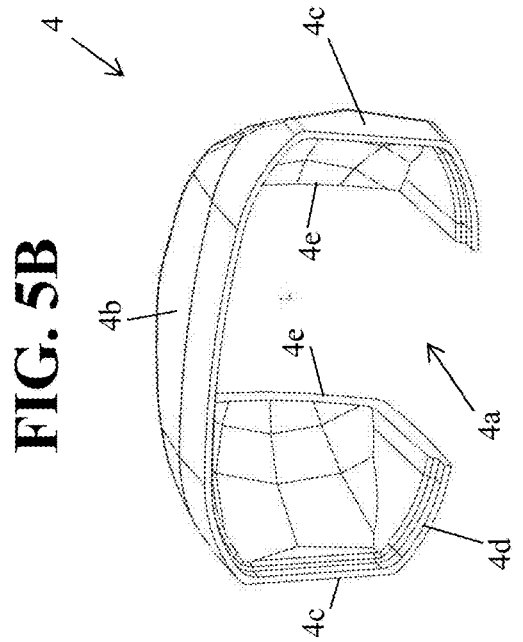
FIGS. 5A-5D show different views of an exemplary reflector of the illumination assembly used in FIGS. 2A-2D.
Figure 5D:
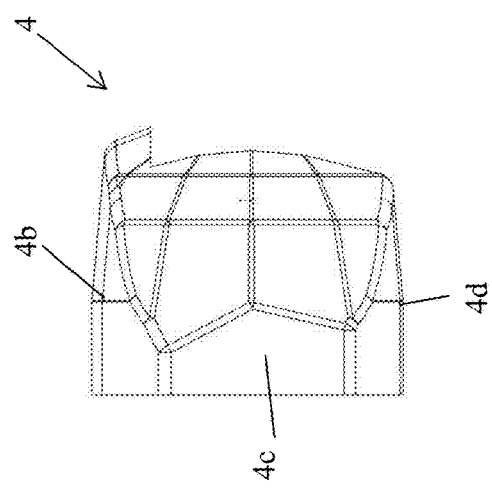
Figure 5A:
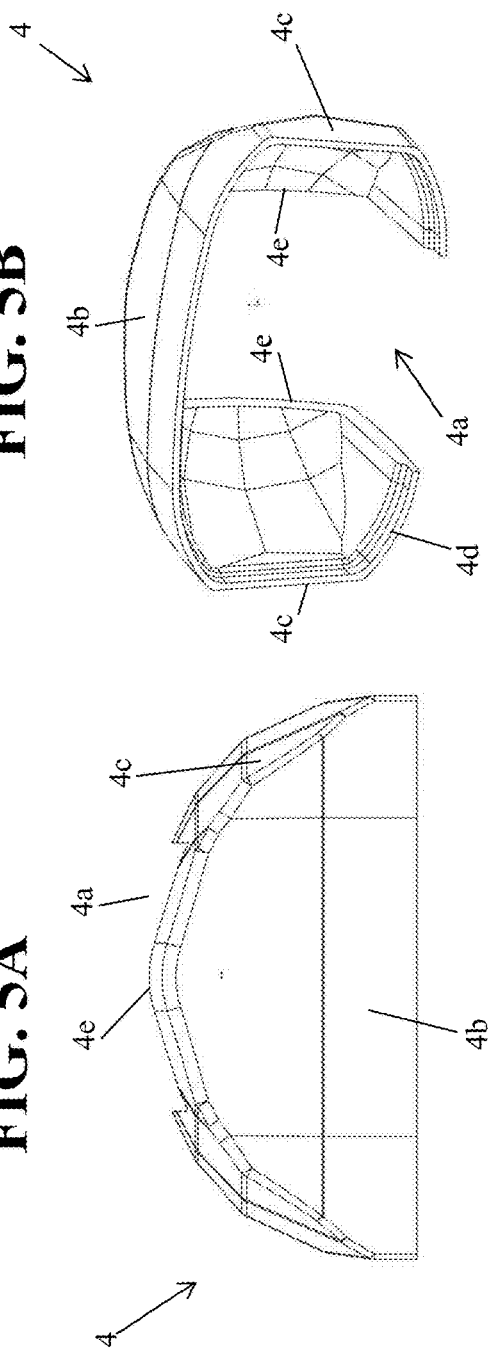
Figure 5C:
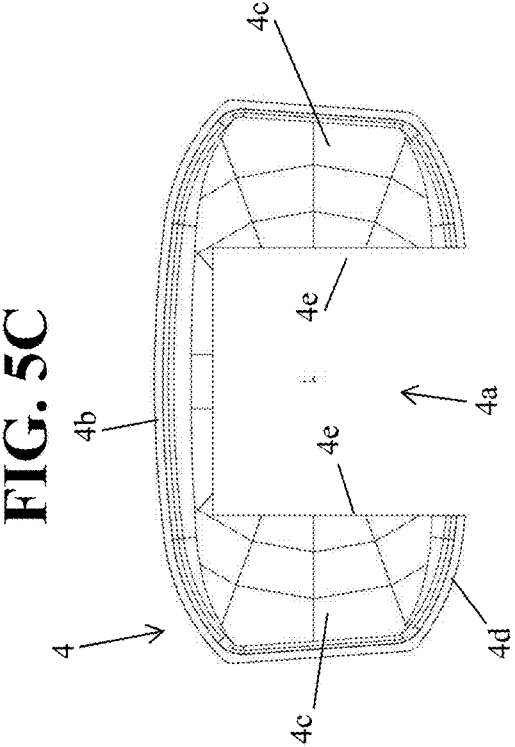
Figure 5E:
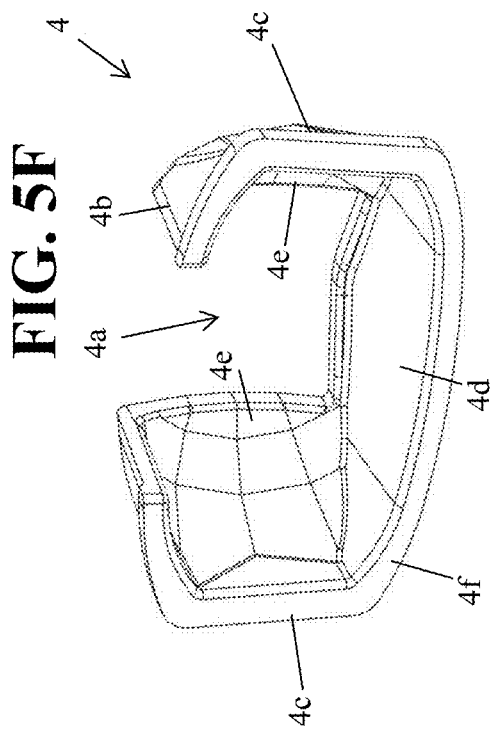
FIGS. 5E-5H show different views of another exemplary reflector of the illumination assembly used in FIGS. 2E-2I.
Figure 5F:
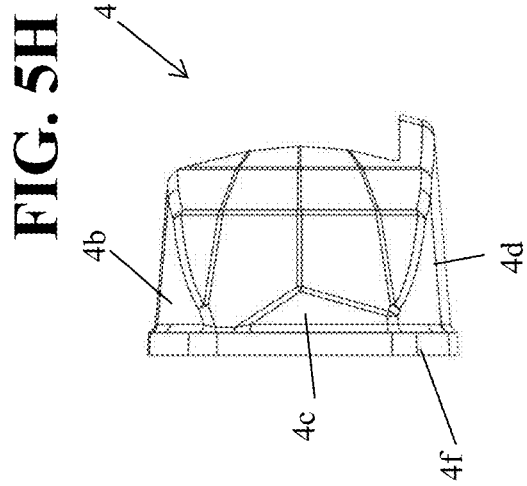
Figure 5G:
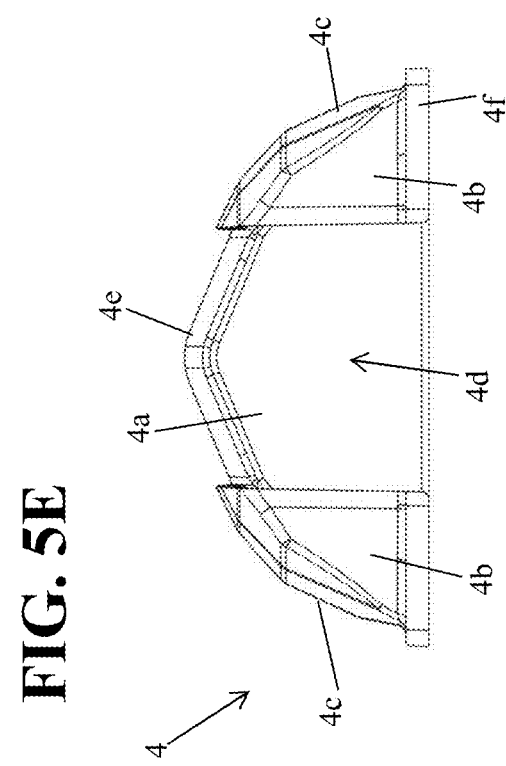
Figure 5H:
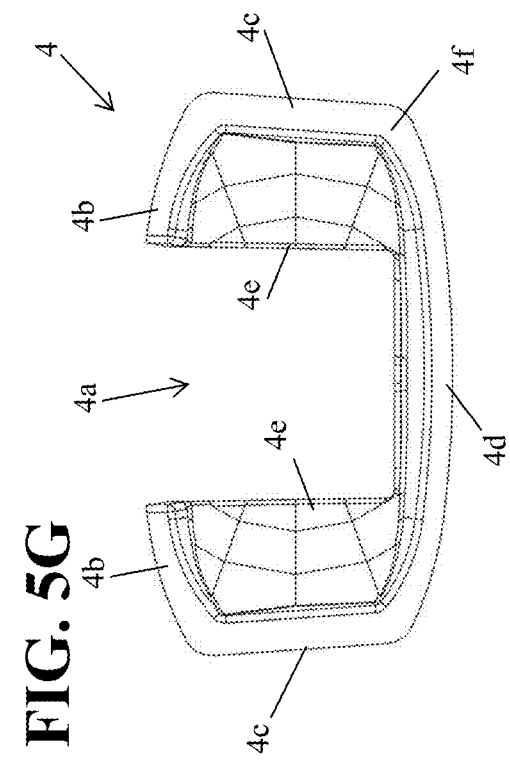

FIGS. 5A-5D show more detailed views of the reflector 4 of FIGS. 2A-2D, including a top view (FIG. 5A), a perspective front view (FIG. 5B), a front view (FIG. 5C) and a side view (FIG. 5D). As shown in FIGS. 5A-5D, the reflector includes a flattened top wall 4b, concave sidewalls 4c on each side so as to enclose the light sources, a partial flattened bottom wall 4d and a partial concave back wall 4e. The reflector 4 has the recess or a cutout 4a in the bottom 4d and back 4e walls, with the recess or cutout 4a being shaped and sized so that the reflector 4 can be easily positioned over and around the suction tube 13 without affecting its reflecting characteristics. As shown in FIGS. 5A-5D, the walls 4b-4e of the reflector each have multiple facets, particularly the side walls 4c and the back wall 4e, which have reflecting angles and characteristics customized so as to direct the light beams emitted from the light sources toward the corresponding lens portions of the lens 3 and to shape the light beams in order to achieve uniform illumination in the target area.

As will be recognized by one skilled in the art, the detailed geometric design of the reflective surface(s) of an optical reflector (hereinafter referred to as "the reflector design") such as this may be optimized, by itself or in conjunction with a lens (such as lens 3 in FIG. 2D), in order to maximize two important characteristics of the overall illumination assembly: 1) the uniformity of illuminance falling upon the target area; and 2) the total luminous flux falling within the target area. The target area is defined, as above, as a 40 mm diameter circular area on a planar surface in contact with or nearby the distal tip of suction tube 13 and approximately normal to the axis of the tube where it passes through the reflector.

In some embodiments, the reflector design is optimized using commercially available optical design software, such as Zemax OpticStudio. Such software allows the user to define the geometry of the reflector and then to trace a large number of rays from a light source to a target surface, following which the uniformity of illuminance and total luminous flux within the target area may be evaluated. By making changes to said geometry, re-running a ray trace, and then re-evaluating the uniformity and total flux, the user can gradually improve the theoretical performance of the geometry until satisfactory results are achieved.

In some embodiments the reflector design approximates a paraboloid, which has the inherent property that rays emanating from a single point (the focus of the paraboloid) emerge collimated after reflection. In some embodiments it is desirable to approximate a paraboloid by means of multiple flat facets for the purpose of "homogenizing" the light, meaning to combine or overlap multiple sets of rays, each of which sets may produce a non-uniform illuminance pattern at the target, such that the combined total illuminance is more uniform.

In some embodiments the initial reflector design is arrived at via the following logic:

1. Start with a point light source located at the center of the emitting surface of the LED 15 (FIG. 12D) or other light source, with emission characteristics defined to approximate the measured or specified luminous intensity of the light source as a function of ray angle from the axis of the light source (note that generally the luminous intensity of an LED is not variable with polar angle; i.e., an LED's luminous intensity pattern is circularly symmetric). FIGS. 12E and 12F show a typical small high-intensity LED and a graph of its luminous intensity as a function of emittance angle. If the light source is other than an LED, its particular emittance characteristics should be used.

2. Define a paraboloidal surface such that the focus of the paraboloid is at said point light source, and such that the focal length of the paraboloid is chosen as follows:

2.1. Choose the portion of the full solid angle of emission of the light source that will be intercepted by the reflector. As shown in FIG. 12F, capturing emission within an emittance angle range of 0° to 60°, for example, will make use of a major portion of the total emission from an LED, as the luminous intensity is substantially decreased beyond 60°.

2.2. Truncate the paraboloidal surface to that portion that intercepts the selected portion of the light source's emission solid angle.

2.3. Measure the distance from the device axis (i.e., the axis of the suction tube 13 where it passes through the reflector) to the farthest point on the truncated paraboloidal surface.

2.4. Vary the paraboloid focal length until said measured distance is the desired maximum radial size of the device aperture. In this embodiment, the radial size of the aperture was limited to about 9 mm in order to limit the device package width to around 22 mm. This relationship will vary, of course, depending on the design details of any housing surrounding the reflector aperture.

3. Replace said defined paraboloidal surface with a set of planar facets that lie approximately on the paraboloidal surface, i.e., each facet being tangent to said surface at a point near the center of the facet. Define the extents of said facets as follows:

3.1. Set a minimum bound for the facet dimensions based on the manufacturing technology to be employed. For example, practical injection molding tooling is often limited to features larger than 1 mm in extent.

3.2. Set a minimum bound for the total number of facets based on the desire for effective homogenization as well as the allowable angular deviation of any given facet from the theoretical underlying paraboloidal surface. For example, having too few facets will fail to provide adequate homogenization of the light source's emission; and having facets that are too large will reflect some light rays at an angle that deviates excessively from the angle that would be reflected by the ideal paraboloid.

3.3. Arrange the facets and their extents so that the solid angle subtended by the light rays intercepted by each facet is roughly equal for all facets. This implies facets located farther away from the point source should be larger than facets located closer to the point source.

4. Finally, fine-tune the tilt angles of the facets in order to produce acceptable results in terms of illuminance uniformity and total luminous flux across the target area.

It will be understood by one skilled in the art that there is interaction between all the design parameter choices listed in the logical steps 1 to 4 above. For example, limiting the radial extent of the device, and hence of the reflector aperture, will result in a larger fraction of the rays emitted by the reflector to be blocked by the suction tube. Also, setting a larger angular range to capture a larger fraction of the light source's emission will tend to decrease the resulting focal length of the paraboloid, leading again to more blocked rays.

In following the design logic for some embodiments, the point source defined in step 1 above may be replaced by a finite source object with dimensions approximating the actual emitting surface of the chosen light source. Similarly, in some embodiments, the design process using optical software may make use of actual measured emittance data from a light source manufacturer, which can be specified as a database of rays to be launched from the source object position during a ray trace.

It should be emphasized that in some embodiments the reflector design may not begin with or approximate a paraboloid. Indeed, any free-form collection of planar or non-planar facets, which combine to form a reflector that intercepts a significant fraction of the light source's emission, may be employed as a starting point for the reflector design. Similarly, any method, whether using simulation software on a computer or using physical trial and error, may be employed to vary the reflector design and to arrive at a satisfactory design solution.

In some embodiments, the presence of lens 3 adds another set of variables into the overall optical design, such that the total optical design of reflector plus lens may be optimized using optical ray tracing software or other methods.

Referring back to FIGS. 2A-2D, the lens 3 is disposed adjacent the distal edge of the body 1 and is positioned so as to cover the opening in the distal end 1b of the body and adjacent the front open end of the reflector 4. In some embodiments, the lens 3 may be positioned so as to cover the front open concave end of the reflector 4, while in other embodiments, the reflector 4 may be positioned further away from the lens 3. As shown, the lens 3 in the present illustrative embodiment includes two lens portions 3a, 3b, each of which corresponds to the respective light source or set of light sources, and the lens portions 3a, 3b are connected to one another by a bridge 3c so as to form a single lens unit. The lens 3 also includes a through opening 3d in the bridge 3c that accommodates the suction tube 13 extending from the body 1 of the suction device. This configuration of the lens 3 contributes to the fluid tight configuration of the outer housing and eliminates the need for additional lens holding members. In other embodiments, however, a separate lens may be used for each light source or set of light sources and in some embodiments, an additional lens holder may be included for positioning the lenses adjacent the distal end 1b of the body 1 and for providing fluid sealing to the outer housing.

Figure 4:
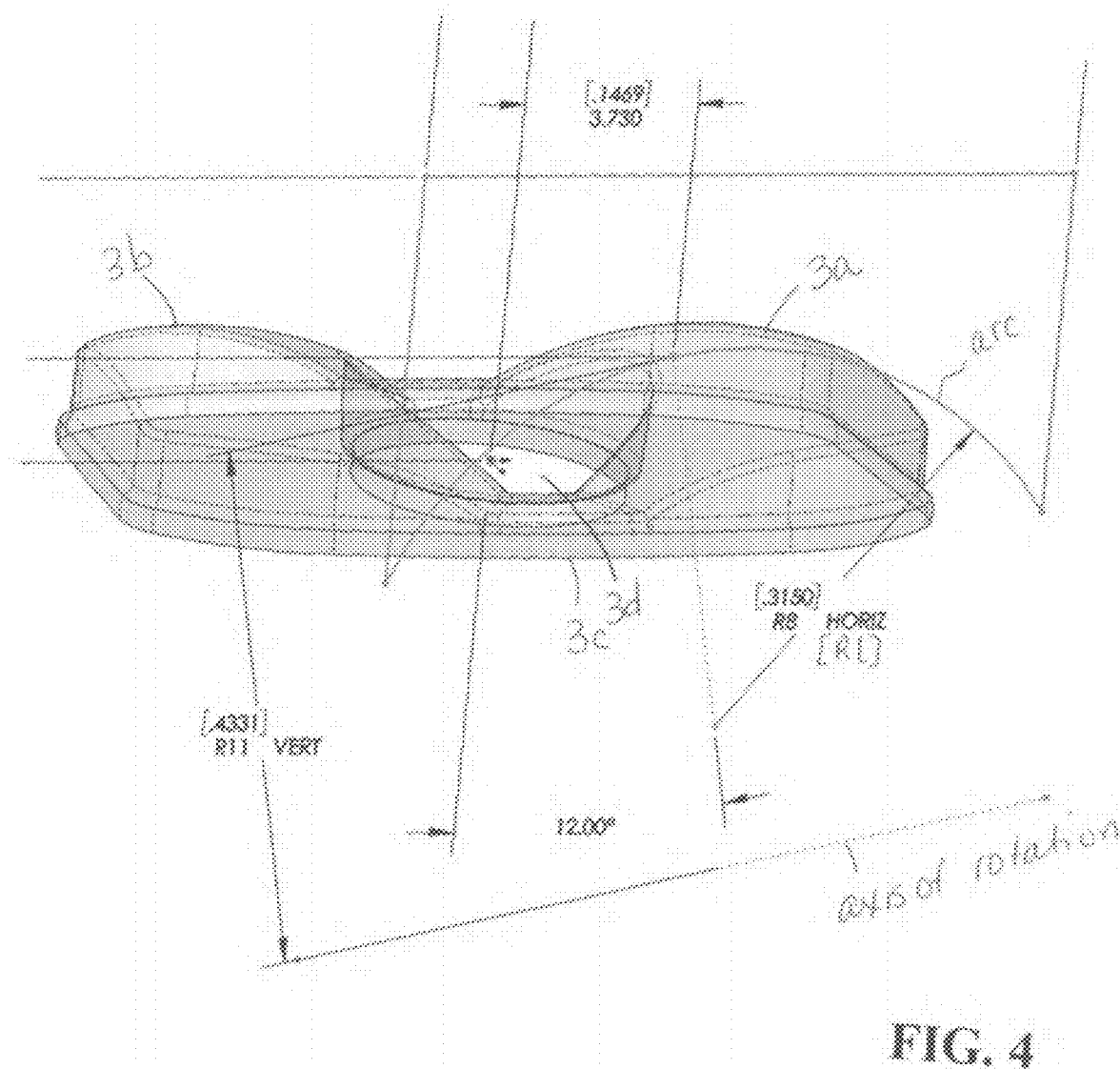
FIG. 4 shows another exemplary lens of the illumination assembly.

FIGS. 3A-3D and 4 show exemplary configurations of the lens 3 that can be used in the illumination assembly of FIGS. 2A-2D. FIGS. 3A-3D show top, perspective, front and side views of a first embodiment of the lens, and FIG. 4 shows a perspective view of a second embodiment of the lens. The lens 3 is formed from a transparent material, and may be molded from a transparent plastic, polymer or glass material. As shown in FIGS. 3A-3D, the lens 3 is includes two lens portions 3a, 3b connected by the bridge 3c, with each lens portion corresponding to one of the light sources or one of the sets of light sources. The bridge 3c does not participate in directing light. Each lens portion 3a, 3b may be fabricated separately and then joined, or the entire lens 3 may be fabricated as a single lens unit.

As shown, each lens portion 3a, 3b is a plano-convex lens, and in particular a plano-convex aspherical lens that includes a convex surface 3a1, 3b1 and a planar surface 3a2, 3b2. When assembled into the suction device, the convex surfaces 3a1, 3b1 of the lens portions 3a, 3b are light inlet surfaces that face the light sources and the reflector 4, while the planar surfaces 3a2, 3b2 are light output surfaces that face outside of the outer housing. As shown in FIGS. 3A-3D, the lens portions 3a, 3b, and/or the planar surfaces 3a2, 3b2 of the lens portions 3a, 3b, are angled with respect to each other. With this construction, the light directed from each of the planar surfaces 3a2, 3b2 is directed toward the same target area.

FIG. 4 shows a second exemplary embodiment of a lens 3 that can be used in the suction device of FIGS. 2A-2D. The lens 3 in FIG. 4, as in FIGS. 3A-3B, includes two lens portions 3a, 3b connected by a bridge 3c, and is a plano-convex lens. In this embodiment, each lens portion 3a, 3b is a toroidal aspheric lens having two unequal radii. Each lens portion 3a, 3b has a doughnut surface having two different radii and is described by a circular arc of radius R1 revolving around an axis that is located R2 from the farthest point of the arc. In addition, the distance between the center of the arc being swept and the axis around which it is being swept is R2-R1.

In the illustrative embodiment of FIG. 4, in each lens portion 3a, 3b, the radius of the arc R1 is 8 mm (or 0.3150 inches), and R2, which is the distance from the farthest point of the arc to the axis around which the arc is revolving, is 11 mm (or 0.4331 inches). In FIG. 4, the dotted line extending upwardly from the center of the 8 mm arc (R1) is perpendicular to the axis of rotation, which is defined by the lower dotted line dimensioned at 11 mm (R2). In this illustrative embodiment, R2−R1 is 3 mm (0.1181 inches). In FIG. 4, the revolving axis is tilted 12 degrees away from the suction device's overall optical axis, or from the axis of the suction tube. The effect of this tilt is to introduce a "wedge" into the optical path so as to bend the light rays outward. The distance between the optical channel in the lens portion 3a,3b of FIG. 4 to the center of the lens 3 is around 3.730 mm (0.147 inches), and the channel-to-channel distance is 7.46 mm (0.294 inches), which has a meaning similar to the interpupillary distance typically specified for human eyeglasses.

As shown in FIG. 4, the two lens portions 3a, 3b, are joined by two flat bridges of material 3c to form a single molded part. The opening 3d in the center of the lens 3 is formed for accommodating the suction tube 13, and in some embodiments may include sealing features (not shown), such as a pocket for an O-ring or gasket to seal to the suction tube. In addition, the lens 3 may also have a raised peripheral rim (not shown) for mounting the lens or another configuration to assist in mounting the lens.

Depending on the light sources used in the illumination assembly, their positioning and the reflector used or not used in the illumination assembly, the shape of the lens portions 3a, 3b may be modified in order to achieve the desired uniform illumination in the target area of 40 mm diameter or other desired target areas. Alternative types of lenses that are suitable for use in the illumination assembly include other plano-convex lenses, such as plano-convex spherical lenses, bi-convex spherical lenses, meniscus spherical lenses, other types of plano-convex aspherical lenses, bi-convex aspherical lenses, meniscus aspherical lenses, plano-toroidal lenses, bi-toroidal lenses, any combination of two or more of these lenses, and/or any combination of any of these types of lenses with one or more cylindrical lenses.

FIGS. 2E-2I show another configuration of the illumination assembly, which also includes the pair of light sources, such as LEDs, the reflector 4, which is a concave multi-faceted reflector with a reflective concave surface, and the lens 3 disposed adjacent the distal edge of the body and covering the opening in the distal end 1b of the body. As in FIGS. 2A-2D, each of the light sources is positioned adjacent to a side of the suction tube 13 so that each light source emits light radially relative to the central axis of the suction tube 13.

As in FIGS. 2A-2D, the lens 3 of the embodiment in FIGS. 2E-2I includes two lens portions 3a, 3b, each of which corresponds to the respective light source or set of light sources, and the lens portions 3a, 3b are connected to one another by a bridge, forming a single unit. An exemplary configuration of the lens 3 used in the illumination assembly of FIGS. 2E-2I is shown in FIGS. 3E-3H. Although the shape of the lens 3 in FIGS. 3E-3H is somewhat different from the lens of FIGS. 3A-3B, the features thereof are similar to the lenses described herein above. Moreover, the characteristics of the lens 3 in FIGS. 3E-3H are similar to those of the lens shown in FIG. 4 discussed above.

As in FIGS. 2A-2D, the reflector 4 is positioned so as to partially surround the light sources and to reflect light emitted from the light sources towards the lens 3. However, the reflector 4 in the embodiment of FIGS. 2E-2I includes a recess or cutout 4a in the top 4b and back 4e walls, with the cutout 4a being shaped and sized wo that the reflector 4 can be positioned within the distal end 1b of the body 1 and the suction tube 13 can then be inserted into the recess or cutout 4a. Specifically, in the present embodiment, the recess or cutout 4a is provided at the top of the reflector 4, rather than the bottom of the reflector, in order to modify the assembly process of the suction device.

An exemplary reflector 4 is shown in FIGS. 5E-5H, which show the top view (FIG. 5E), a perspective front view (FIG. 5F), a front view (FIG. 5G) and a side view (FIG. 5H) of the reflector. The features and configuration of the reflector in FIGS. 5E-5H is similar to those of the reflector shown in FIGS. 5A-5B, and the principles for designing and customizing the facets and optical characteristics of the reflector 4 of FIGS. 5E-5H are similar to those described above. As discussed above, unlike the reflector of FIGS. 5A-5B, the reflector of the present embodiment has a cutout 4a in the top wall 4b and the back wall 4e to allow the reflector to be assembled into the illumination assembly first before assembling the suction tube 13. In addition, in the embodiment of FIGS. 5E-5H, the reflector 4 includes a lip 4f around the front periphery thereof for positioning and holding the reflector within the distal end 1b of the body.

As discussed above, the illumination assembly of the present invention is configured to project light toward the distal tip of the suction tube and the light sources and optical elements are arranged so as to project a significant portion of the total light emitted by the one or more light sources uniformly into the target area surrounding the distal tip of the suction tube. The present invention also achieves this without substantially increasing the size of the suction device, particularly the size of the distal end 1b of the body 1 of the suction device. There are different specific arrangements of the light sources and optical elements that would satisfy these requirements of the invention, including the arrangement described above with respect to FIGS. 1A-2I and other exemplary arrangements described in more detail below.

Figure 6A:
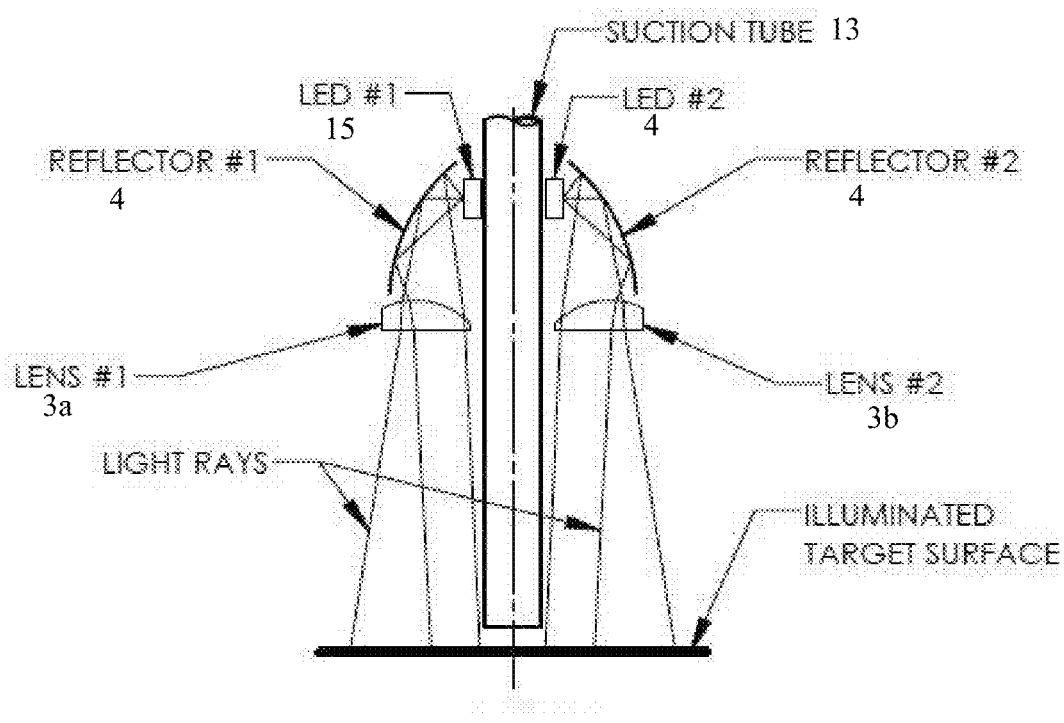
FIGS. 6A-6B show schematic top and front views of a first illustrative arrangement of the illumination assembly.
Figure 6B:
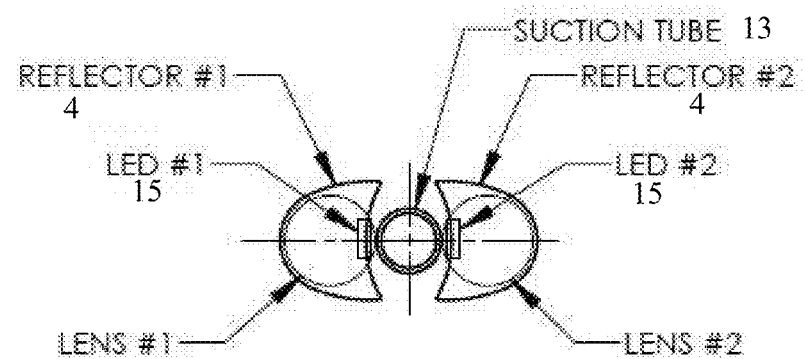

The illustrative configuration of the light sources and optical elements of the illumination assembly described above with respect to FIGS. 1A-2I is shown schematically in FIGS. 6A-6B, wherein FIG. 6A shows a top view of the distal end of the suction device 100 positioned in close proximity to the target surface to be illuminated and FIG. 6B shows a front view thereof, which is viewed from the target surface looking proximally. As shown in FIGS. 6A and 6B, the illumination assembly includes two light sources 15, or two sets of light sources, with each light source 15 positioned adjacent to the side of the suction tube 13 and emitting light radially relative to the central axis of the suction tube 13. Specifically, each light source 15 is positioned with its rear surface, which is opposite to the light-emitting surface, as close as possible to the suction tube 13 while also having an air gap between the light source 15 and the suction tube 13, so that the axis of its cone of emitted light is pointing radially away from the suction tube 13. The air gap between the light source 15 and the suction tube 13 keeps the suction tube thermally isolated from the light sources 15.

The illumination assembly further includes an optical reflector 4, as described above, and a lens having a pair of lens portions, as described above, or having two separate lenses 3a, 3b, as schematically shown in FIGS. 6A and 6B. The reflector 4, or in some embodiments a concave mirror, is positioned so as to intercept a significantly large portion of the light emitted from the light sources 15. As can be seen in FIG. 6A, the light rays emitted from the light sources 15 get intercepted by the reflector 4 and are then redirected, by reflection, so as to pass through the lenses 3a, 3b, each of which is made of a transparent material and has a surface geometry designed to refract the light rays in a manner so as to maximally and uniformly illuminate the target area. The lenses 3a, 3b may have a configuration described above with respect to FIGS. 3A-3H or FIG. 4, or may have a different configuration suitable for directing and shaping the light from the light sources and the reflector 4 to uniformly illuminate the target area. The geometric designs and locations of the reflector 4 and the lenses 3a, 3b, along with the choice of material of the lenses 3a, 3b, work together to direct as much as possible of the light emitted from the light sources 15 into the desired area of the target surface, as well as to spread said light uniformly over the target area.

In the illustrative arrangement of FIGS. 6A and 6B, the two light sources 15 are arranged at approximately 3 o'clock and 9 o'clock angular positions relative to the axis of the suction tube, with the 12 o'clock position being at the top and adjacent to the spine 2 when the suction device 100 is assembled. However, the light sources 15 may be provided at different angular positions, such as 2 o'clock and 10 o'clock or 4 o'clock and 8 o'clock, etc. Moreover, in other arrangements, one light source 15 or more than two light sources 15 may be arranged in other ways, such as a single light source above the suction tube 13 (e.g., at the 12 o'clock position) or three or more light sources around the suction tube 13. In addition, in other arrangements the optical elements may include a lens instead of a combination of a lens and a reflector, or may include a reflector without using the lens. FIGS. 7A-10B show additional exemplary arrangements of the illumination assembly in the suction device 100 of the present invention.

Figure 7A:
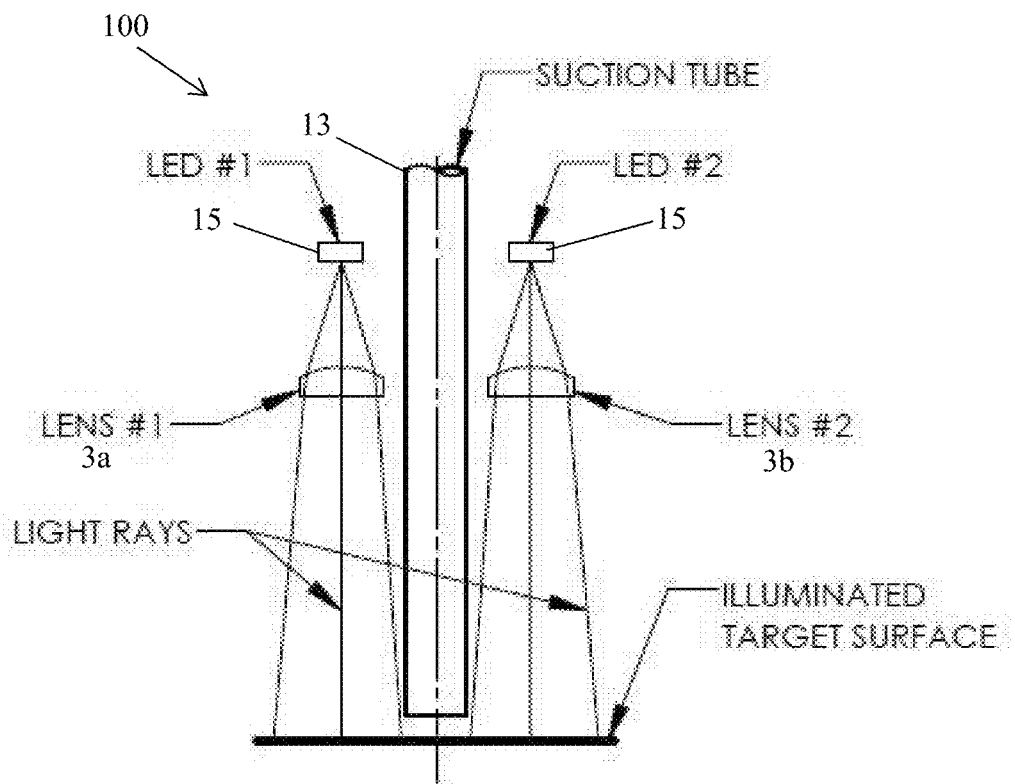
FIGS. 7A-7B show schematic top and front views of a second illustrative arrangement of the illumination assembly.
Figure 7B:
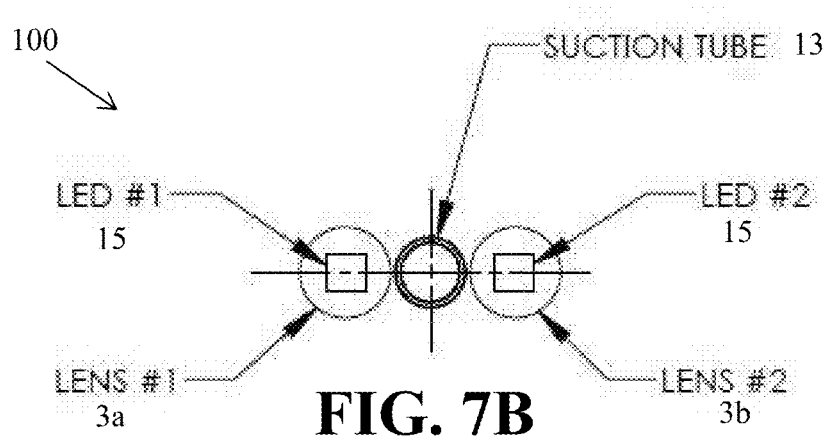

FIGS. 7A-7B show a top view of the distal end of the suction device 100 positioned in close proximity to the target surface to be illuminated and a front view thereof, which is viewed from the target surface looking proximally. As shown in FIG. 7A, the illumination assembly includes a pair of light sources 15, or two sets of light sources, each of which is provided adjacent to the side of the suction tube 13. As in the embodiment shown in FIGS. 6A and 6B, the light sources are provided at 3 o'clock and 9 o'clock positions relative to the axis of the suction tube 13. However, in some embodiments, their positions may be modified, e.g., at 2 o'clock and 10 o'clock, or 4 o'clock and 8 o'clock, or 4 o'clock and 10 o'clock, etc.

In this illustrative embodiment, the light sources 15 emit light in a direction along the suction tube 13 toward the distal end of the suction tube 13, e.g., the axis of the cone of emitted light from each light source is substantially parallel to the axis of the suction tube. The illumination assembly also includes a lens with two lens portions, similar to the lens described above, or two separate lenses 3a, 3b having the characteristics of the lens described above. The lenses 3a, 3b, which are made from a transparent material, are positioned so as to capture a significantly large portion of the light energy emitted from the light sources 15. The light rays emitted from the light sources 15 that get intercepted by the lenses 3a, 3b are preferably refracted in such a manner so as to maximally and uniformly illuminate the desired area of the target surface. The geometric design, location, and material of the lenses 3a, 3b work to direct as much of the light emitted as possible from the light sources into the desired area of the target surface, as well as to spread the light uniformly over the target area.

As can be seen in FIGS. 7A and 7B, the optical elements of this illustrative illumination assembly do not include a reflector. However, in some embodiments, the arrangement of FIGS. 7A, 7B may be modified to provide a reflector for reflecting some of the light from the light sources towards the lenses 3a, 3b, e.g., a reflector provided around the sides of the light sources to prevent light leaking around the sides of the lenses 3a, 3b.

Figure 8:
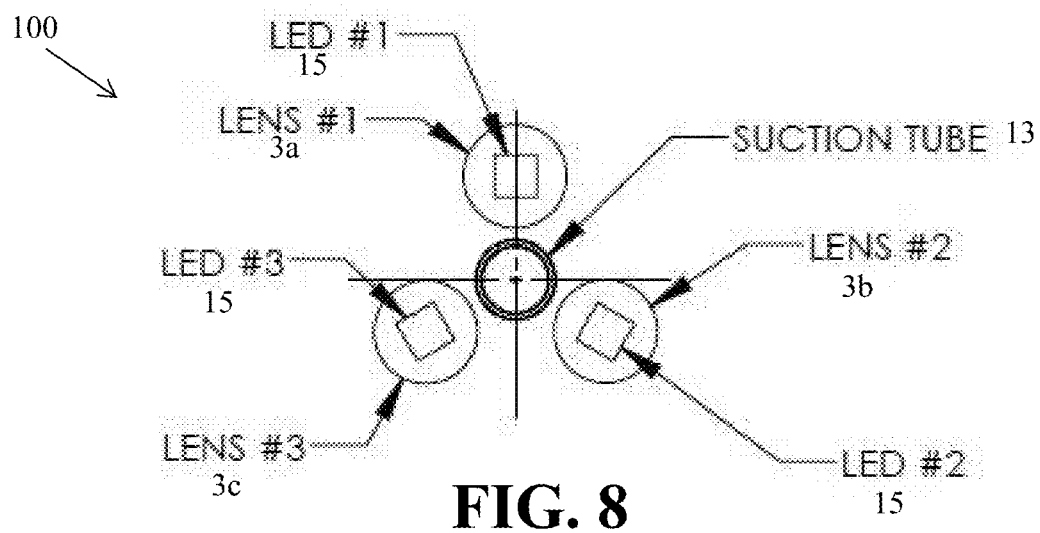
FIG. 8 shows a schematic front view of a third illustrative arrangement of the illumination assembly.
Figure 9:
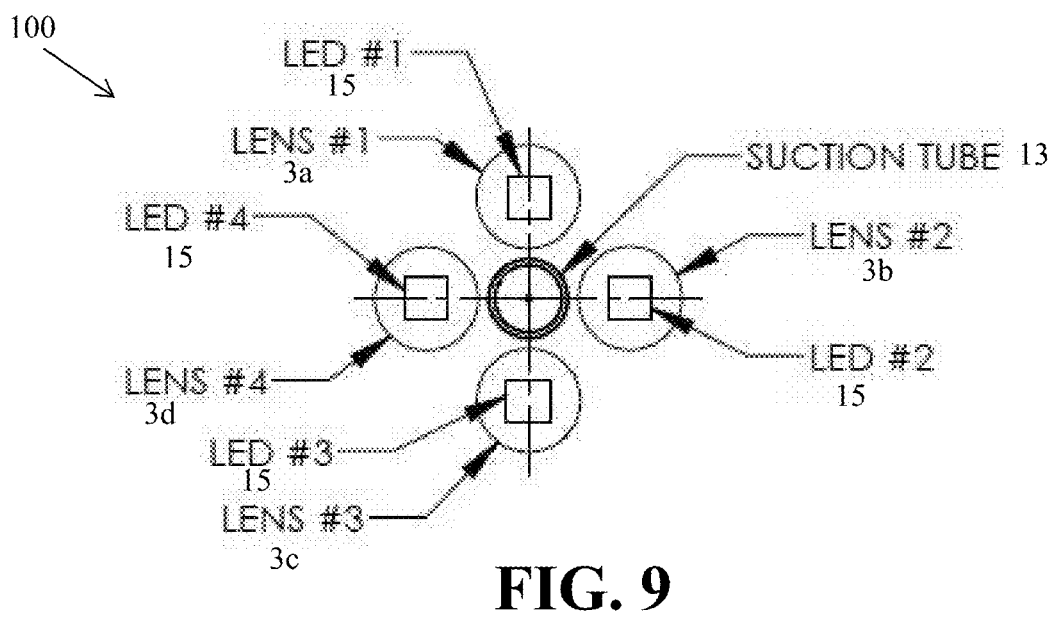
FIG. 9 shows a schematic front view of a fourth illustrative arrangement of the illumination assembly.

FIGS. 8 and 9 show additional arrangements of the illumination assembly of the present invention which uses more than two light sources. FIG. 8 shows a front view of the distal end of the suction device 100 viewed from the target surface looking proximally, with the illumination assembly including three light sources 15, or three sets of light sources. FIG. 9 shows a front view of the distal end of the suction device 100 in which the illumination assembly includes four light sources 15, or four sets of light sources. As shown in FIG. 8, the light sources 15 are provided at about 12 o'clock, 4 o'clock and 8 o'clock, with substantially uniform spacing between the light sources. However, in other configurations, the light sources 15 may be spaced differently so that the spacing between the light sources is not uniform, e.g., at about 12 o'clock, 3 o'clock and 9 o'clock. Similarly, in FIG. 9, the light sources 15 are provided at about 12 o'clock, 3 o'clock, 6 o'clock and 9 o'clock with substantially uniform spacing therebetween. However, in other configurations, the positions of the light sources 15 are not limited to those shown and may be varied, e.g., 2 o'clock, 4 o'clock, 8 o'clock and 10 o'clock, and the spacing between the light sources 15 does not have to be uniform.

In the arrangements shown in FIGS. 8 and 9, each illumination assembly includes a plurality of lenses 3a-3d or a lens with a plurality of lens portions, with each lens 3a-3d or lens portion corresponding to a light source 15. The light rays emitted from the light sources 15 get intercepted by the lenses 3a-3d, which refract the light rays so as to maximally and uniformly illuminate the desired area of the target surface. As in the other arrangements described above, the geometric design, location, and material of the lenses 3a-3d are configured to direct as much as possible of the light emitted from the light sources 15 into the desired area of the target surface, as well as to spread the light uniformly over the target area.

Figure 10A:
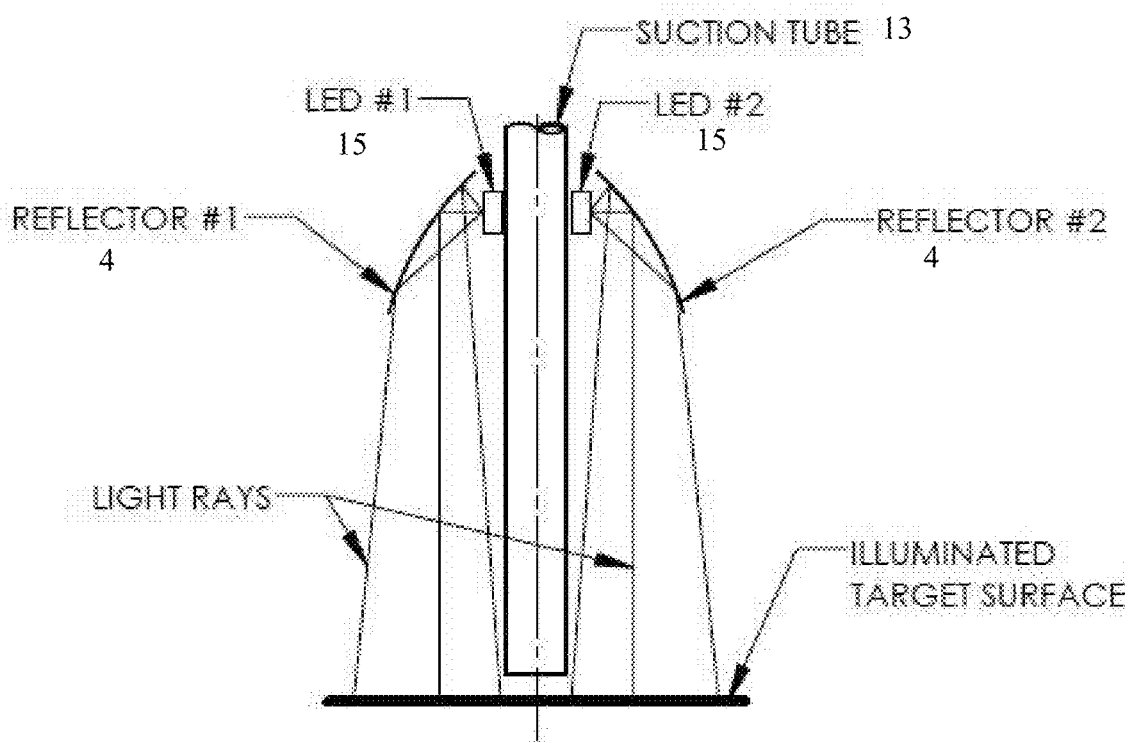
FIGS. 10A-10B show top and front views of a fifth illustrative arrangement of the illumination assembly.
Figure 10B:
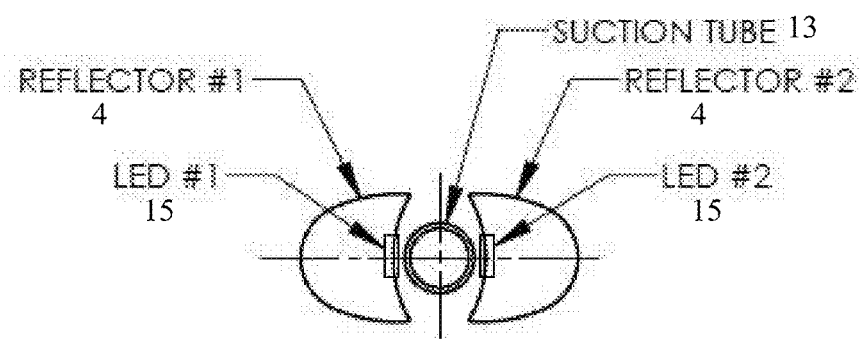

FIGS. 10A and 10B show a further illustrative arrangement of the illumination assembly of the suction device 100 in which the optical elements include a reflector and do not use a lens. FIG. 10A shows a top view of the distal end of the suction tube 13, which is positioned in close proximity to the target area to be illuminated, while FIG. 10B shows a front view thereof. In this arrangement, the illumination assembly includes two light sources 15 or two sets of light sources, which are positioned similarly to FIGS. 6A and 6B so as to radially emit light relative to the axis of the suction tube 13. The number of the light sources 15 or sets of light sources may be varied and their arrangement around the suction tube 13 may also be different from the arrangement shown in FIGS. 10A and 10B. The illumination assembly of FIGS. 10A-10B also includes one or more reflectors 4, which intercept a significantly large portion of the light emitted from the light sources 15 and redirect the light toward the target area. The one or more reflectors 4 may have the configuration shown in FIGS. 5A-5D or FIGS. 5E-5H and described above, or may be configured as two separate reflectors 4 each of which redirects light from a corresponding light source or set of light sources. In the embodiments which use a multi-faceted concave reflector 4 described above, the facets of the reflector 4 are arranged so that light from the light sources is redirected to the target area and so that the redirected light is substantially uniformly distributed in the target area.

The arrangements of the light sources 15 and the optical elements of the illumination assemblies shown in FIGS. 6A-10B are illustrative and may be modified depending on the desired illumination brightness, the size and shape of the target area, and available space within the medical device.

Figure 11A:
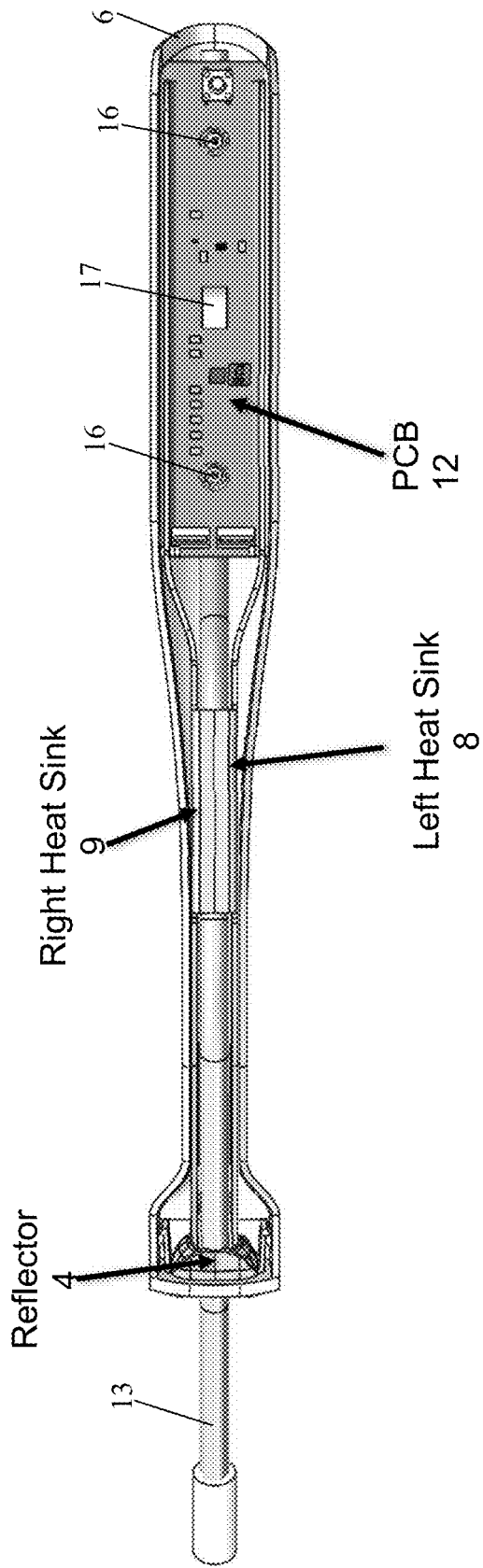
FIG. 11A shows a top view of the illuminated suction device of FIGS. 1A-1G with the spine and battery cover removed to expose internal components.
Figure 11B:
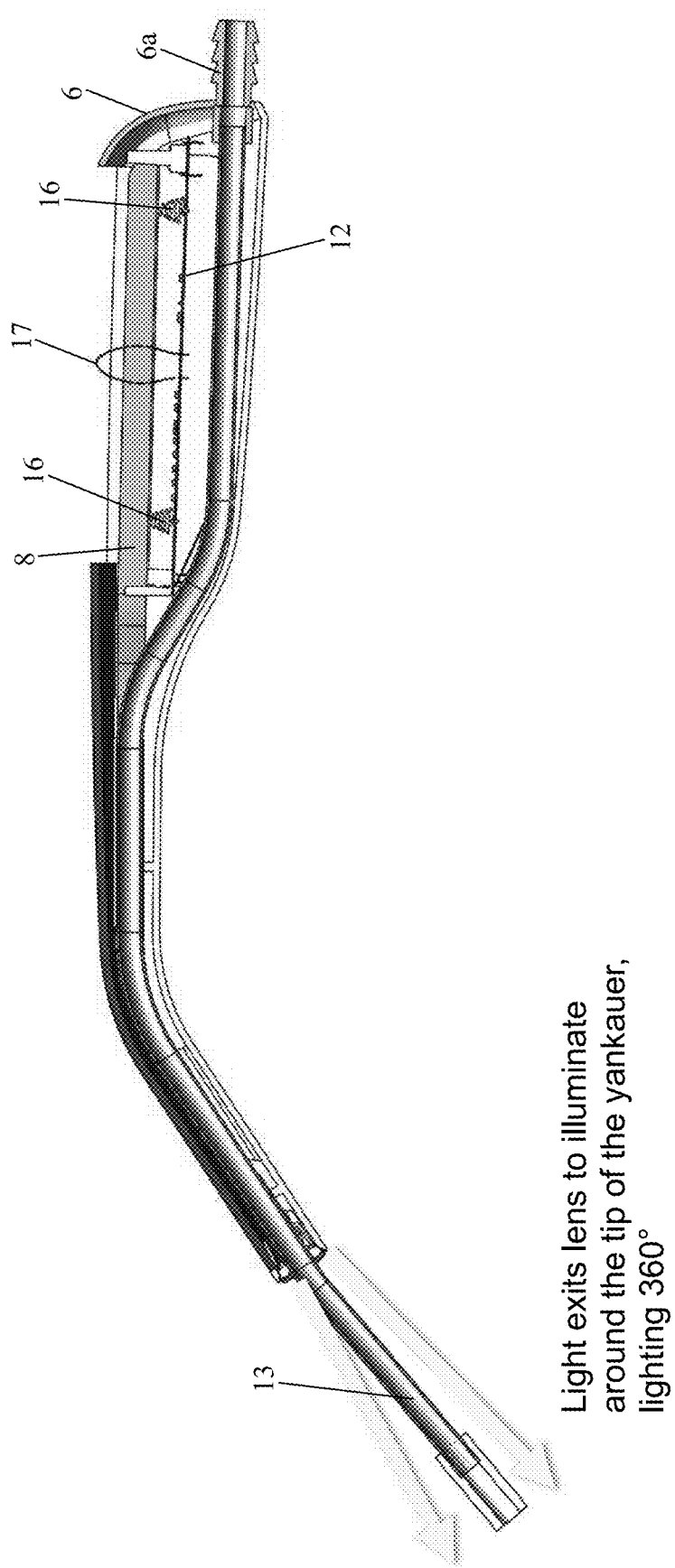
FIG. 11B shows a side cross-sectional view of the illumination suction device of FIG. 11B.
Figure 11C:
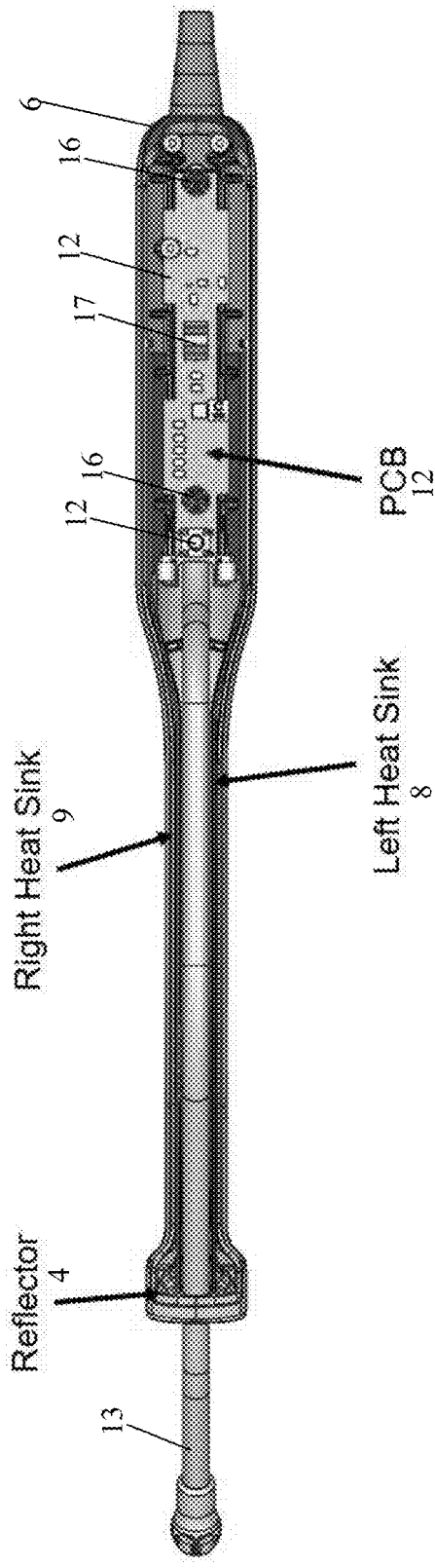
FIGS. 11C and 11D show top and side cross-sectional views of another variation of the illuminated suction device of FIGS. 1A-1G.
Figure 11D:
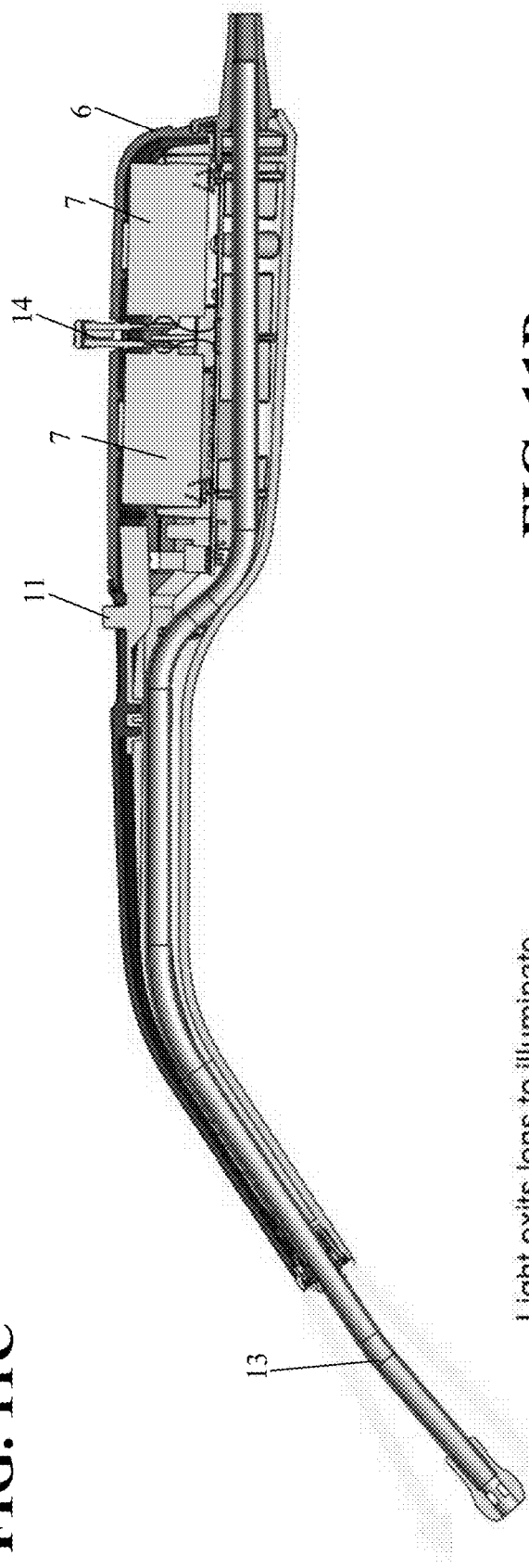

Other components of the suction device 100 shown in FIGS. 1A-1G will now be described with reference to FIGS. 11A-11D. FIGS. 11A and 11C show top views of the suction device 100 with the spine 2 and the battery cover 10 removed, while FIGS. 11B and 11D show side cross-sectional views of the suction device 100 with the battery cover removed. FIGS. 11A and 11B show one embodiment of the internal components of the suction device 100, while FIGS. 11C-11D show another embodiment of the internal components of the suction device 100. The same numbering is used for the same or similar components of the suction device 100.

As shown in FIGS. 11-11D, the suction tube 13 extends from its distal tip which is outside of the outer housing and through the entire length or substantially entire length of the body 1, and as shown in FIGS. 11B and 11D, the proximal tip of the suction tube 13 is fluidly coupled with the suction port 6a in the rear cap 6. In order to accommodate electrical components of the illumination assembly, including a controller assembly (a PCB controller assembly 12) and one or more power sources (7 in FIG. 11D), the body 1 of the outer housing increases in width or outer circumference near the proximal end thereof. The widened proximal portion of the body 1 may be used as a handle portion of the suction device. As shown in FIGS. 11B and 11D, the suction tube 13 in this illustrative embodiment is bent to substantially follow the general shape of the lower surface of the body 1 of the outer housing, such that the suction tube 13 extends under the electrical components of the illumination assembly housed within the outer housing. That is, the suction tube 13 of the suction device 100 extends through the body 1 of the outer housing from its distal end 1*b* to its proximal end 1*a* alongside the power source and other electrical components of the illumination assembly.

As shown in FIGS. 11A-11D, the electrical components of the illumination assembly include the controller assembly comprising a printed circuit board (PCB) controller assembly 12 for controlling the light sources of the illumination assembly. The PCB controller assembly 12 may use a rigid PCB controller or a flexible PCB controller. The PCB controller assembly 12 is connected to the switch, such as the button lever 11 described above, and to the light sources using suitable wiring, which may be part of a flexible circuit and in some embodiments includes exposed traces that are insertable into the PCB controller assembly 12. In some embodiments, the PCB controller assembly includes ON/OFF control circuits for controlling the light sources. In other embodiments, the PCB controller assembly, which also includes a dimmer circuit and/or one or more circuits for controlling the sequence of turning ON/OFF and/or the color of the light sources, similar to the one described in U.S. Pat. No. 10,512,519, which is assigned to the same assignee herein and incorporated herein by reference, may be used in the suction device 100 of the present invention. As in the '519 patent, the internal surface of the body 1 may include ribs or projections which are used for holding the suction tube 13 in place and/or for positioning the PCB controller assembly 12 and for keeping it in place within the body 1.

To power the light sources of the illumination assembly, one or more power sources 7, such as batteries, can be connected to the PCB controller assembly 12 via springs 16 or similar electrical contacts and a central contact 17 mounted on the PCB controller assembly 12. The springs 16 hold the batteries in place against the battery cover 10 when the batteries and the battery cover are installed, and electrically connect the batteries using electrical connection plates on the batteries, as shown and described in the '519 patent, or using other suitable electrical connectors. The central contact 17 on the PCB controller assembly 12 provides electrical conductivity between the batteries. In certain embodiments, such as the one shown in FIG. 11D, the central contact 17 is configured to have a push-tab 14 engage therewith so as to electrically isolate the batteries from one another in a "storage" configuration (resulting in an open circuit), and to electrically connect the batteries in a "use" configuration (resulting in a closed circuit). As mentioned herein above, the details of the push-tab assembly are described in the '519 patent, which is incorporated herein by reference, and the same or substantially the same push-tab assembly may be used in the suction device 100 of the present invention.

Referring to FIGS. 2D and 11A-11D, the suction device also includes a heat sinking assembly for dissipating heat generated by the light sources when providing illumination. The heat sinking members extend within the outer housing along at least a substantial portion of the length of the outer housing. Specifically, as shown in FIGS. 11A-11C, the heat sinking members 8, 9 extend from the light sources through at least a portion of the body 1. The heat sinking assembly ensures that the suction device will not heat up so as to damage patient tissues and that the suction device is safe to come into contact with patient tissues.

As shown in FIG. 2D and FIGS. 11A-11C, the heat sinking assembly includes one or more heat sinking members 8, 9, or heat sinking plates, each of which dissipates heat generated by a corresponding light source or set of light sources. In the illustrative configurations of FIGS. 2D and 11A-11C, the heat sinking assembly includes a left heat sinking member 8, such as a heat sinking plate, which is thermally coupled to the light source or set of light sources provided adjacent to the left side of the suction tube 13, and a right heat sinking member 9, such as a heat sinking plate, which is thermally coupled to the light source or set of light sources provided adjacent to the right side of the suction tube 13.

The left heat sinking member 8 dissipates heat generated by a left light source, and the right heat sinking member 9 dissipates heat generated by a right light source, with the heat sinking members 8, 9 extending from the corresponding light source along each side of the suction tube 13 and PCB controller assembly 12 to the proximal portion of the body 1. The configuration of the heat sinking assembly is described in more detail below with reference to FIGS. 12A-12D and FIGS. 12E-12H.

Figure 12D:
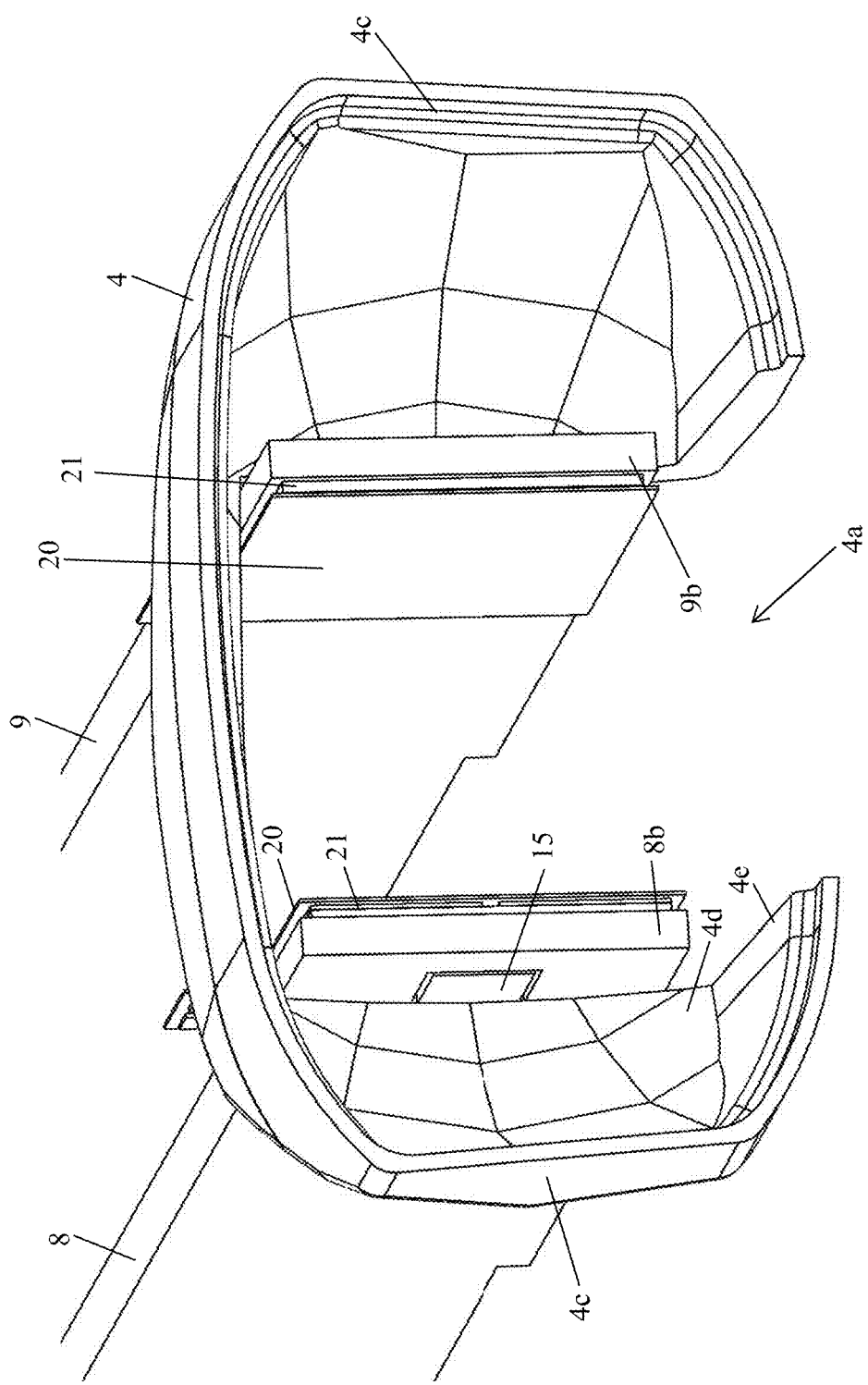
Figure 12E:
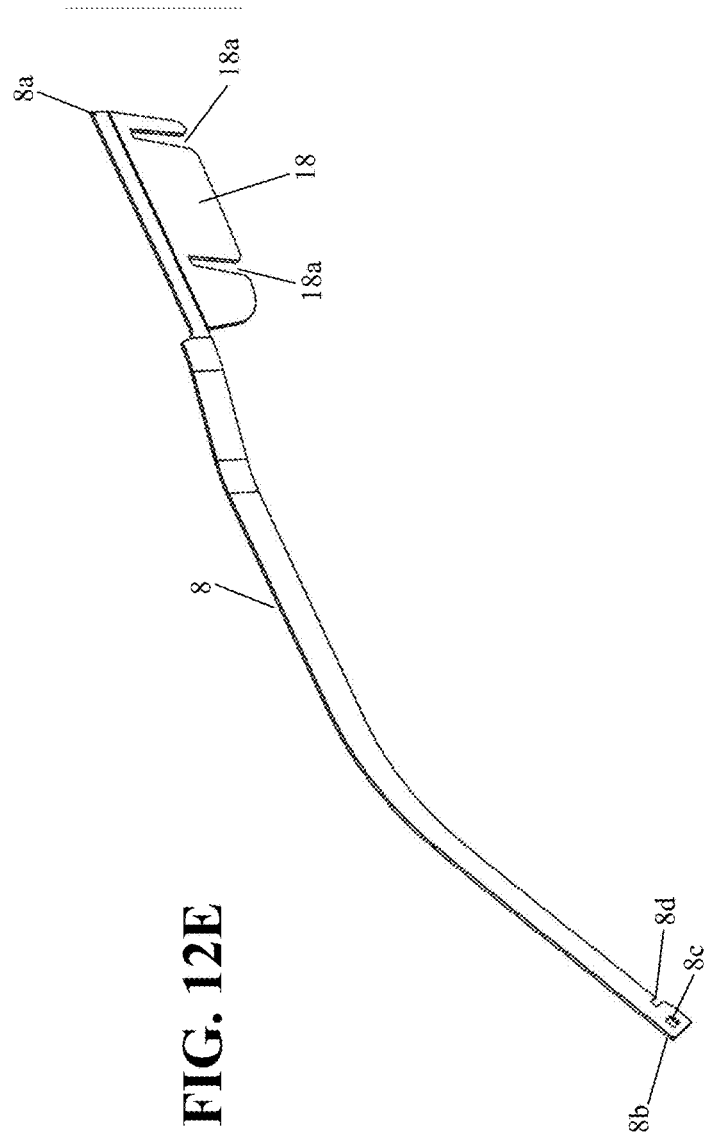
FIG. 12E shows another exemplary heat sinking member for dissipating heat.

FIG. 12A shows an exemplary heat sinking member 8, or heat sinking plate, for use in the heat sinking assembly of the present invention, and FIGS. 12B and 12C show assembly of a distal end of the heat sinking member 8 with the light source 15 of the illumination assembly. FIG. 12D shows distal ends of the heat sinking members 8, 9 assembled with the light sources 15 and the reflector 4 of the illumination assembly.

As shown in FIG. 12A, the heat sinking member 8 comprises an elongated plate, which has a curvature that follows the shape of the body. The heat sinking member 8 is formed from a material having high thermal conductivity that is able to readily conduct heat generated from the light sources 15 and/or from electrical components. In certain embodiments, the heat sinking member 8 is formed from a metallic material, such as copper, copper alloys, aluminum alloys, etc. However, other suitable heat sinking materials may be used.

As shown in FIG. 12A, the illustrative heat sinking member 8 includes a fin 18 or a widened portion at the proximal end 8*a* thereof corresponding in position to the thickened proximal portion of the body when assembled. The overall shape of the illustrative heat sinking member 8 is configured to extend along the side of the suction tube 13, particularly the distal portion of the suction tube, and curves outwardly so as to extend along the PCB controller assembly 12 within the widened proximal portion of the body. However, the overall shape of the heat sinking member may vary depending on the configuration of the suction device or of the medical device in which it is used. The fin 18 of the heat sinking member 8 provides additional surface area for conduction, convection, and radiation in order to provide additional heat dissipation to the exterior of the housing (body 1) and thence to the atmosphere or to the surgeon's hand.

In the present invention, the purpose of the heat sinking members 8, 9 is to conduct heat as efficiently as possible from the light sources to the exterior surface of the housing, from which the heat can continue its journey to either the atmosphere or the surgeon's hand. It is desired that the heat is internally applied to as large a portion of the housing as possible so that the temperature rise of the housing remains small and to avoid the rise of temperature being so high that it would be uncomfortable or painful to hold the handle of the suction device. In some embodiments, the outer housing of the suction device is formed from plastic. Since plastic has poor thermal conductivity, it would require a large temperature difference to spread the heat around the housing from one place to another. In these embodiments, copper or other efficient thermally conducting materials are used for the heat sinking members 8, 9, and a large area of the heat sinking members 8, 9 is held close to the housing in order to conduct and convect the heat to the housing and through the housing to the exterior face of the housing.

The illustrative heat sinking member 8 may also include one or more positioning projections 19 for positioning the heat sinking member 8 relative to the suction tube and for maintaining its position within the body. The positioning projections 19 also provide additional surface area for heat transfer to the housing body 1. In the present invention, the heat sinking member 8 is also insulated as much as feasible from the suction tube in order to keep the suction tube cool since its distal end comes into contact with the patient.

In the illustrative heat sinking member 8 of FIG. 12A, as shown in more detail in FIGS. 12B and 12C, the distal end 8b includes one or more openings 8c or cutouts for assembly with the light source 15 or a set of light sources, and in some embodiments, the distal end 8b may be recessed or reduced in thickness in order to accommodate the light source 15 or a set of light sources. FIG. 12B shows the distal end 8b of the heat sinking member 8 assembled with one light source 15, while FIG. 12C shows the engagement between the light source 15 and the opening 8c in the heat sinking member 8 in more detail. It is understood that the heat sinking member 8 may be modified to be assembled with multiple light sources 15 using the same or similar engagement therebetween.

In the illustrative embodiment of FIGS. 12B-12C, the light source 15 is mounted on a flexible circuit 20 by soldering the light source 15 onto a flexible circuit substrate 20a or using other suitable techniques for mounting the light source 15 thereon. Flexible circuits with one or more light sources mounted thereon described in U.S. Pat. No. 10,512, 519, incorporated herein by reference, are suitable for use in the illumination assembly of the present invention. The light source is inserted into the opening 8c in the distal end 8b of the heat sinking member 8, as shown in FIGS. 12B and 12C, so that the light emitting surface of the light source 15 is exposed through the opening 8c. With this arrangement, the distal end 8b of the heat sinking member 8 surrounds the light source 15 so as to absorb the heat generated by the light source 15.

In FIGS. 12B-12C, thermally conductive tape 21, and in particular, thermally conductive double-sided adhesive tape, is used to thermally and mechanically connect the light source 15 and the flexible circuit 20 to the heat sinking member 8. Specifically, thermally conductive double-sided tape 21 is provided between the heat sinking member 8 and the flexible circuit 20 so as to attach the flexible circuit 20 to the heat sinking member 8. The thermally conductive tape 21 provides a thermal interface between the heat sinking member and the flexible circuit 20 with the light source 15. Bergquist BP100-0.005-00-1010 thermally conductive tape or similar tape which is thermally conductive (0.8 W/m-° K), electrically insulating and preferably having a thickness of about 0.005" or smaller is suitable for use as the thermally conductive tape in this assembly. In some embodiments, suitable thickness of the thermally conductive tape is between 0.008" and 0.005".

FIG. 12D shows how the heat sinking members 8, 9 with the light sources 15 mounted on flexible circuits 20 are assembled with the reflector 4 of the illumination assembly. As discussed above with respect to FIGS. 5A-5D, the reflector 4 includes a cutout 4a in the back and bottom walls 4d, 4e thereof. The cutout 4a is sized so as to allow the distal ends 8b, 9b of the heat sinking members 8, 9 assembled together with the light sources 15 and flexible circuits 20 to pass through the cutout 4a in the back wall 4d so that the light sources 15 are surrounded by the reflector 4. As shown in FIG. 12D, the distal ends 8b and 9b of the heat sinking members 8, 9 are inserted into the reflector 4 through the cutout 4a, and the light sources 15 assembled with the heat sinking members 8, 9 face sidewalls 4c of the reflector 4. As discussed herein above, during operation of the illumination assembly, the light sources 15 shine light out side to side, radially away from the axis of the suction tube 13, and the reflector 4 reflects the light toward the front of the device. Heat produced by the light sources 15 during operation is conducted away by the heat sinking members 8, 9, which allows the light sources 15 to operate safely at high brightness for long periods of time without overheating the suction device.

In the present illustrative embodiment, the flexible circuits 20 serve as thermal insulators between the heat sinks 8, 9 and the suction tube 13. That is, their substrate portion, typically made of Kapton or a similar polymer, has relatively low thermal conductivity, and is interposed between the heat sinks 8, 9 and the tube 13. Further, in some embodiments, there are ribs or protrusions on the body 1 that serve to hold the heat sinks 8, 9 away from tube 13 as much as possible. The goal is to minimize heat transfer from the relatively hotter heat sinks 8, 9 to the relatively cooler tube 13, because said tube 13 extends distally out of the housing and typically comes into contact with patient tissue.

An important feature of the lighting assembly is that it minimally obscures the visualization of the target area by the operator. The constraints of uniform lighting pattern, light intensity, and heat dissipation create significant challenges to lighting assembly size, and resulting visualization impairment. These constraints are optimally addressed by:

1. Mounting the LEDs such that light projects radially, and is then redirected and focused by a reflector and lens.
2. Mounting the LEDs through a heat sink cutout, such that the heat sink is no thicker than the LED and adds no additional width to the assembly, and self-aligns the LED to the cutout for easy of assembly and maximum heat conduction.

Although FIGS. 12A-12D show the heat sinking assembly that is configured for the illumination assembly arrangements shown in FIGS. 2A-2I, 6A-6B and 10A-10B described above, in other embodiments, the heat sinking assembly is modified so that the heat sinking members can be used with forward facing light sources, as in FIGS. 7A-9, or with light sources facing in other directions. For example, the distal ends of the heat sinking members 8, 9 may be modified to include a flange or an L-shaped edge with an opening or a cutout for accommodating the light source. In addition, the heat sinking assembly may be modified to include more than two heat sinking members for use with illumination assemblies that include more than two light sources or more than two sets of light sources.

FIGS. 12E-12H show a modified sinking assembly, which has similar features to the sinking assembly of FIGS. 12A-12D. FIGS. 12E-12H use the same reference numbers for the same or similar features of the sinking assembly and detailed discussion thereof is omitted. In the embodiment of FIGS. 12E-12H, the shape of the heat sinking member 8 is modified to include recesses or cutouts 18*a* in the fin 18 portion of the heat sinking member 8 and to include a recess or notch 8*d* in the distal end 8*b* of the heat sinking member. Such cutouts 18*a* and notch 8*d* are used for positioning the heat sinking member 8 within the body 1. The other heat sinking member 9 has the same configuration as that shown in FIG. 12E.

Figure 12G:
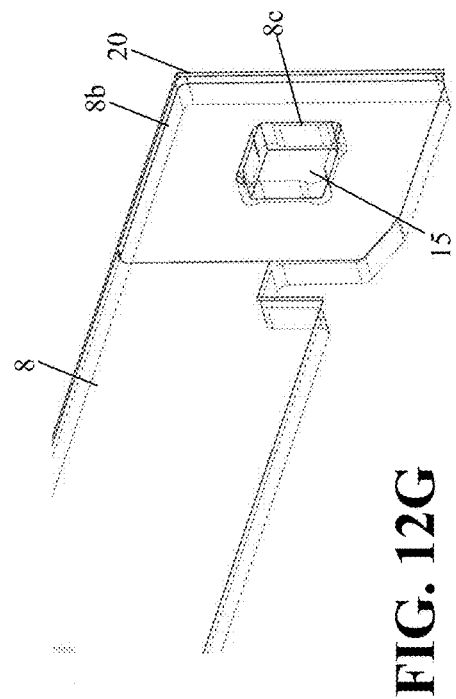
FIGS. 12F-12H show assembly of the heat sinking member of FIG. 12E with the illumination assembly shown in FIGS. 2E-2I.
Figure 12F:
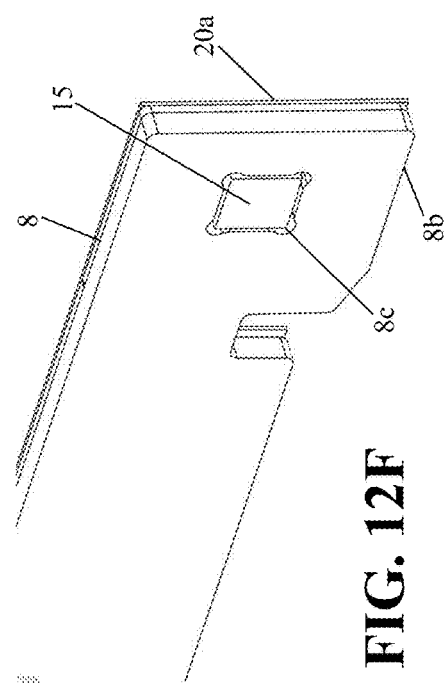
Figure 12H:
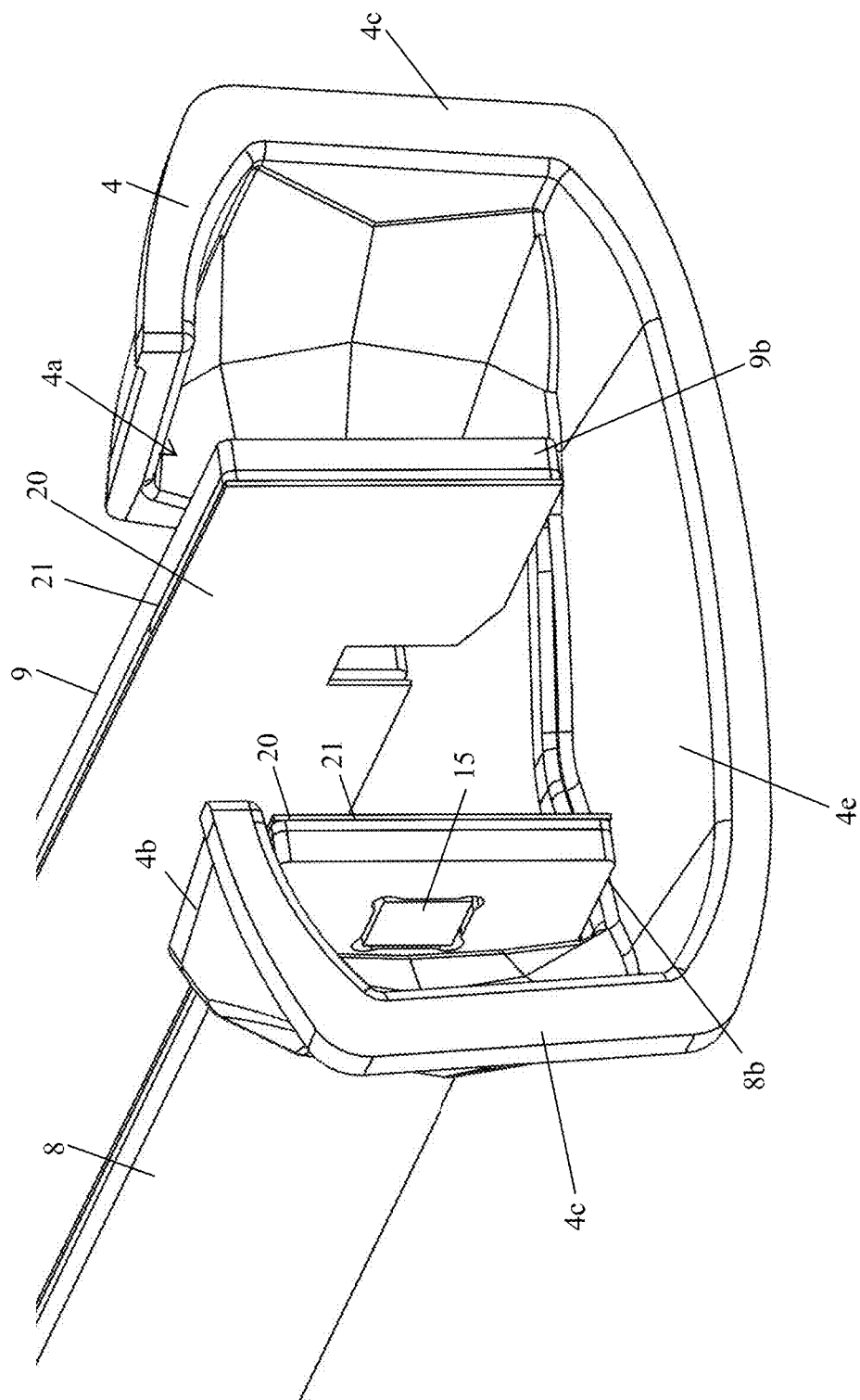

FIGS. 12F and 12G show the heat sinking member 8 assembled together with the light source 15 mounted on a flexible circuit 20, with the light source 15 being inserted into the opening 8*c* in the distal end 8*b* of the heat sinking member. As discussed above, the flexible circuit 20 is attached to the heat sinking member 8 using thermally conductive tape 21. FIG. 12H shows the heat sinking members 8, 9 with the flexible circuits 20 assembled therewith being used with the reflector 4. In the embodiment of FIG. 12H, the reflector 4 shown in FIGS. 2E-2I and 5E-5H is used with the heat sinking members 8, 9. However, in other embodiments, the reflector 4 of FIGS. 2A-2D and FIGS. 5A-5B may be assembled with the heat sinking members 8, 9.

As discussed above with respect to FIGS. 1A-1G, the suction tube 13 of the suction device 100 passes through an opening in the lens 3 to the outside of the outer housing, and sealing may be added between the suction tube and the lens 3 so that the outer housing has a fluid tight construction. The sealing between the suction tube 13 and the lens 3 prevents bodily fluids from entering the outer housing of the suction device 100. If bodily fluids enter the outer housing through the opening in the lens 3, they could reduce the effectiveness of the reflector and the lens in reflecting/transmitting light, and can potentially damage the electrical components of the illumination assembly. FIGS. 13-18 show different lens 3 to suction tube 13 sealing options for use in the suction device 100 of the present invention.

Figure 13:
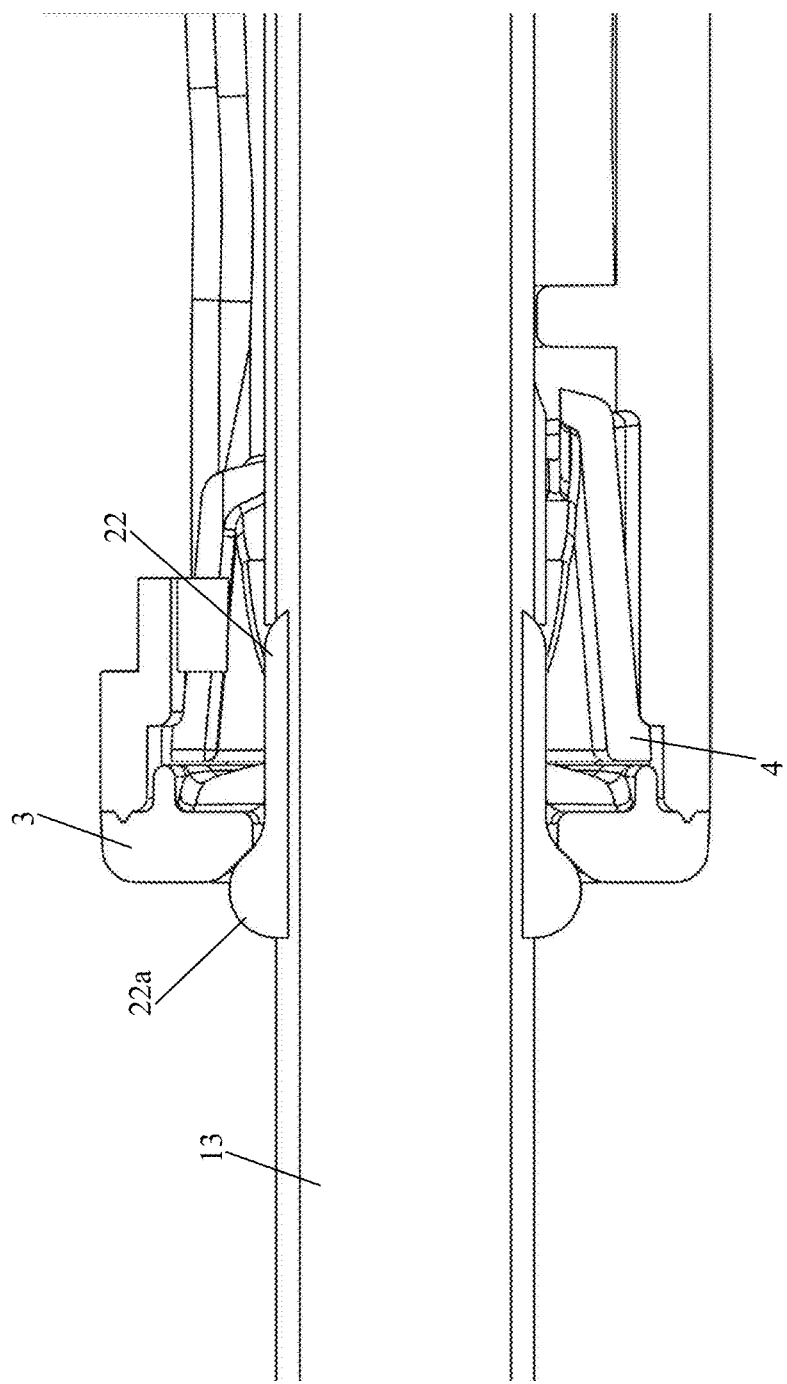
FIG. 13 shows a first exemplary sealing assembly for sealing a suction tube to the lens of the illumination assembly.

FIG. 13 shows a cross-sectional view of the lens 3 to suction tube 13 sealing. In FIG. 13, the space or interface between the lens 3 and the suction tube 13 is sealed using a gasket 22, which is inserted into the space between the lens 3 and the suction tube 13 from the front or light output surface of the lens. The gasket 22 has a substantially cylindrical shape sized to allow the suction tube to be inserted into the opening in the gasket 22 and includes a thickened rim 22*a* or a flange at one end. The gasket 22 forms a seal between an inner diameter of the opening in the lens and the outer diameter of the suction tube 13. The gasket 22 may be formed from silicone, rubber or other waterproof, elastomeric materials.

Figure 14B:
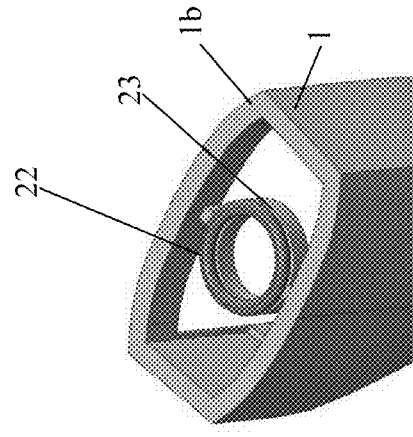
FIGS. 14A-14C show a second exemplary sealing assembly for sealing the suction tube to the lens of the illumination assembly.
Figure 14C:
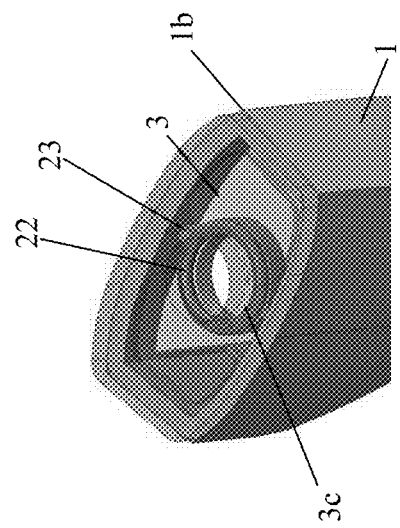
Figure 14A:
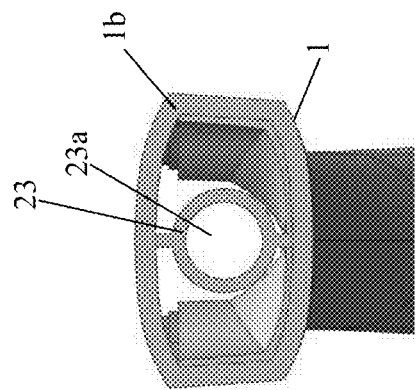

FIGS. 14A-C show another sealing arrangement between the lens 3 and the suction tube 13. As shown in FIGS. 14A-14C, the distal end 1*b* of the body 1 includes a gasket mount 23 for mounting a gasket 22 to seal the space between the lens 3 and the suction tube 13. When the lens 3 is mounted to the distal end 1*b*, the gasket mount 23 is positioned behind the lens 3, inside the outer housing, and the gasket 22 is held between the lens 3 and the gasket mount 23. In the illustrative embodiment shown, the gasket mount 23 has an opening 23*a* which corresponds substantially to the opening in the lens 3, and the gasket 22 is ring-shaped with an opening that also corresponds substantially to the opening in the lens 3. The opening in the gasket 22 is sized so as to allow the suction tube 13 to be inserted into the opening, and so that the gasket 22 tightly surrounds the suction tube 13 in order to seal the space between the suction tube 13 and the lens 3. The shape of the gasket mount 23 is selected so as to avoid interference with the light being refracted by the lens 3 and to avoid formation of shadows. In the present illustrative example, the gasket mount 23 is circular in shape, corresponding to the opening in the lens and is attached to the body in positions corresponding to the bridge 3*c* of the lens 3. The gasket 22 may be formed from silicone, rubber or other waterproof, elastomeric materials. The gasket mount 23 may be molded from the same materials as the body 1.

FIGS. 15A-15D show another example of sealing between the lens 3 and the suction tube 13 in which a gasket 22 is inserted from the back of the lens 3 and is held against the lens inside the outer housing. As shown in cross-sectional views of FIGS. 15A and 15B, the gasket 22 is an O-ring which is held against the back surface of the lens 3 adjacent to the opening in the lens. The O-ring seals the space between lens 3 and the suction tube 13 inserted into the opening in the lens 3. As in other embodiments, the O-ring gasket 22 is formed from an elastomeric material, such as rubber, silicone, plastic or the like.

Figure 15A:
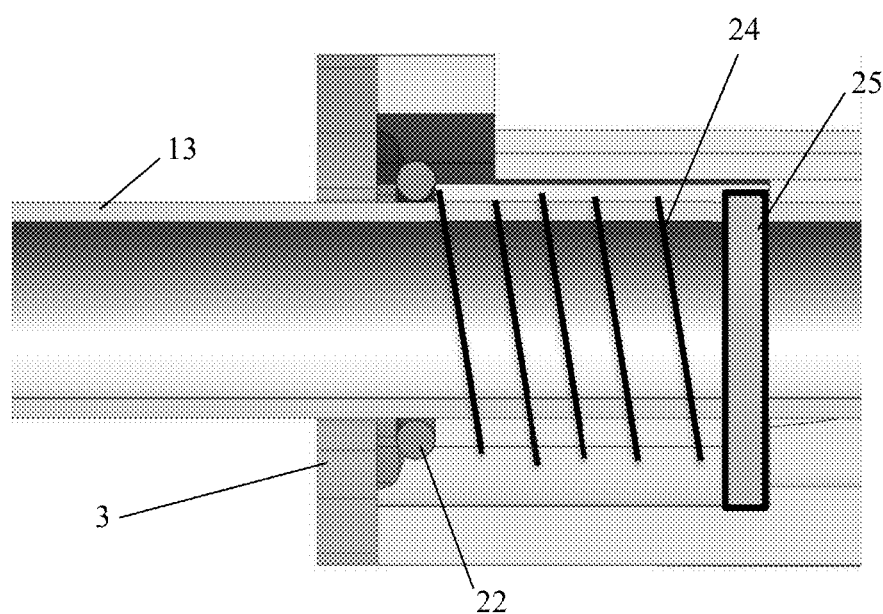
FIGS. 15A-15D show a third exemplary sealing assembly for sealing the suction tube to the lens of the illumination assembly.
Figure 15D:
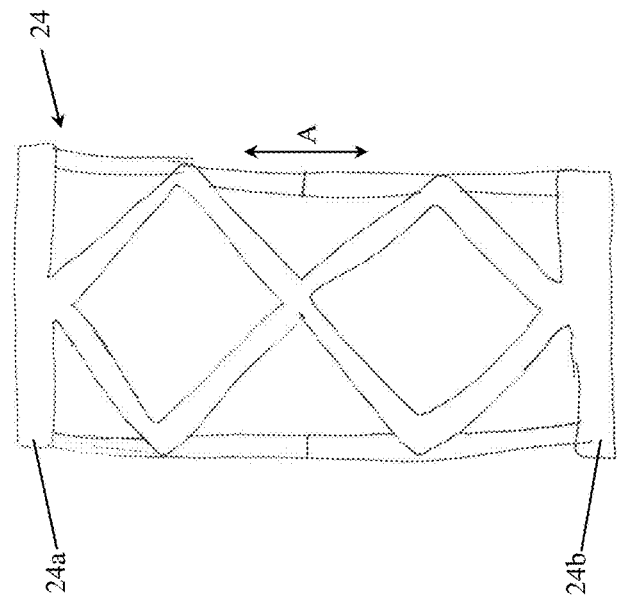
Figure 15C:
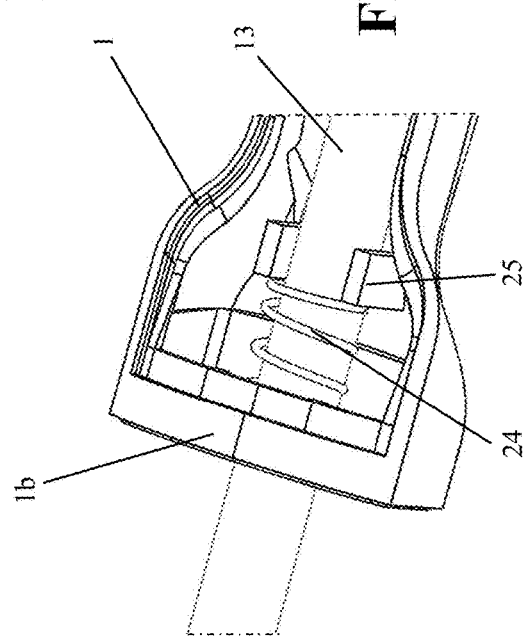
Figure 15B:
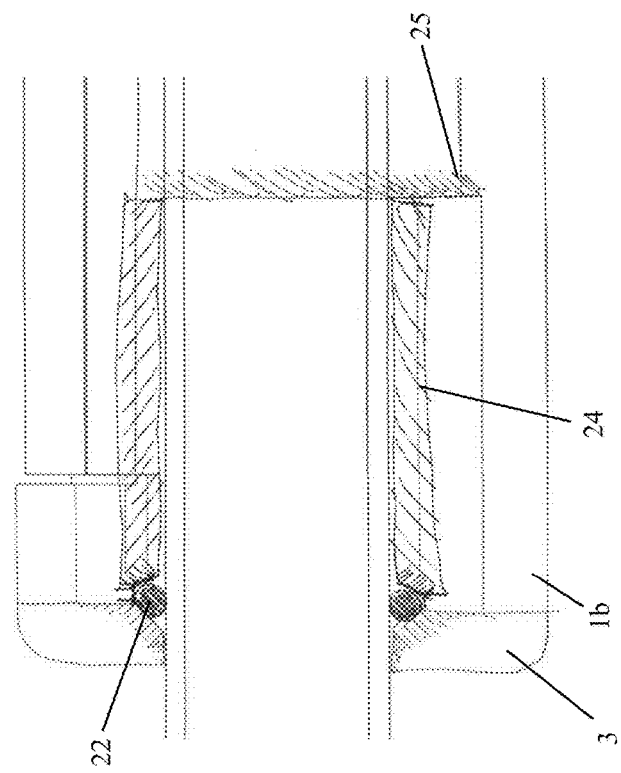

As shown in FIGS. 15A-15C, a biasing member 24, such as a spring, biases the gasket 22 against the lens 3 within the outer housing and prevents the gasket 22 from moving. As shown in FIG. 15C, the body 1 may include internal projections or ribs 25 against which the biasing member 24 is held in place, so that the biasing member 24 is provided between the internal projections 25 and the rear surface of the lens 3. In this embodiment, it is important to arrange the gasket 22, the internal projections 25 on the body and the biasing member 24 so that they do not block or interfere with the light emitted from the light sources and reflected from the reflector. FIG. 15D shows an exemplary biasing member 24 which functions as a spring and can be injection molded from plastic or polymer materials. The biasing member 24 has a generally cylindrical shape with a through opening extending between two ends 24*a*, 24*b*. The biasing member 24 is configured to be positioned around the suction tube and one end 24*a* of the biasing member is configured to push a seal against the rear surface of the lens. The biasing member 24 of FIG. 15D is capable of flexing in a direction A shown in FIG. 15D. Biasing members having a different shape and formed using injection molding are also suitable for sealing the spacing between the lens and the suction tube.

Figure 16:
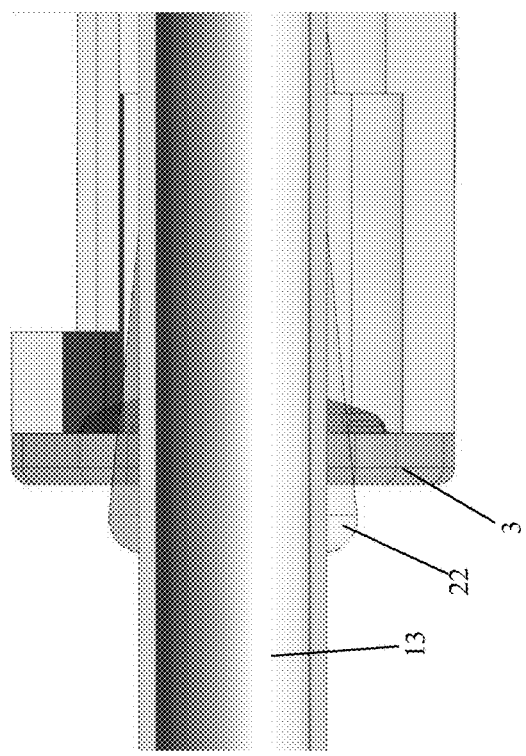
FIG. 16 shows a fourth exemplary sealing assembly for sealing the suction tube to the lens of the illumination assembly.

FIG. 16 shows another example of sealing between the lens 3 and the suction tube 13. In this example, the suction tube 13 includes an overmolded sealing member 22 provided on its outer surface which is shaped and sized so as to be partially inserted into the opening in the lens 3 and so as to seal the interface between the lens and the suction tube 13. The overmolded sealing member 22 functions similarly to the gasket, but is overmolded on suction tube 13 so that no additional components are required for holding it in place relative to the suction tube 13. The overmolded sealing member 22 may be configured as a Luer taper, which can be a Luer slip or slip-tip style connector shown in FIG. 16. In some cases, a Luer lock style connector with a male or female fitting that mates with a corresponding thread in the opening of the lens may be used. The overmolded sealing member 22 may be formed from plastic or polymer materials, and in some embodiments may be formed from elastomeric materials such as rubber, silicone or a polymer material.

Figure 17:
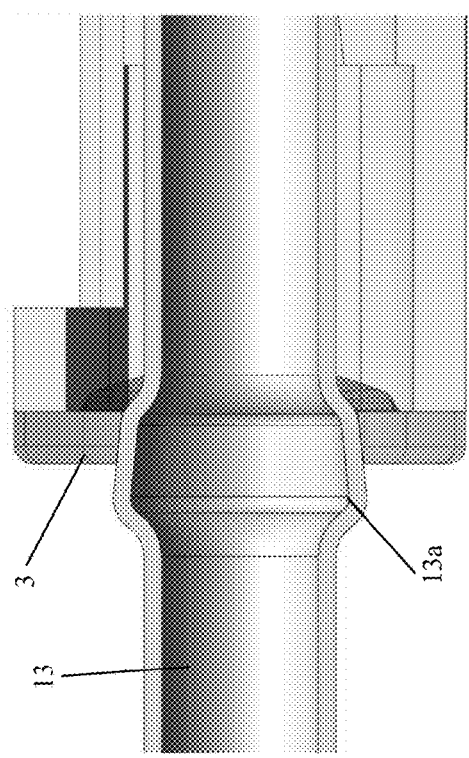
FIG. 17 shows a modification to the suction tube for providing sealing between the tube and the lens of the illumination assembly.

FIG. 17 shows an example of sealing between the lens 3 and the suction tube 13 in which the suction tube 13 includes a sealing portion 13*a* configured to be partially inserted into the opening in the lens 3 and to seal the space between the lens 3 and the suction tube 13. As shown in FIG. 17, the sealing portion 13*a* is a portion of the suction tube 13 having a greater diameter or being larger in size and shaped so as to taper in the proximal direction of the suction tube. In certain embodiments, the suction tube 13 or just the sealing portion 13*a* of the suction tube 13 may be coated with a polymer, rubber or silicone coating so as to improve the seal between the lens 3 and the suction tube 13. The shape of the sealing portion 13*a* is not limited to the shape shown in FIG. 17 and may be varied.

Figure 18:
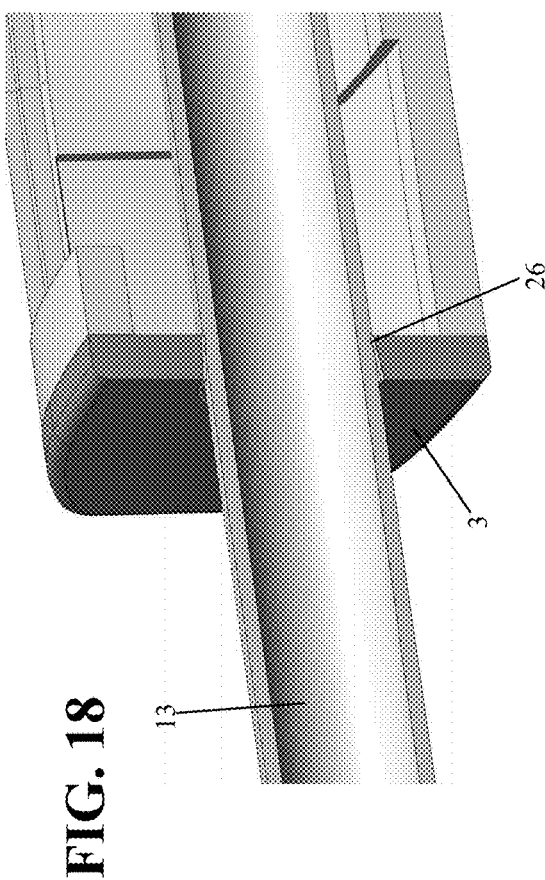
FIG. 18 shows a further embodiment sealing the suction tube to the lens of the illumination assembly.

FIG. 18 shows another example of sealing provided between the lens 3 and the suction tube in which an adhesive material 26, such as glue, or another sealing or caulking type material is provided between the lens 3 opening and the suction tube 13. The adhesive or sealing material 26 may be applied to the opening in the lens 3 or to the interface between the lens and the suction tube 13. The adhesive or sealing material 26 may be cured using UV light after application.

The sealing options described in FIGS. 13-18 are illustrative and in other embodiments, other types of sealing or no sealing may be provided between the lens and the suction tube.

FIGS. 19A-31 show an illustrative process of assembling the suction device 100 of the present invention, which may be the suction device 100 of FIGS. 1A-1G with the illumination assembly of FIGS. 2E-2I. The order of the assembly process proceeds in the order of FIGS. 19A-31. However, in other embodiments, the order of some assembly steps may be changed in order to adjust the manufacturing process.

As shown in FIGS. 19A and 19B, the body 1 of the suction device 100 and the reflector 4 are provided and the reflector 4 is inserted into the distal end 1*b* of the body 1 via an opening 1*c* extending along the top of the body 1. As shown in FIGS. 20A-20B, the lens 3 is then attached to the distal end 1*b* of the body 1 so as to cover the opening 1*d* in the distal end 1*b* of the body. In some embodiments, the lens 3 is attached to the body 1 using ultrasonic welding. In other embodiments, the lens 3, and in particular, the periphery of the lens, is configured to allow the lens 3 to be snap fitted to or interlocked with the distal end 1*b* of the body 1. In yet other embodiments, the top opening 1*c* in the body may extend to edge of the distal end 1*b* of the body 1 and the lens 3 may be assembled into the body 1 by sliding into the opening 1*c* and engaging with the sidewalls of the distal end 1*b* of the body 1. Other methods of attaching the lens 3 to the body 1 may be used, including gluing the lens 3 to the body 1, etc.

As shown in FIGS. 21A-21C, the suction tube 13 is assembled into the suction device 100 by sliding the proximal end (tail end) of the suction tube 13 into the body 1 through the opening in the lens 3. As shown in FIGS. 21B-21C, the suction tube 13 includes a gasket 22 attached thereto, with the gasket being similar to the one shown in FIG. 13. The gasket 22 is later partially slid into the opening in the lens 3 to provide sealing. As discussed above, other sealing options may be used instead of the gasket of FIG. 13.

Figure 22:
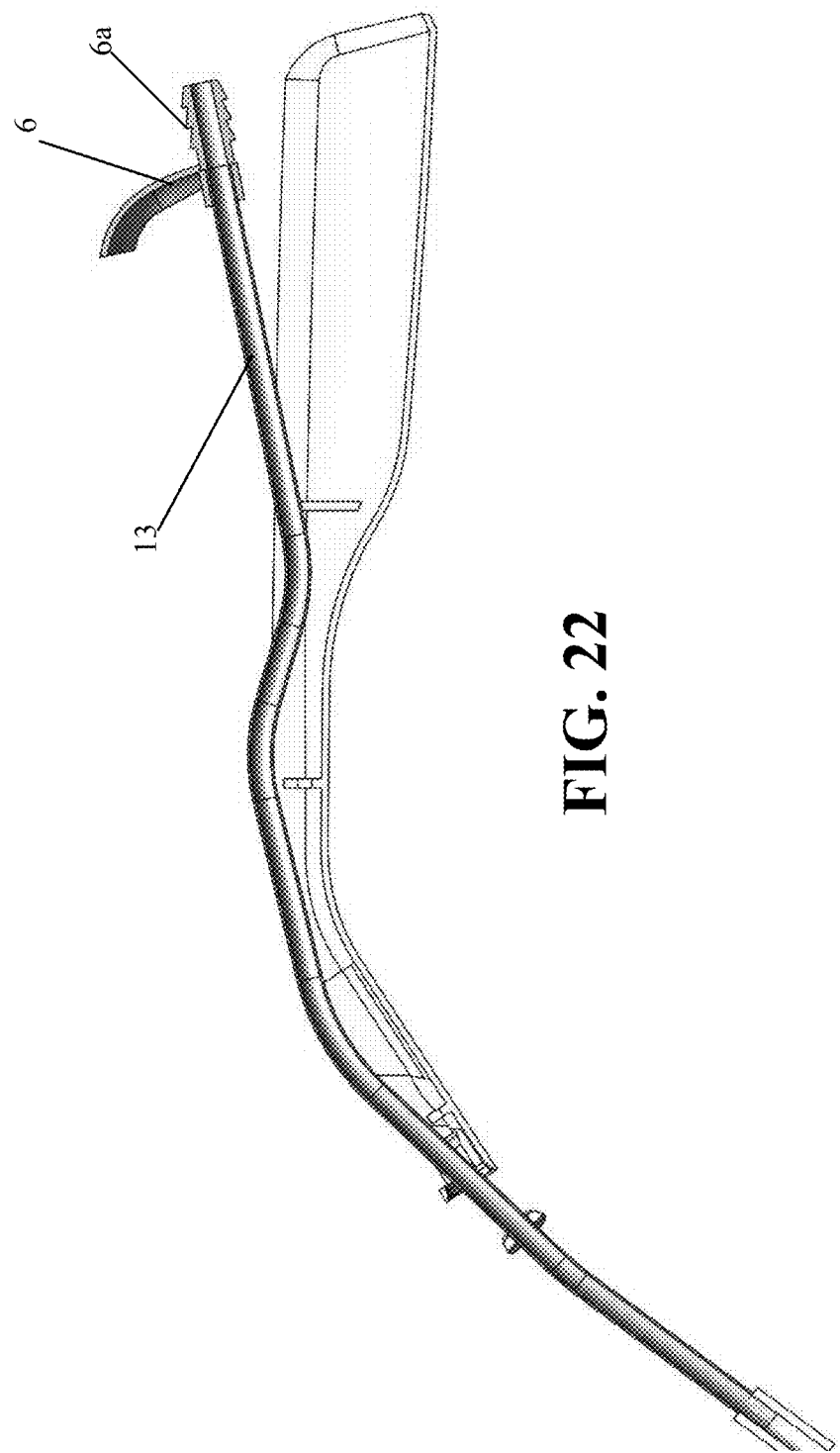
Figure 23:
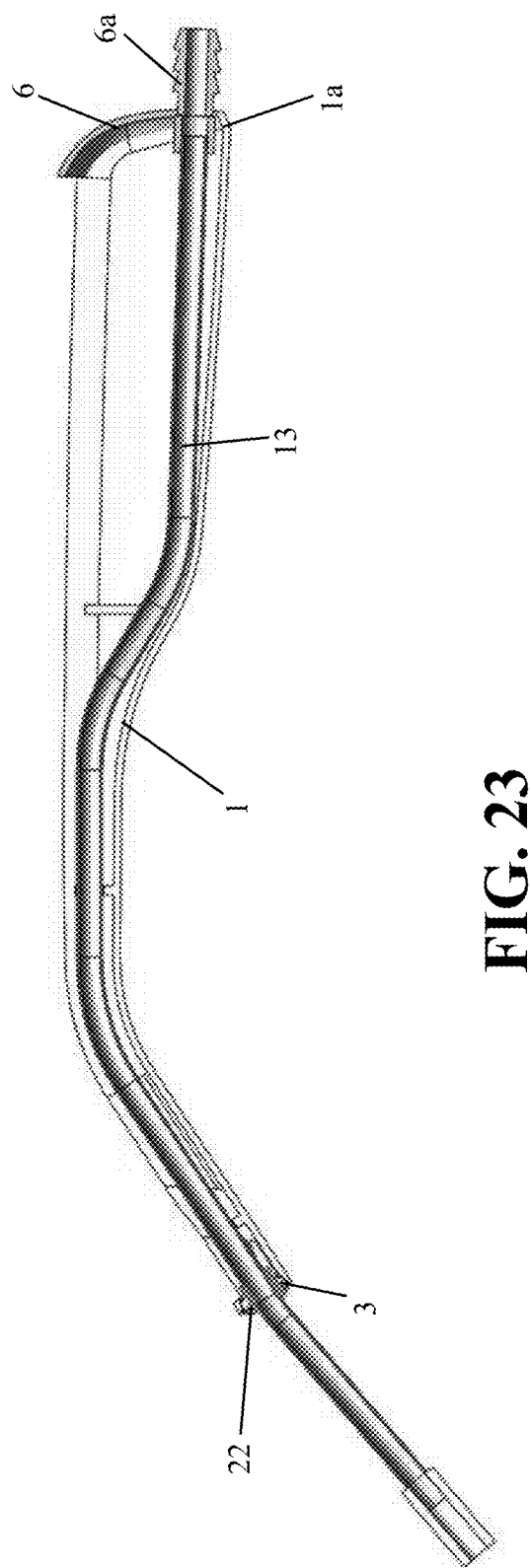

As shown in FIG. 22, the rear cap 6 is attached to the proximal end of the suction tube 13 by inserting the proximal end of the suction tube 13 into the suction port 6*a* of the rear cap 6. In the step shown in FIG. 23, the rear cap 6 is fastened to the proximal end 1*a* of the body 1. In certain embodiments, the edges of the rear cap 6 interlock with the edges of the proximal end 1*a* of the body 1 to provide interlocking features between these components. In addition, or instead of the interlocking features, thread forming screws may be used to fasten the rear cap 6 to the proximal end 1*a* of the body. As shown in FIG. 23, the gasket 22 on the suction tube 13 is partially inserted into the opening in the lens 3 to provide the sealing between the lens 3 and the suction tube 13.

FIG. 24 shows a heat sinking member 8 with a flexible circuit 20 attached thereto. The flexible circuit 20 includes one or more light sources (not shown) and electrical connections 27 which run along the length of the heat sinking member 8 and which have ends 27*a* configured to connect with the PCB controller assembly 12. The electrical connections 27 are encapsulated in or otherwise provided in the substrate of the flexible circuit 20. In the assembly step of FIG. 24, light source mounted on the flexible circuit 20 is positioned within the opening in the distal end of the sinking member 8 and the flexible circuit 20 is attached to the heat sinking member 8 using thermal tape, as described above. The wires 27 may also be attached to the heat sinking member 8 using thermal tape or using other means, or may remain unattached. For the suction device that includes two light sources or two sets of light sources, the other heat sinking member 9 is similarly assembled together with the other flexible circuit with the second light source or second set of light sources. When more than two light sources or sets of light sources are used, each heat sinking member is similarly assembled with the corresponding flexible circuit with the corresponding light source or set of light sources.

As shown in FIGS. 25A and 25B, the heat sinking members 8, 9 are then positioned within the body 1 of the suction device by sliding each heat sinking member 8, 9 into its corresponding position in the body 1. As shown in FIG. 25A, the distal end 1*b* of the body 1 includes ribs or internal projections for positioning the heat sinking members 8, 9 so that an air gap is maintained between the heat sinking members 8, 9 and the suction tube 13. The air gap prevents transfer of heat to the suction tube 13 near the distal end thereof from the heat sinking members 8, 9 and from the light sources 15.

Figure 26A:
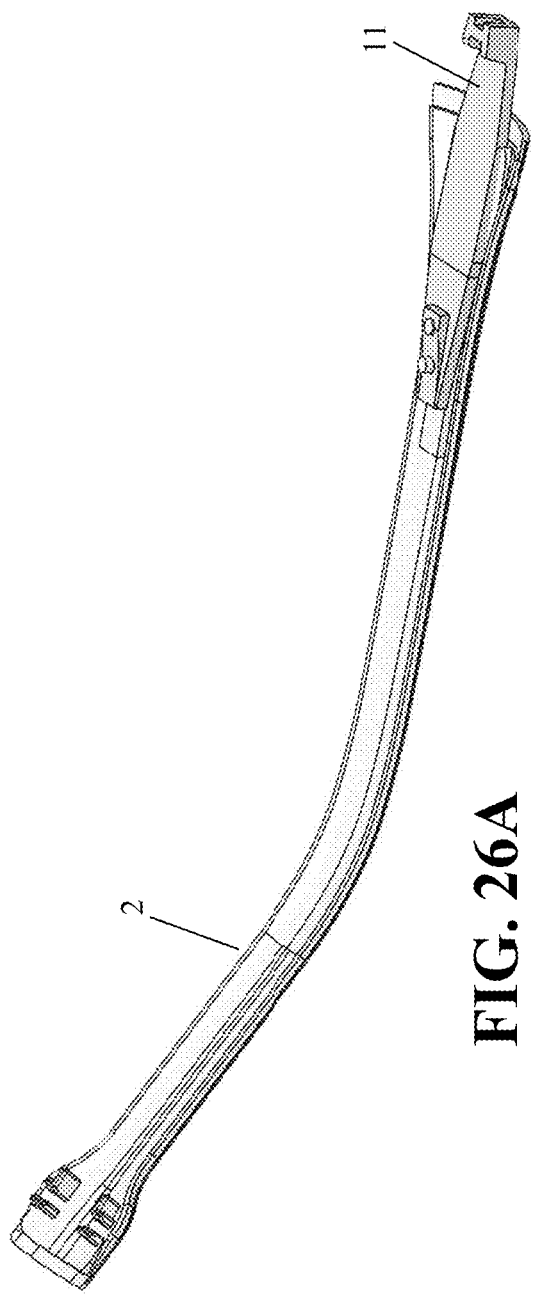
Figure 26B:
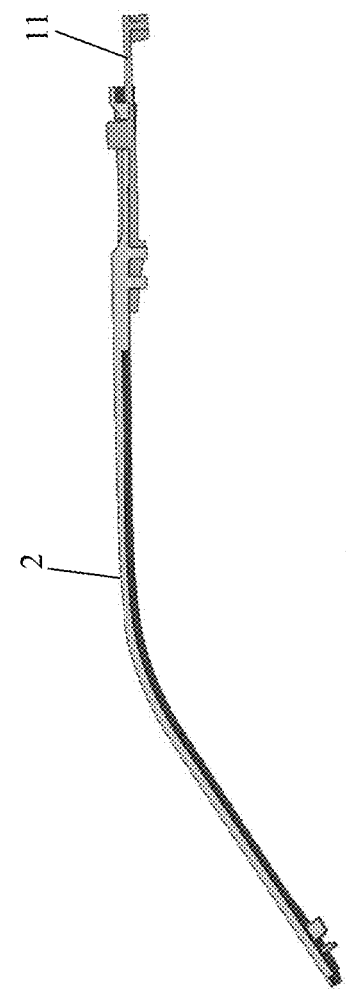
Figure 27:
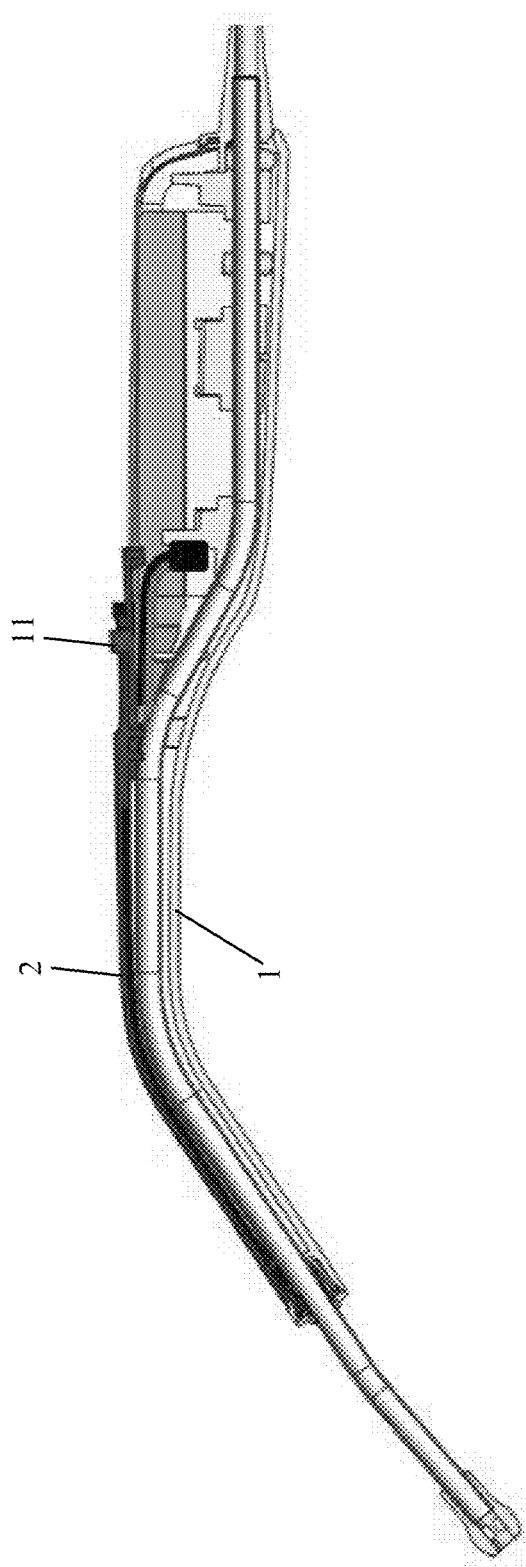

As shown in FIGS. 26A and 26B, the switch 11, which is in the form of the button lever in the present embodiment, is attached to the spine 2 of the suction device. In the present embodiment, the button lever switch 11 is press fitted to the spine 2. The spine 2 with the switch 11 connected thereto is then attached to the body 1 of the suction device as shown in FIG. 27. In one illustrative embodiment, the spine 2 is welded onto the body 1 so as to cover the distal and central portions of the top opening in the body 1. However, in other embodiments, the spine 2 and the body 1 may be configured to interlock with one another so that the spine is slid onto the body 1 or snap fit onto the body 1. Other methods of attaching the spine, such as using adhesive materials, may be used instead or in addition to the other attachment methods.

Figure 28A:
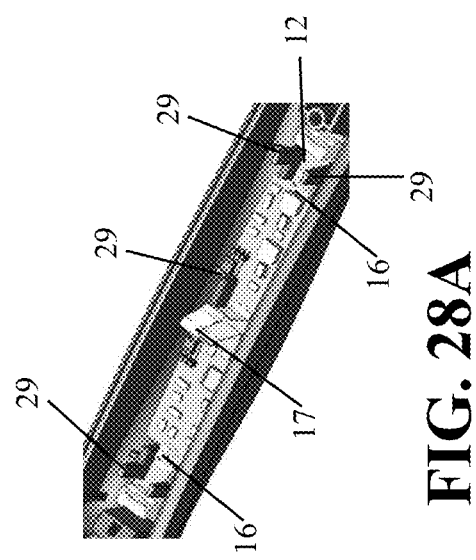
Figure 28B:
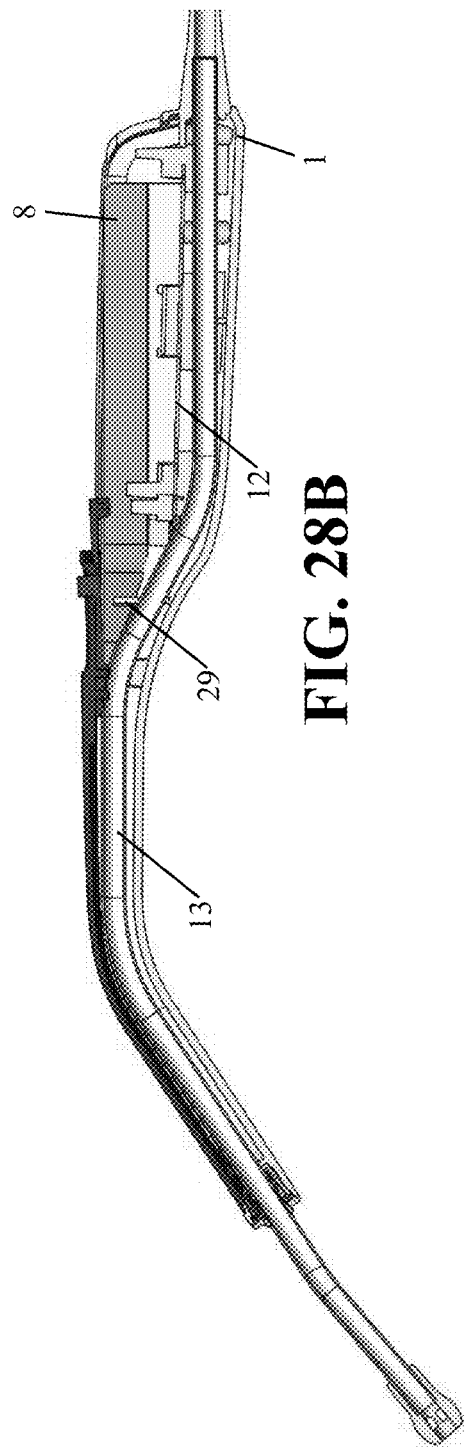

In FIGS. 28A and 28B, the PCB controller assembly 12 is placed into the proximal portion of the body 1. Ribs or internal projections 29 on the inner surface of the body 1 may be used for holding the PCB controller assembly 12 in place. Exemplary projections for positioning the PCB controller are described in U.S. Pat. No. 10,512,519, which is incorporated herein by reference. As shown in FIG. 28B, the PCB controller assembly 12 is positioned on top of the suction tube 13, which extends under the PCB controller assembly 12 all the way to the rear cap 6. In addition, as can be seen in FIG. 28A, the PCB controller assembly 12 includes spring connectors 16 and the central connector 17 for electrically connecting the power source to the PCB controller assembly 12. As shown in FIGS. 28A and 28B, the space formed above the PCB controller assembly 12 is provided for installation of the power source. As also shown in FIG. 28B, the heat sinking member 8 extends along one side of the PCB controller assembly 12, and although not shown, the other heat sinking member 9 extends along the other side of the PCB controller assembly 12.

After the PCB controller assembly 12 is placed in the body 1 of the suction device, the wires 27 connected to the light sources are connected to the PCB controller assembly 12 by plugging into an appropriate connector on the PCB controller assembly 12, as shown in FIG. 29. The power source 7, which includes two batteries, is then installed into the body 1, as shown in FIG. 30. As can be seen, the batteries are inserted into the body 1 so that they are electrically connected to each other by the central connector 17 and so that they are electrically connected to the PCB controller assembly 12 using the spring connectors 16, which are compressed after the batteries are inserted. When the batteries 7 are installed into the body 1, they are positioned so that the PCB controller assembly 12 separates them from the suction tube 13, which extends under the PCB controller assembly 12. In addition, the heat sinking members 8, 9 extend along the sides of the batteries. The internal projections 29 on the inner surface of the body may be used for maintaining an air gap between the PCB controller assembly 12 and the heat sinking members 8, 9 and/or for maintaining an air gap between the batteries 7 and the heat sinking members 8, 9.

Figure 31:
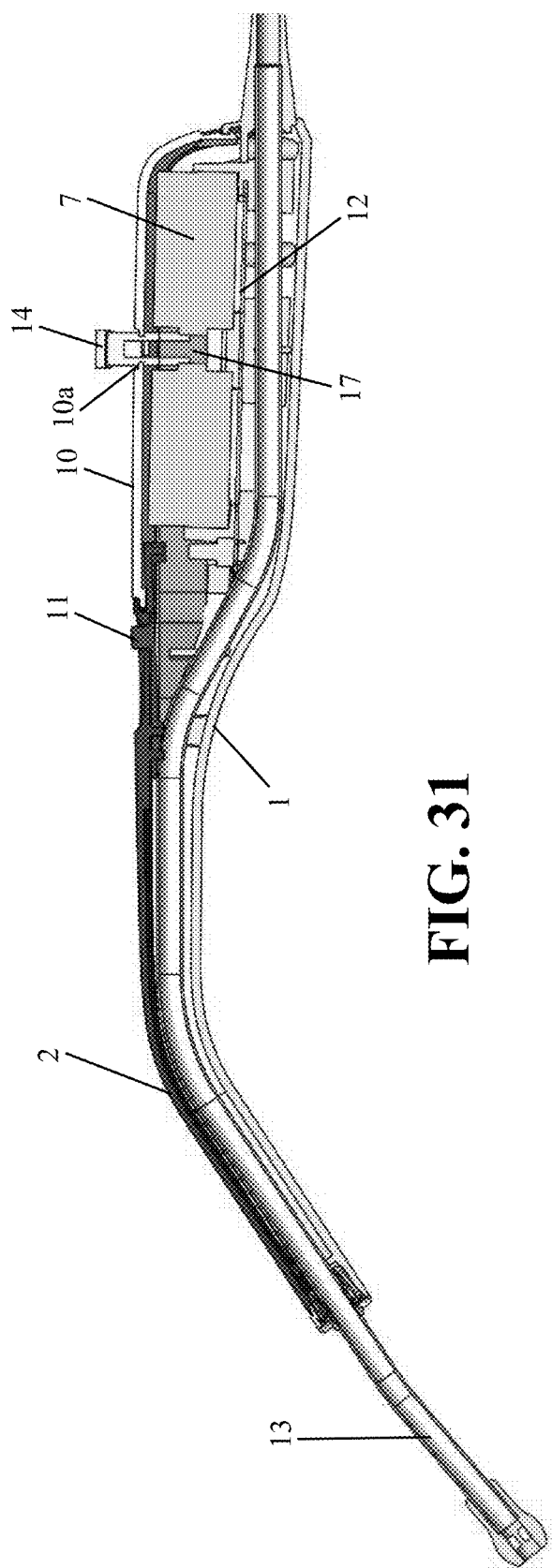

After the power source 7 is installed into the body 1, the battery door 10 and the push-tab 14 are installed in the suction device as shown in FIG. 31. Specifically, the battery door 10 is attached to the body 1 so as to cover the top opening in the proximal portion of the body 1, and a push-tab 14 is inserted into an opening 10a in the battery door 10 so as to electrically isolate the batteries 7 from each other in the storage configuration. As can be seen in FIG. 31, the push-tab 14 slips over the central electrical connector 17 on the PCB controller assembly 12, and is configured so that when the push-tab is in the "storage" position shown in FIG. 31, the push-tab electrically isolates the two batteries 7 from each other, i.e., breaks the circuit, so that the illumination assembly of the suction device cannot be turned ON even if the switch 11 is in the ON position. However, when the push-tab 14 is inserted further into the opening 10a in the battery cover 10 to be in the "use" position, the terminals of the batteries 7 electrically connect with the central electrical connector 17 through an opening in the push-tab 14 so that the illumination assembly can be turned on using the switch 11. In addition, in the "use" position, the push-tab 14 engages with the terminals or other portions of the batteries 7 so that when the battery door 10 is opened, the push-tab 14 forces the batteries 7 to be removed from the body 1 for disposal without requiring any physical contact between the user and the batteries 7.

The suction device shown in FIG. 31 is fully assembled and ready to be used. As mentioned above, the sequence of the specific steps of assembly may be varied in order to adjust for the manufacturing process. For example, assembly steps shown in FIGS. 24 and 26A, 26B may be performed before other steps in the sequence. Other variations may be made to the assembly process as needed.

OTHER EMBODIMENTS

Figures 32A, 32B:
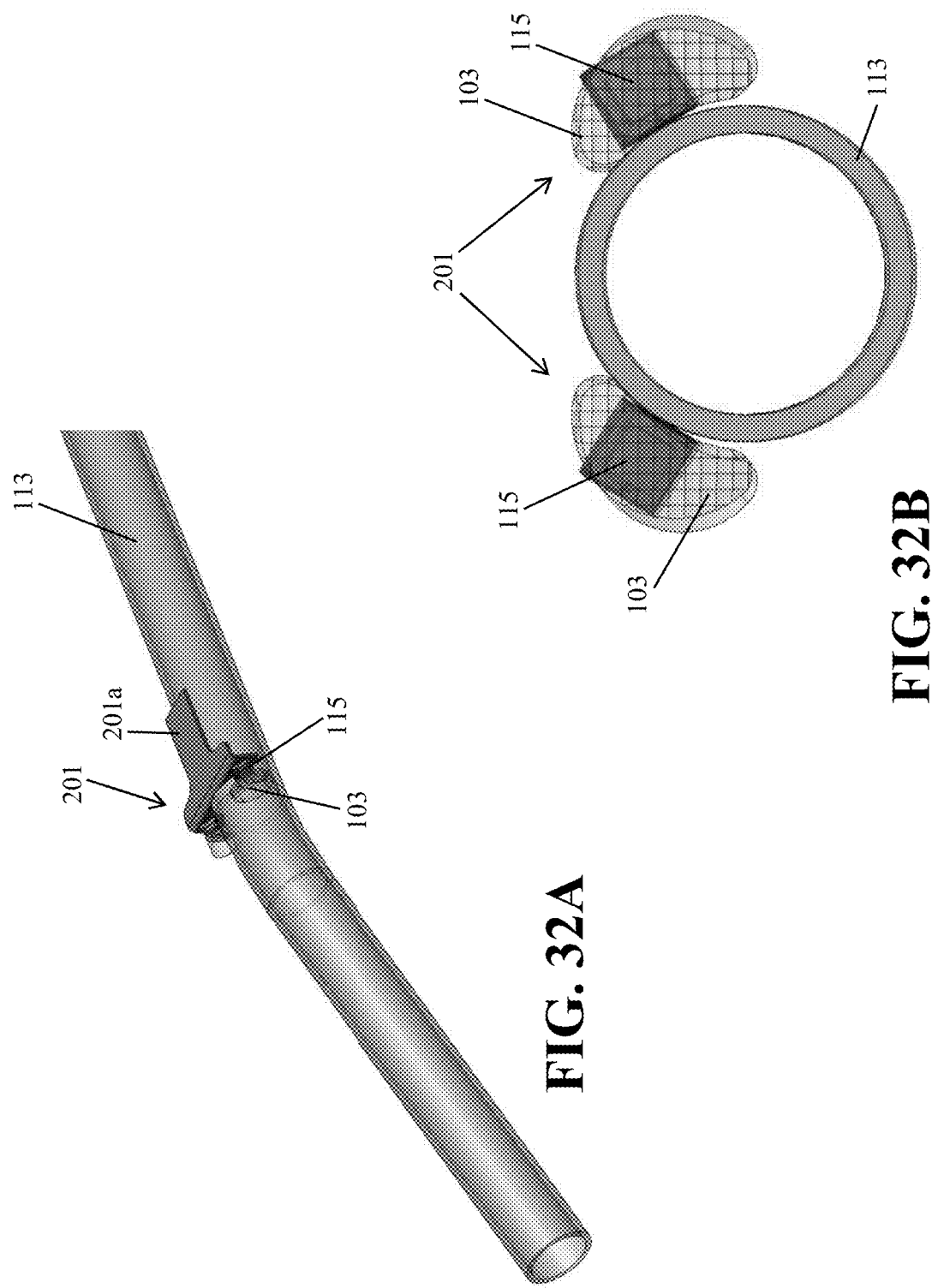
FIGS. 32A-36B show other embodiments and configurations of the suction device of the present invention.

FIGS. 32A-36B show other embodiments of the suction device of the present invention which use a different number of light sources, various positionings of the light sources and different configurations of optical elements. FIGS. 32A-32B show a portion of a suction device 200 including a suction tube 113 and an illumination assembly 201 that includes two light sources 115 and two lenses 103 corresponding to the light sources 115 mounted to the suction tube 113. The light sources 115 may be mounted using a mount 201a, which may be made from plastic or metal and which, in some illustrative embodiments may function as a heat sinking member or may be thermally coupled to the light sources 115 and to one or more further heat sinking members. In FIGS. 32A-32B, the light sources are positioned adjacent different sides of the suction tube 113, offset from the top surface of the suction tube 113, e.g., at around 2 o'clock and 10 o'clock, in order to reduce the size of the suction tube and to optimize its geometry.

The lenses 103 may be similar to those described above with respect to FIGS. 3A-4, e.g., aspheric or toric lenses. In some embodiments, the lenses 103 suitable for use with the illumination assembly 201 of FIGS. 32A-32B and with other embodiments described herein are shown in FIGS. 32C-32F. FIG. 32C is a top view of the lens 103, FIG. 32D is a rear perspective view of the lens 103, FIG. 32E is a rear view of the lens 103 and FIG. 32F is a side view of the lens. As shown, the lens 103 has a convex front surface 103a corresponding to a light output surface and a substantially flat rear surface 103b corresponding to a light inlet surface that receives light from the light source 115. In this illustrative embodiment, the rear surface 103b of the lens includes a microlens array 103b1. The top surface 103c of the lens is convex while the bottom surface 103d of the lens 103 is concave to substantially follow the shape of the suction tube 113.

Figure 32G:
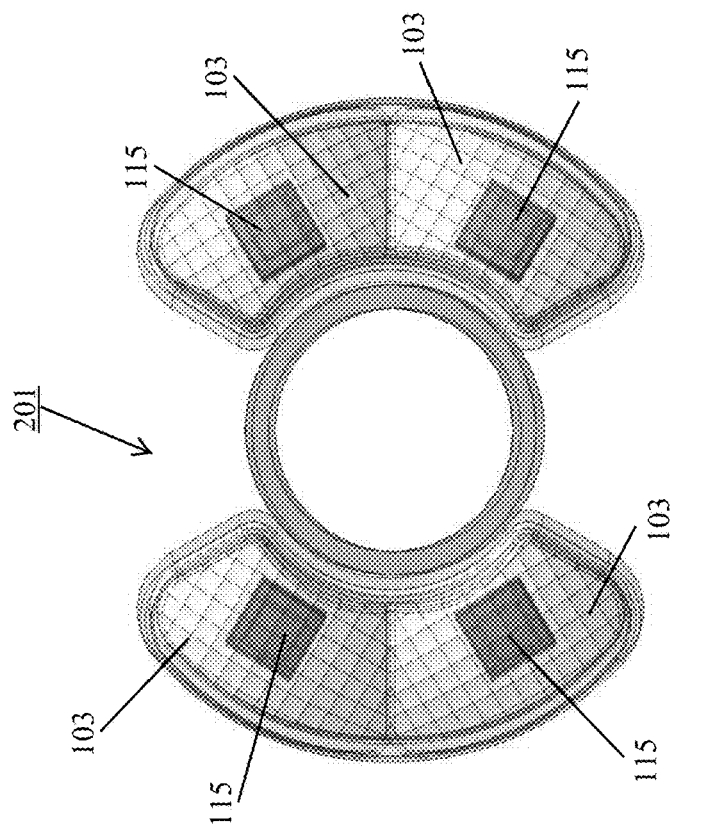
Figure 32H:
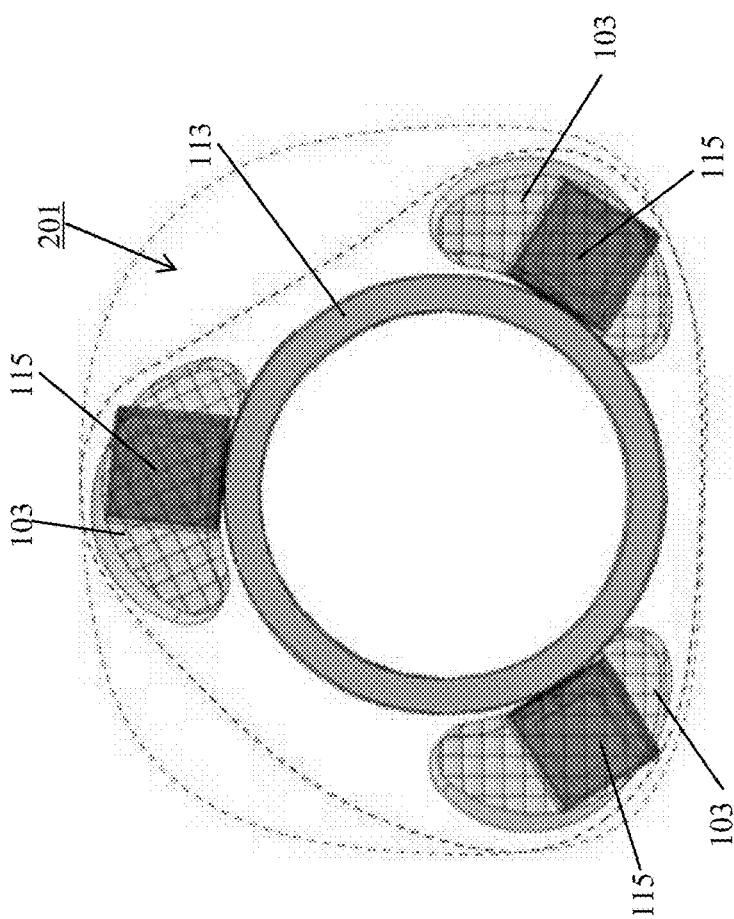

FIGS. 32G and 32H show additional configurations of the illumination assemblies 201 with three light sources 115 and four light sources 115, respectively. In the illustrative configuration of FIG. 32G, three light sources 115 and corresponding lenses 103 are arranged around the suction tube 113 at substantially even intervals. In the illustrative configuration of FIG. 32H, four light sources 115 are arranged adjacent to the suction tube 113 with a pair of light sources 115 arranged adjacent one side of the suction tube 113, e.g., at around 8 o'clock and 10 o'clock, and another pair of light sources 115 arranged adjacent the other side of the tube 113, e.g., at around 2 o'clock and 4 o'clock. In FIG. 32H, four lenses 103 are correspondingly arranged with the light sources 115 so as to direct light to the target area. The configuration of the lenses 103 may be as shown in FIGS. 32C-32F, wherein the light inlet surface of each lens 103 includes a microlens array, or may be as described in other embodiments herein.

Figure 32J:
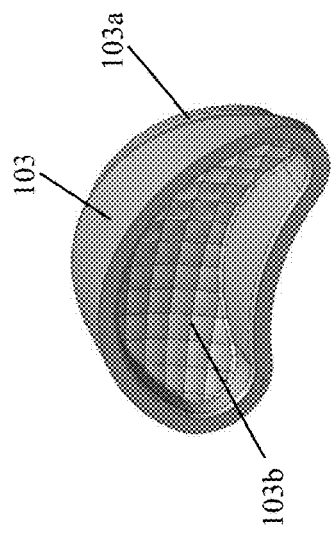
Figure 32K:
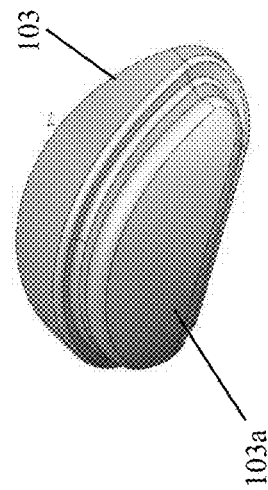
Figure 32L:
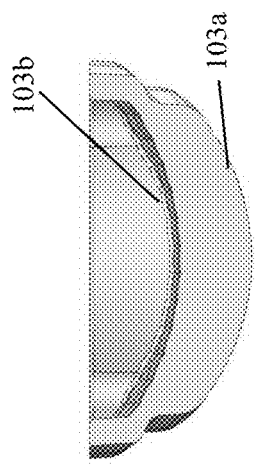
Figure 32I:
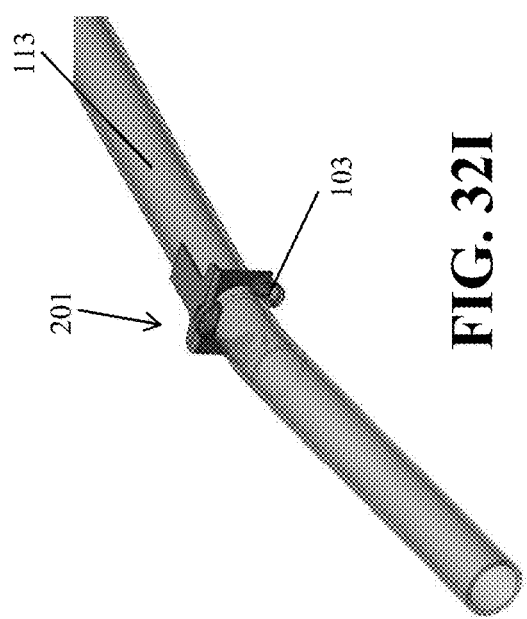

FIG. 32I shows a portion of the suction device 200 that includes the suction tube 113 and the illumination assembly 201 with three light sources 115 and three corresponding lenses 103 mounted adjacent the suction tube 113. FIGS. 32J-32L show another example of a lens 103 that can be used in the illumination assembly of FIG. 32I or in the other illumination assemblies described herein. In this embodiment, the lens 103 includes a convex front surface 103a, as shown in FIGS. 32K and 32L, and a concave rear surface 103b, which is a light inlet surface. As shown in FIGS. 32J and 32L, the concave light inlet surface 103b includes a concave microlens array on its surface. The concave light inlet surface 103b has improved photon collection capabilities, thus improving the efficiency of the lens 103.

In the embodiments shown in FIGS. 32A-32L, the light sources are oriented to emit light substantially along the length of the suction tube 113, i.e., toward the target area. However, FIGS. 33A-36B show additional embodiments of the illumination assembly 301 in which the light sources 215 are oriented to emit light radially with respect to the central axis of the suction tube 213.

Figures 33A, 33B:
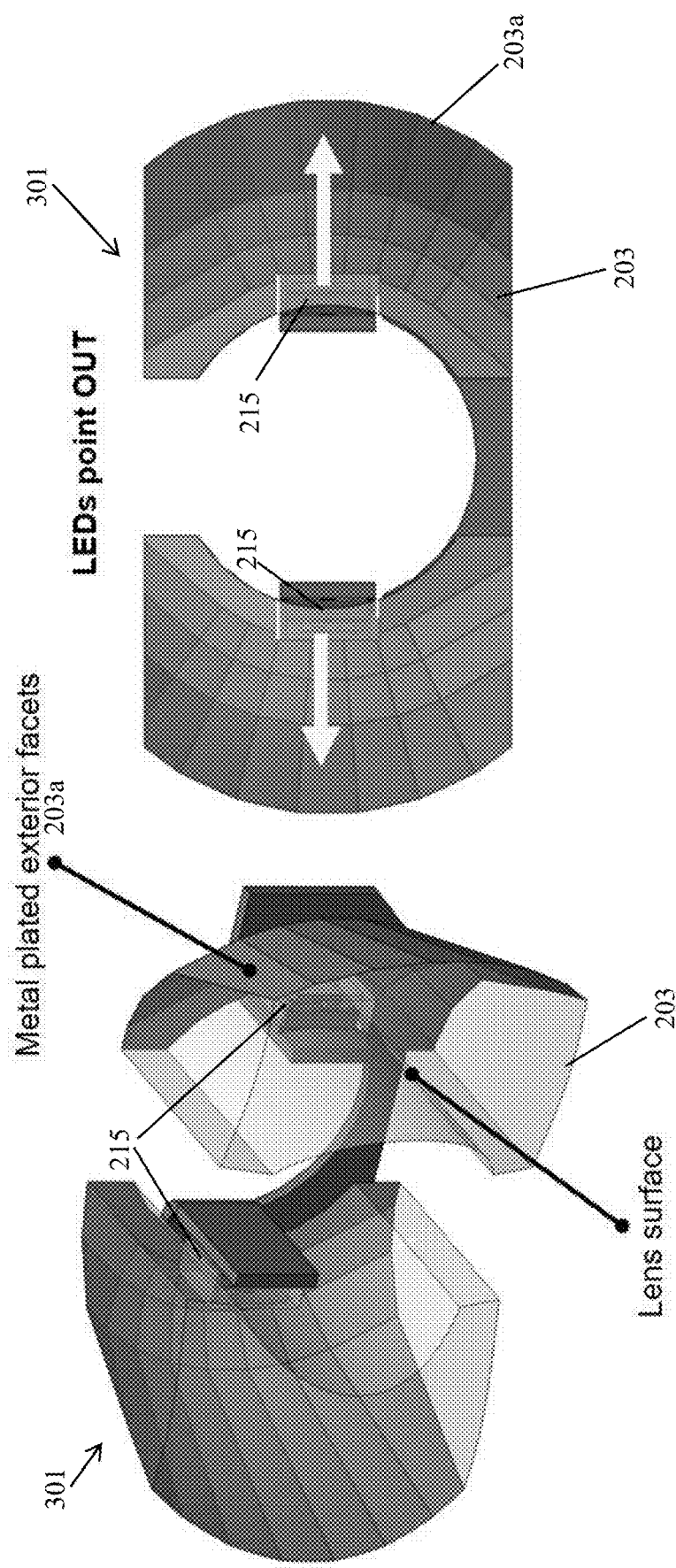

FIGS. 33A and 33B show an illumination assembly 301 which includes two light sources 215, each of which is mounted using a mount or a heat sinking member, similar to the embodiments described above, adjacent opposing sides of the suction tube (not shown). The light sources 215 are oriented away from the suction tube so as to emit light radially and the optical elements for directing and shaping the light beams include lenses or prisms 203 corresponding to the light sources 215 with reflective exterior surfaces 203a provided thereon. As shown, each lens 203 is positioned so as to receive light emitted from the corresponding light source 215. The light emitted from the light source 215 passes through the lens to be reflected by the reflective exterior surface 203a on the lens in a direction toward the target surface, which is in front of the suction tube. The reflected light travels through and is refracted by the respective lens 203 so as to provide illumination with substantially uniform brightness in the target area without shadows.

In the embodiment of FIGS. 33A and 33B, each lens has a convex metal plated exterior surface so as to form a concave reflecting surface for reflecting the light from the light source 215. The metal plated surface may include a plurality of facets in order to properly reflect the light. In other embodiments, instead of using metal plating, a reflective coating may be provided on the exterior surface of the lens. Alternatively, a separate reflector may be used instead of the reflective metal plating or coating.

Figure 33C:
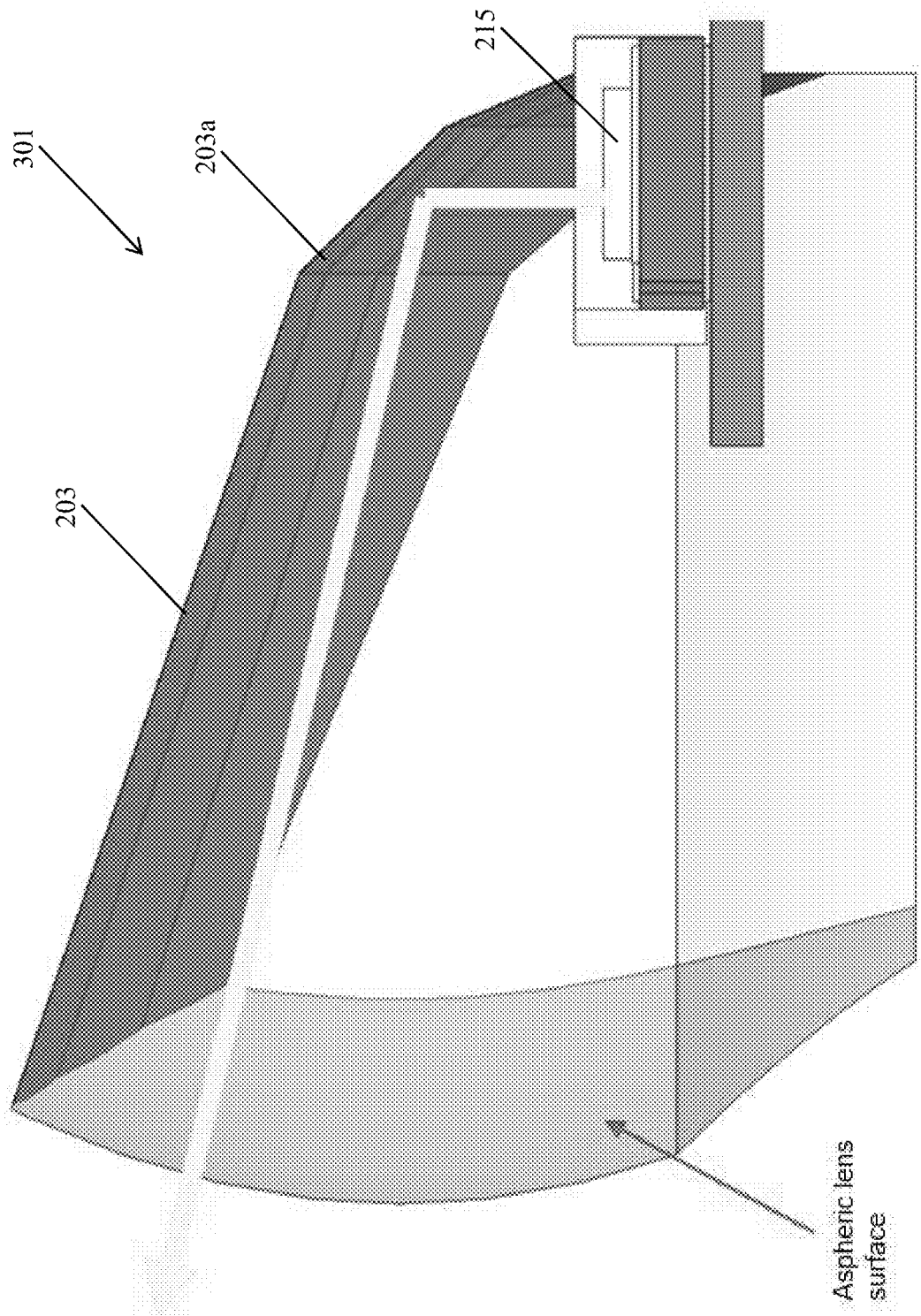

FIG. 33C shows a cross-sectional view of a portion of the illumination assembly 301 of FIGS. 33A and 33B to demonstrate light traveling within the lens or prism 203, wherein the light emitted from the light source 215 is reflected by the reflective coating 203a and directed toward the target area. As shown in FIG. 33C, the illustrative lens or prism 203 has an aspheric front surface, i.e., light outlet surface.

Figure 34A:
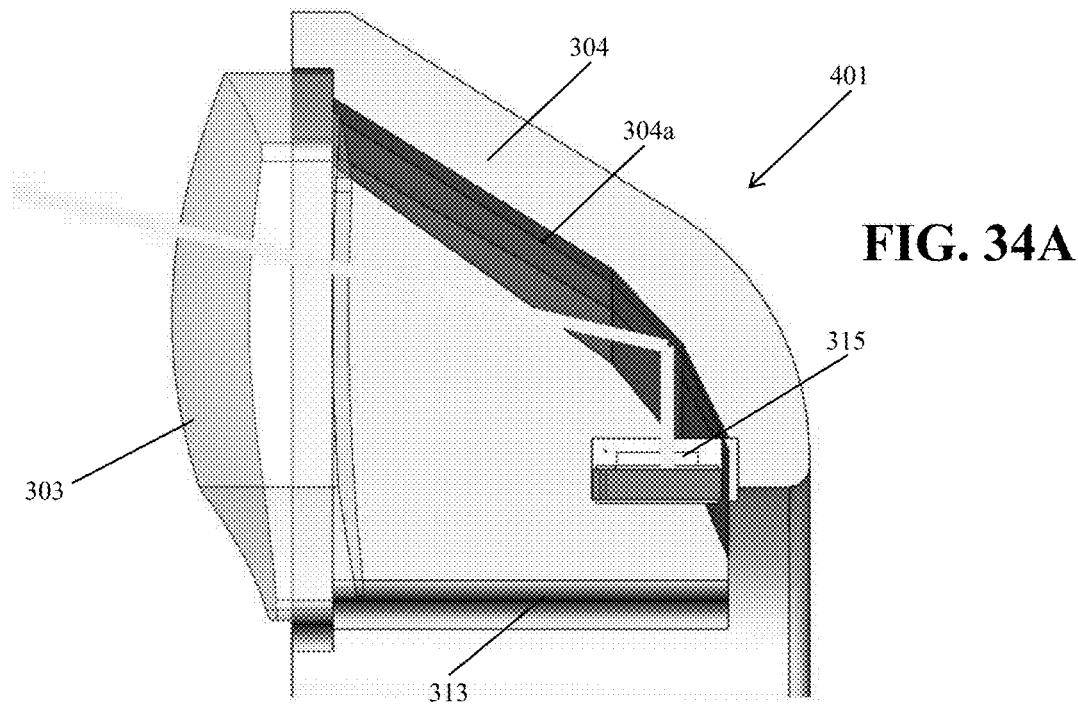
Figure 34B:
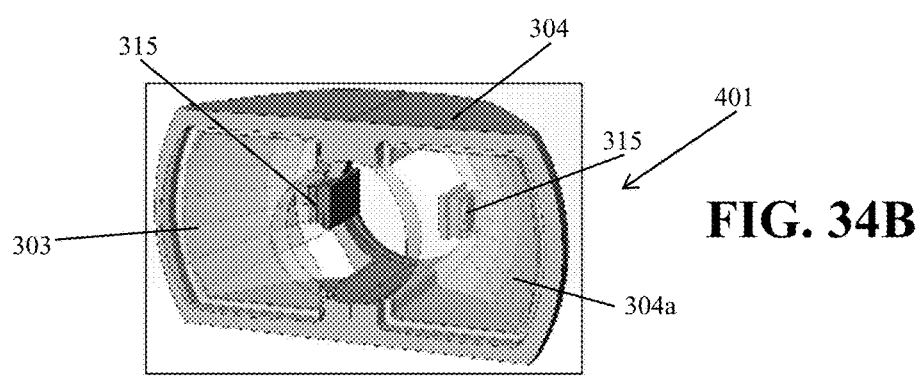

FIGS. 34A-B show an alternative configuration of the illumination assembly 401 in which two light sources 315 are provided within an outer housing 304 and oriented so as to face away from the suction tube 313 and to emit light radially as in the previous embodiment. The outer housing 304 includes a reflective inner surface 304a thereon for reflecting light emitted from the light sources 315. A corresponding lens 303 is provided for each light source for refracting light reflected from the reflective surface. The reflective surface 304a in this illustrative embodiment has a faceted geometry and is molded directly into the housing 304. In some embodiments, the reflective surface 304a may be metal plated or coated onto the inner concave surface of the housing 304. As shown in FIG. 34B, the lenses 303 are provided as separate lenses that are sealingly coupled to the outer housing 304.

Figure 34D:
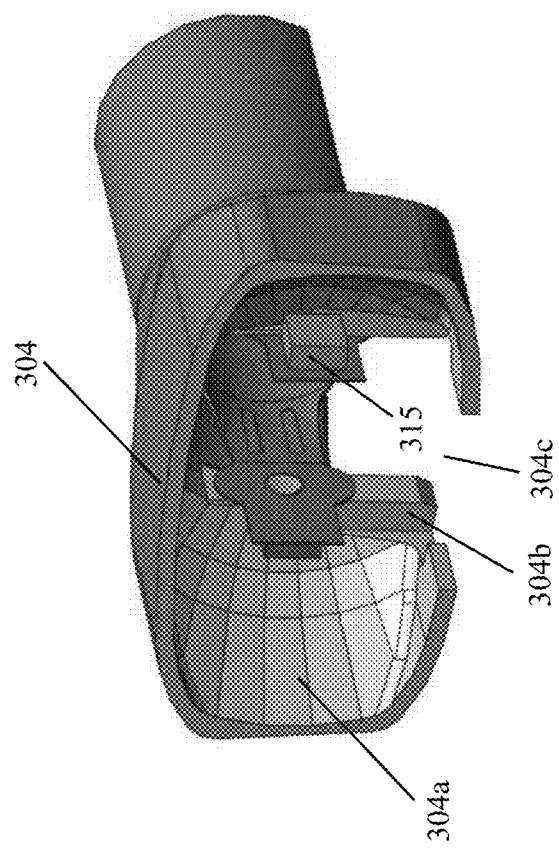
Figure 34C:
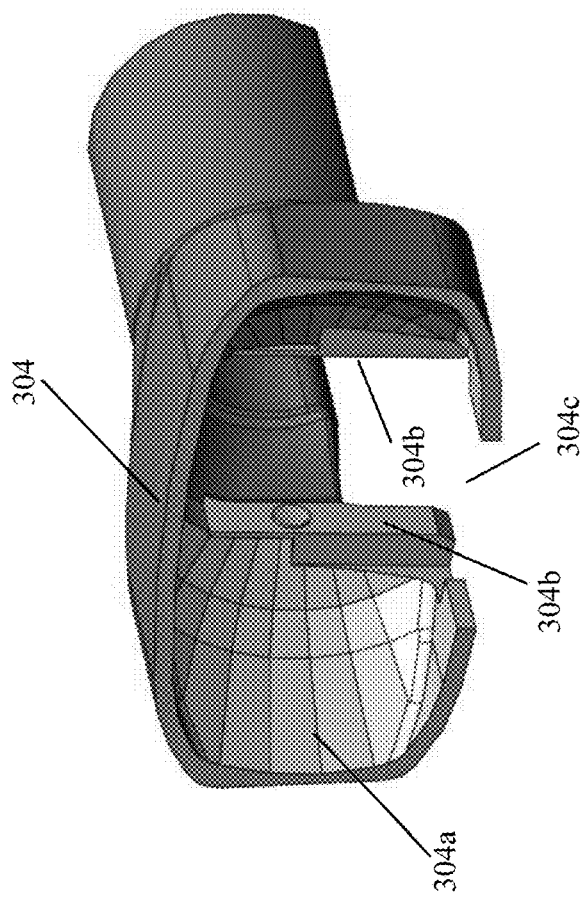

FIGS. 34C and 34D show an exemplary configuration of the outer housing 304 that includes mounting clips 304b for mounting the light sources 315 to the outer housing 304. As shown in FIGS. 34C and 34D, the outer housing 304 has a multi-faceted reflective inner surface 304a which is concave so as to reflect light emitted from the light sources toward the target area. The outer housing 304 also includes a cutout 304c that accommodates the suction tube therein and the mounting clips 304b positioned adjacent each side of the cutout 304c. Each of the light sources 315 is mounted onto a flexible circuit, as described above, and the flexible circuit is then mounted into the mounting clip 304b as shown in FIG. 34D. In some embodiments, the mounting clips 304b may be formed from heat sinking materials and/or thermally coupled to heat sinking plates for dissipating heat generated by the light sources.

Figure 35B:
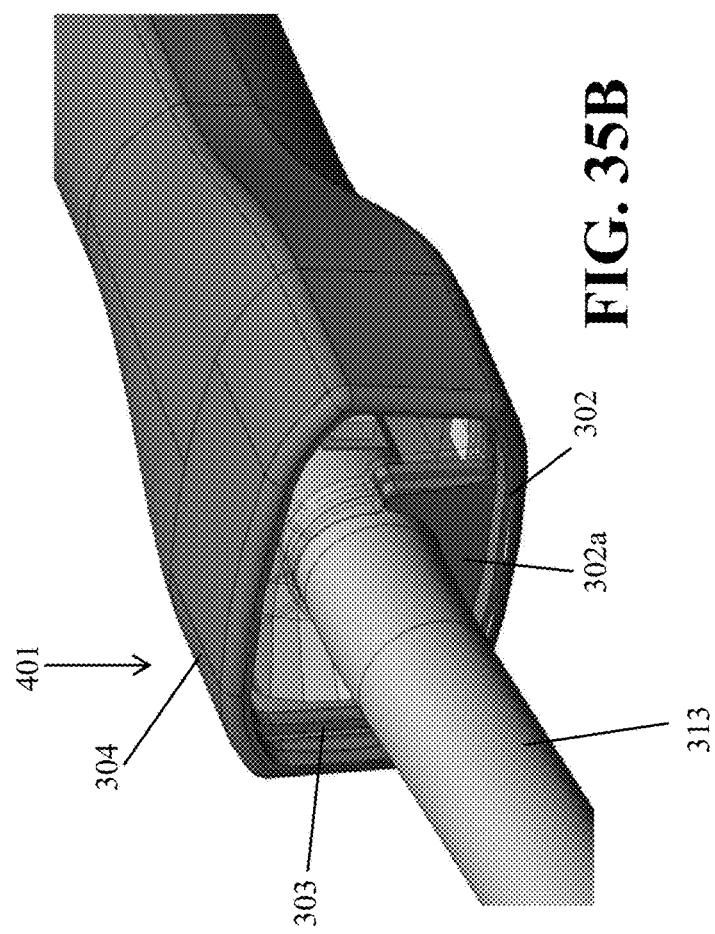
Figure 35A:
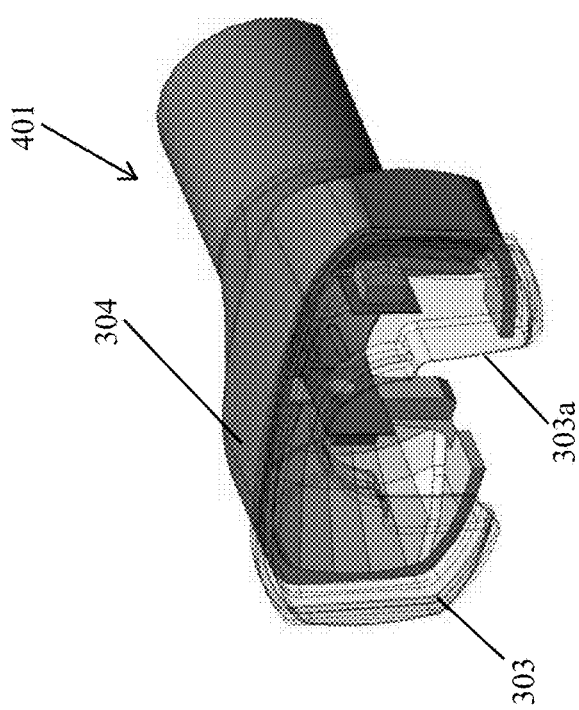

FIGS. 35A-B and 36A-B show exemplary illumination assemblies 401 in which the lenses 303 have different shapes and are sealingly assembled with the outer housing 304 that has a reflective concave surface. In FIGS. 35A-35B, the lens 303 is a one-piece lens with a cutout 303a in the central lower portion thereof so accommodate the suction tube. The lens 303 is welded onto the outer housing 304 or otherwise attached to the outer housing 304 in a fluid-tight manner. After the suction tube 313 is assembled into the illumination assembly, a spine 302 or a cover for the outer housing 304 is attached to the outer housing 304 so as to seal the illumination assembly 401. As shown in FIG. 35B, the spine or cover 302 includes a tongue 302a which fits into the cutout 303a in the one-piece lens 303.

Figure 36B:
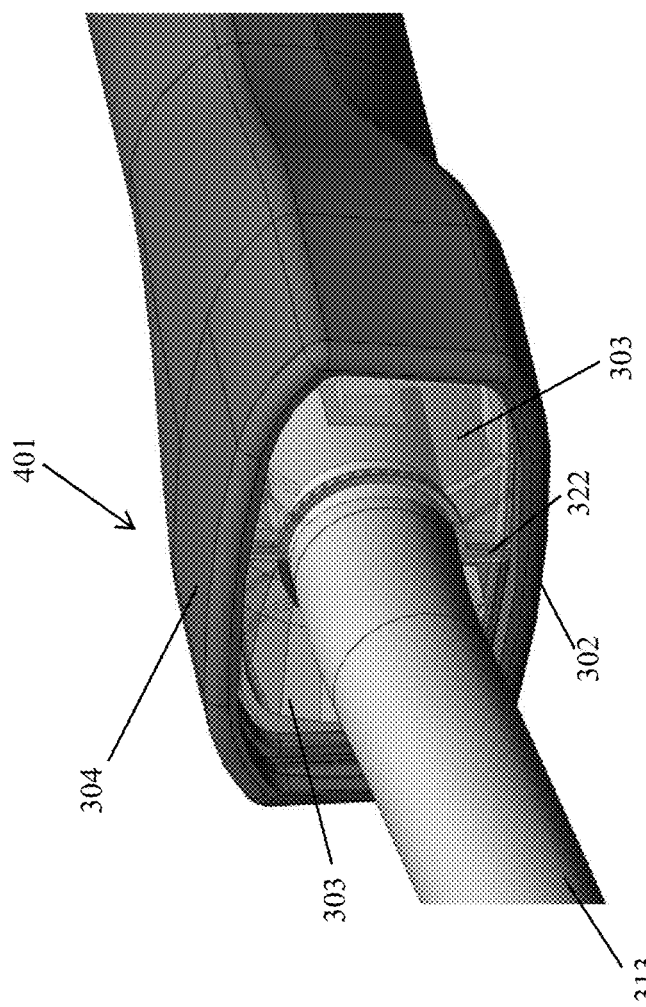
Figure 36A:
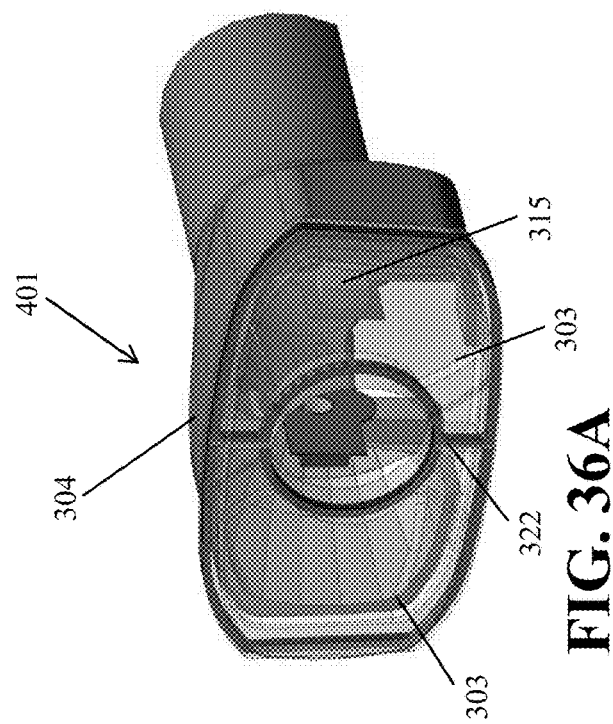

In the illustrative embodiment of FIGS. 36A and 36B, two separate lenses 303 are provided for the illumination assembly and a gasket seal 322 is provided for sealing around the perimeter of the lenses 303 to the outer housing 304 and to the suction tube 313 and for sealing the space between the two lenses 303. With this construction, the tongue portion of the spine or cover 302 is eliminated, which also eliminates possibility of any light blocking.

Although FIGS. 33A-36B show illumination assembly arrangements with two light sources, it is understood that these arrangements may be varied to include additional light sources, similar to the other embodiments described above. Thus, for example, the illumination assembly embodiments of FIGS. 33A-36B may be modified to include three or four light sources distributed around the suction tube or may be modified to include multiple light sources at each location around the suction tube.

Flow Control Assemblies

The suction devices described herein above, as well as other suction devices that include other illumination assemblies or which do not include any illumination assembly, may include a flow control assembly for controlling suction through the suction tube. FIGS. 37A-52B show different embodiments of flow control assemblies.

Figure 37A:
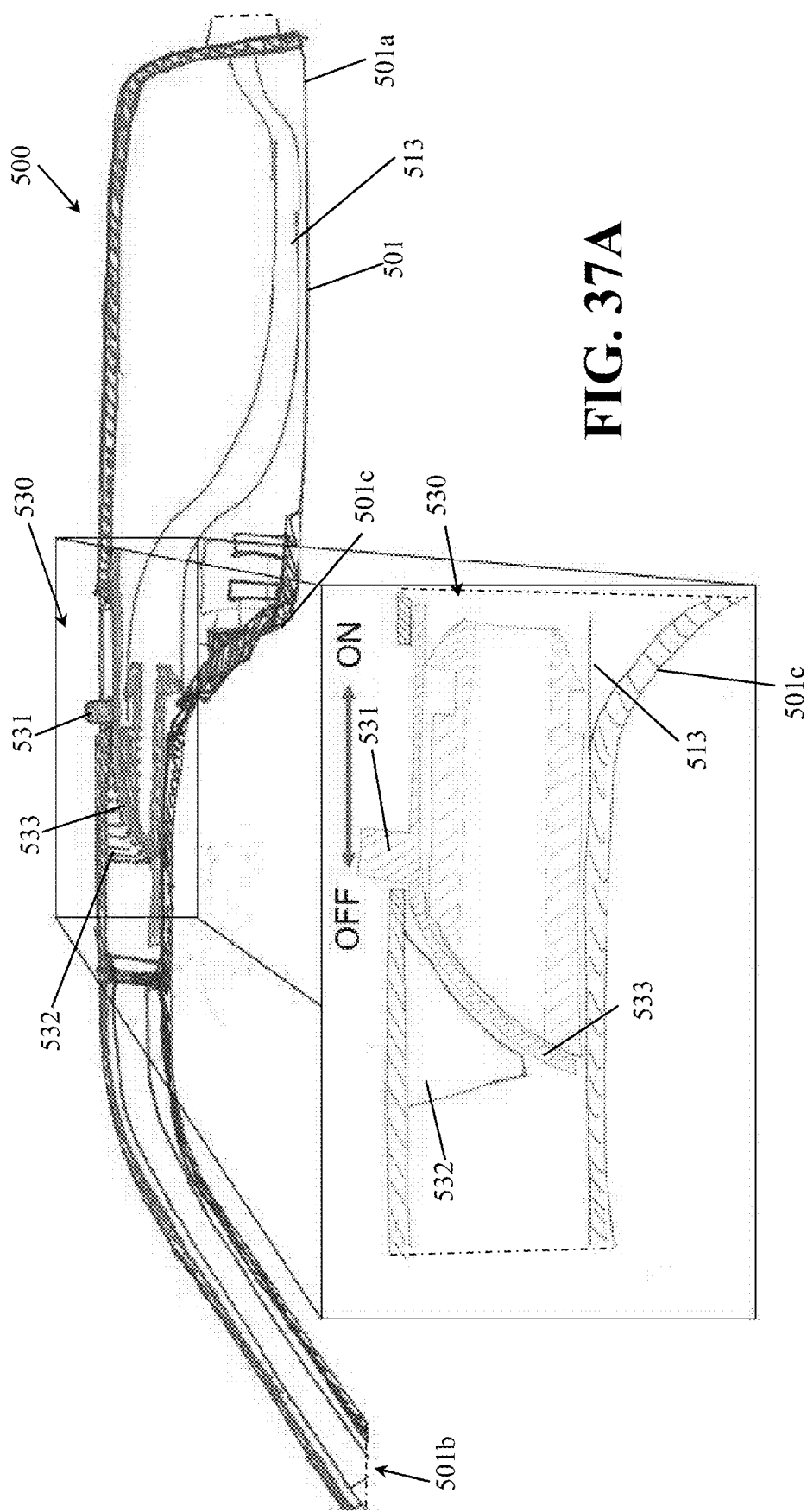
Figure 37B:
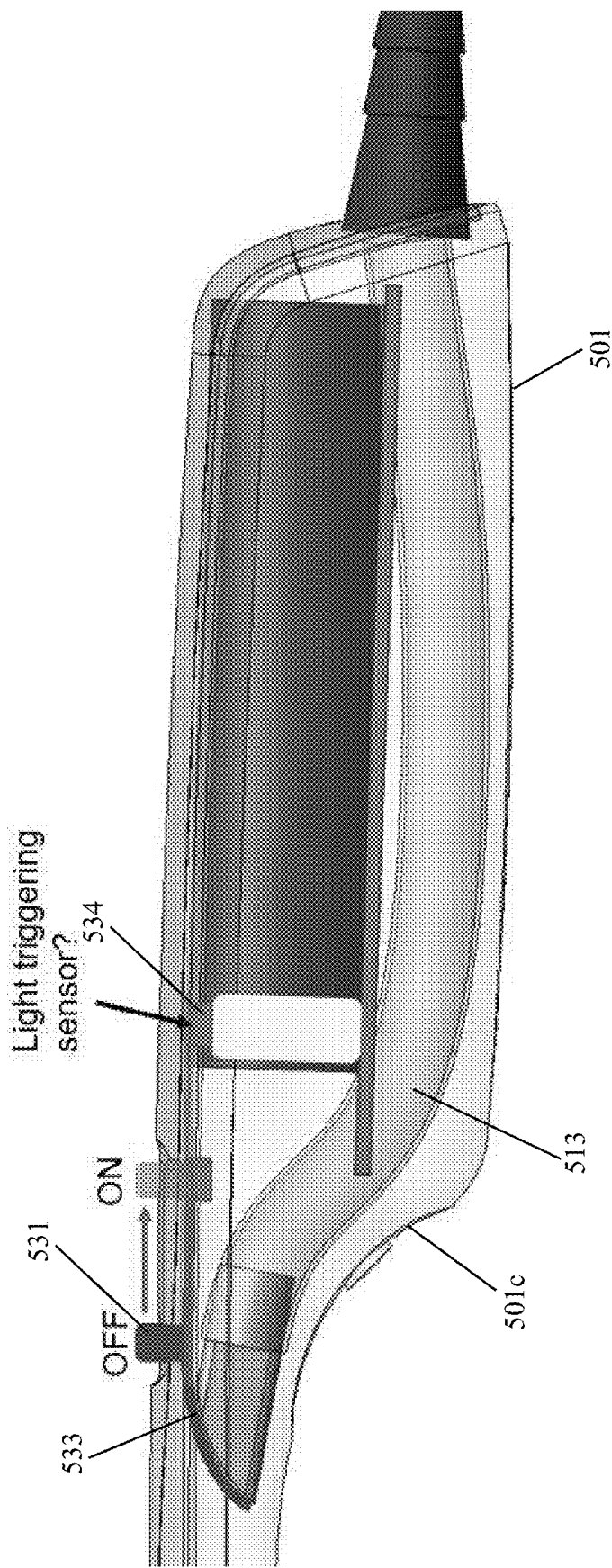

FIGS. 37A-37B show a suction device 500 with a flow adjustment mechanism 530 for controlling suction through the suction tube 513. The suction device 500 includes a body 501, similar to the suction devices described herein above, and the body of the suction device 500 includes a proximal end 501a, a distal end 501b and a neck portion 501c which is an area where the span of the body narrows from a wider span (handle portion) to a narrower span in a distal direction. The flow adjustment mechanism 530 in this illustrative embodiment is provided in the neck portion 501c of the body 501. The flow adjustment mechanism 530 extends through the suction tube 513 and has an operating member 531, such as a button, a slider or a trigger pivot, provided on the exterior of the body 501 to enable control by the user.

As shown in FIG. 37A, the flow control assembly 530 includes a stationary projection 532 within the suction tube 513, which partially blocks the flow of air within the suction tube 513. The flow control assembly 530 also includes a movable barrier or partition 533 which has a shape conforming to the stationary projection 532 so that when the movable barrier 533 is adjacent the stationary projection 532, these two structures block the flow of air through the suction tube 513. The movable barrier 533 is mechanically coupled to the operating member 531 which can move between an OFF position and an ON position. When the operating member 531 is in the OFF position, as shown in FIG. 37A, the movable barrier 533 is adjacent to the stationary projection 532 and the suction through the suction tube 513 is blocked. When the operating member 531 is moved to the ON position, the movable barrier 533 is moved away from the stationary projection 532 or removed from the flow path in the suction tube 513 so that suction is turned ON. As shown in FIG. 37A, the operating member 531 is a slider which is coupled to the movable barrier and when the slider 531 is moved to the ON position, this coupling causes the movable barrier 533 to be removed from the flow path in the suction tube. By sliding the slider 531 between the OFF and ON position, suction strength can be controlled over a continuous range so that suction is strongest when the slider 531 is all the way in the ON position. Specifically, the slider can be positioned anywhere between the ON and OFF positions to maintain the suction at the corresponding flow level in order to enable to continuously vary the flow level.

In some embodiments, a second operating member, such as a button or a potentiometer or a button slide switch, for controlling the illumination assembly is provided on the body separately from the operating member 531 for controlling the suction. For example, the second operating member may be provided on the opposite side of the body 501 from the slider 531 in the neck portion of the body. In other embodiments, the operating member 531 for flow control is integrated with the illumination assembly control. FIG. 37B shows an exemplary embodiment in which a light triggering sensor 534 is provided within the body 501 of the suction device which is triggered by the slider 531 being brought into the ON position, or near the ON position. In this embodiment, when the slider 531 is brought into proximity with the light triggering sensor 534 by sliding the slider towards the ON position, the illumination assembly is turned ON so as to provide illumination. When the slider 531 is brought into the OFF position, the illumination assembly is caused to turn OFF.

In some embodiments, instead of the stationary projection and the movable barrier, the flow control assembly includes a stopcock mechanism or another type of valve in the suction tube which can be operated between an OFF and an ON position using a turning handle or similar operating member. In certain embodiments, the stopcock mechanism or valve operating member is provided in the neck portion of the body of the suction device.

The flow control assembly of FIGS. 37A-B and the stopcock mechanism described above may be used with any type of suction tube, e.g., a flexible, pinchable tube or a metallic tube. In other embodiments, the flow control assembly is specifically adapted for use with a flexible tube as the suction tube, so as to pinch the suction tube closed to prevent air flow in the OFF position, and to open the suction tube to allow suction in the ON position.

FIG. 38C shows a pinch clamp 635 which is used in the flow control assembly 630 of FIGS. 38A-38B. FIGS. 38A and 38B show the view of the flow control assembly 601 from the outside of the body 601 of the suction device. In FIG. 38C, the pinch clamp 635 includes a first arm 635a and a second arm 635b, and the second arm 635b includes an engagement recess or tooth 635c. In addition, the pinch clamp 635 has one or more pinching projections 635d which pinch the tube when brought closer together. The first arm 635a of the pinch clamp 635 can be operated by a user, as shown in FIG. 38A by pressing down on the first arm 635a so as to engage the tip of the first arm 635a with the engagement recess 635c on the second arm 635b. When the first arm 635a is engaged with the engagement recess 635c, the second arm 635b can be operated by a user to disengage the engagement recess 635c from the first arm 635a, as shown in FIG. 38B.

Figures 38D, 38E, 38F:
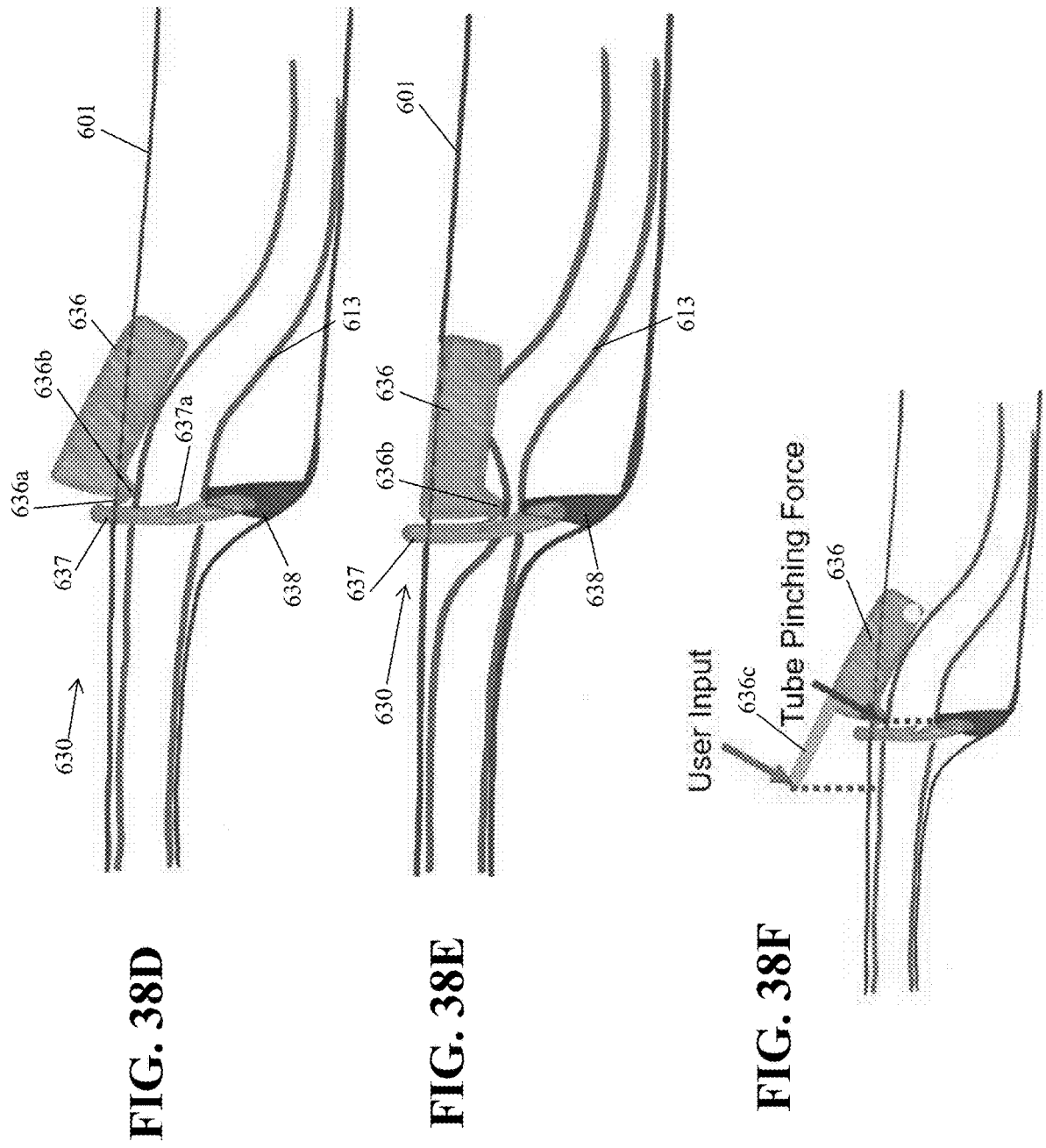

The flow control assembly of FIGS. 38A-B and the pinch clamp 635 of FIG. 38C can be modified as shown in FIGS. 38D-38E and in FIG. 38F to include separate first and second arms 636 and 637 which are configured to releasably engage with one another and which are configured to pinch the suction tube when engaged with one another. As shown in FIGS. 38D and 38E, the first arm 636 includes an engagement tooth 636a for engaging with a recess 637a or tooth formed on the second arm 637 and a pinching projection 636b for pinching the suction tube 613 against a stationary projection 638 when the first arm 636 is engaged with the second arm 637. The first and second arms 636, 637 are engaged by pushing down on the first arm 636 projecting from the body 601 of the suction device and disengaged by pushing the second arm 637 in a direction away from the first arm 636. In FIGS. 38D and 38E, the second arm is mounted to the stationary projection 638 within the body of the suction device. In the embodiment shown, the second arm 637 is hollow or includes a through opening therein that allows the suction tube 613 to pass through it.

The flow control assembly 630 of FIGS. 38D-38E is further modified in FIG. 38F by providing an operating lever 636c on the first arm 636 to make operation of the flow control assembly easier by requiring less input force by the user. The lever 636c may be offset to the side from the second arm 637 in order to allow the user to easily operate the second arm 637 to release the engagement between the two arms. Although in FIGS. 38A-E, the second arm includes one engagement recess or engagement tooth, in other embodiments, multiple recesses or teeth may be provided on the second arm in order to provide different positions of engagement between the first and second arms.

FIGS. 39A and 39B show another embodiment of a flow control assembly 730 that includes a detent slider mechanism. As shown in FIGS. 39A-39B, the flow control assembly 730 includes a movable slider 735 and a pinching arm 736 which moves between an open position and a pinched closed position based on the movement of the slider 735. The slider 735 has an operating member 735a, which can be in the form of a projection, that extends outside of the body 701 and which can be operated by a user to move the slider 735 between an OFF position, which is shown in FIG. 39B and an ON position, which is shown in FIG. 39A. The slider 735 also has a ramp 735b that gradually causes the pinching arm 736 to move toward the pinched closed position as the slider 735 slides between the OFF position and the ON position. In the OFF position, an engagement recess or plateau surface 735c on the slider 735 engages with the pinching arm 736, which pinches the suction tube 713 closed as shown in FIG. 39B. This detent mechanism holds the slider 735 in the OFF position relative to the pinching arm 736. As shown in FIGS. 39A-39B, in some embodiments, a stationary projection 737 may be provided within the body 701 against which the suction tube 713 is pinched by the pinching arm 736.

Figure 46A:
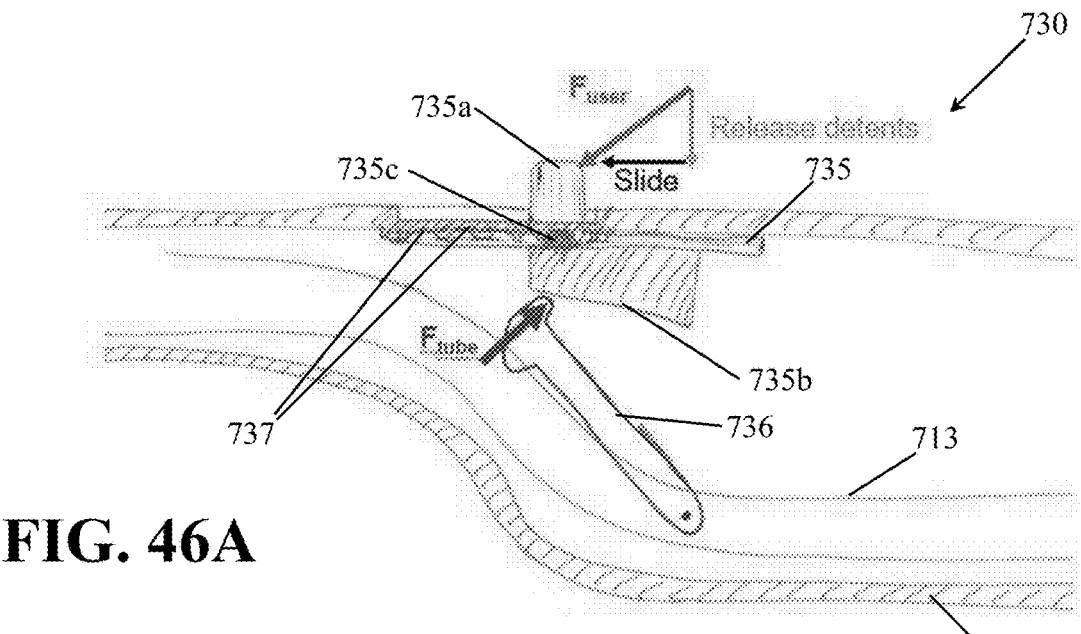
Figure 46B:
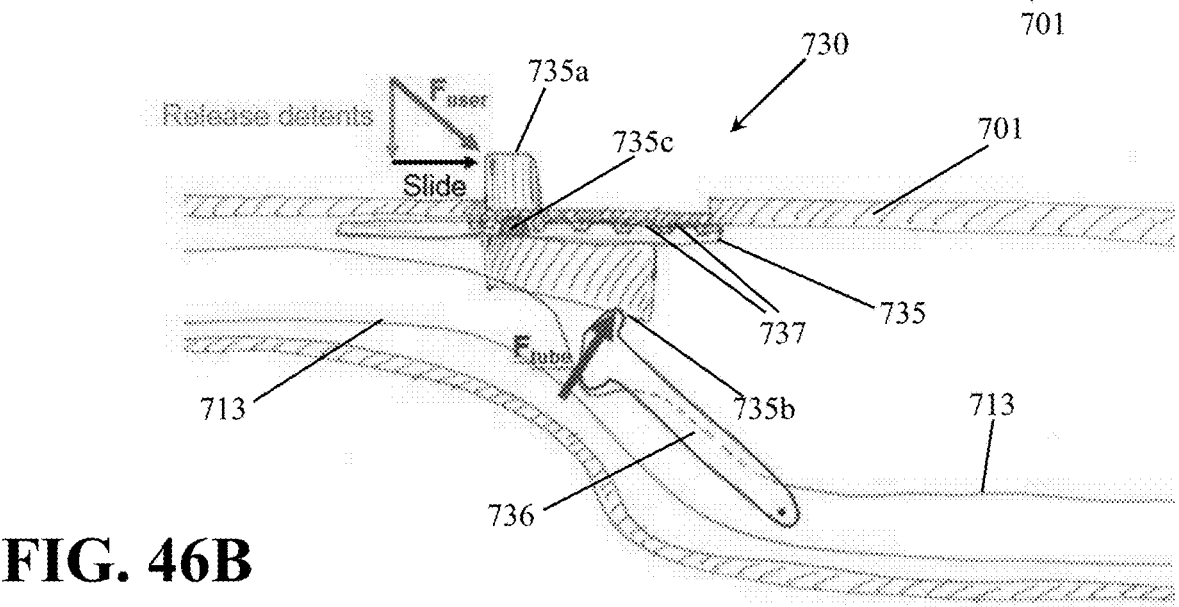

FIGS. 46A-46B show another exemplary arrangement of a flow control assembly 730 that uses a detent slider mechanism. FIG. 46A shows the flow control assembly 730 in the ON position that allows maximum suction through the suction tube 713, while FIG. 46B shows the flow control assembly 730 in the OFF position in which the suction tube 713 is pinched closed. As shown, the flow control assembly 730, similar to FIGS. 39A-39B, includes a movable slider 735 which slides between ON and OFF positions, e.g., slides front to back between the ON and OFF positions, and a pinching arm 736, which moves to open and pinch closed the suction tube 713 based on the sliding motion of the movable slider 735. As in FIGS. 39A-39B, the slider 735 of this example has the operating member 735a, such as a projection, that can be operated by a user, and a ramp 735b that causes the pinching arm 736 to gradually move toward or away from the suction tube 713. In the example of FIGS. 46A-46B, the slide 735 includes a projection 735c which is configured to engage with a plurality of recesses 737 provided along a portion of the body 701 so that the slide 735 can be locked at different positions between the OFF and ON positions to control suction strength. The length of the slider 735 and the pitch of the inclined plane of the ramp 735b may be varied in order to vary the amount of force required to move the operating member 735a from one position to another. For example, a longer slider 735 with a shallower pitch of the inclined plane of the ramp 735c will require a smaller force by the user to move the operating member 735a.

Figure 40:
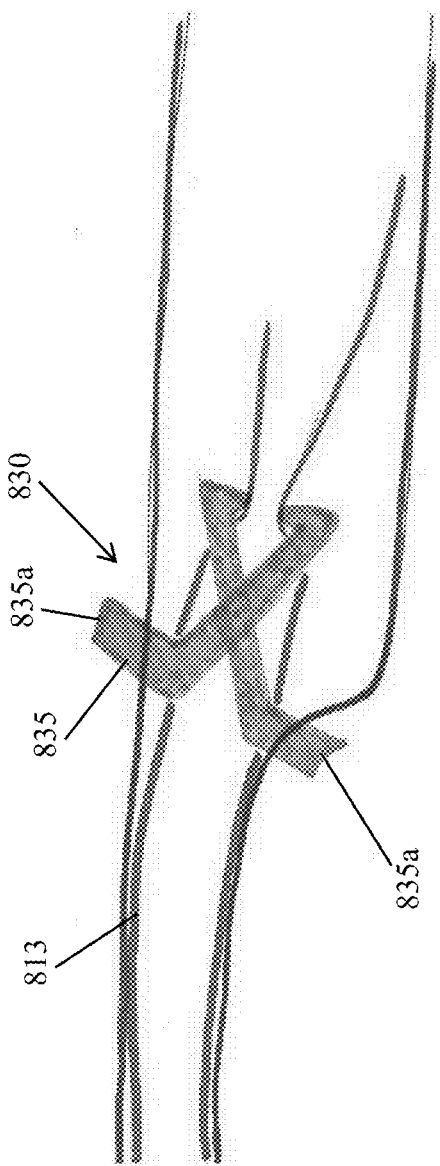

FIG. 40 shows another tube pinching flow control mechanism 830 which uses a scissor pinching clamp 835 having two arms configured to be operated between an open position and a closed position using two buttons or levers 835a. When the buttons or levers 835a are operated to pinch the suction tube 813, the opposite ends of the respective arms are brought closer together so as to pinch the suction tube 813 from opposite sides. The pivot location between the two arms of the clamp 835 may be adjusted in order to provide sufficient height of the buttons or levers 835a and in order to adjust input force required by a user.

FIGS. 41A-41D show a flow control assembly 930 that uses a rocker pinch valve 935 and a spring 936, which is biased between two positions and which has a pinching member 936a, in a form of a projection, cylindrical pin, plate, etc., attached thereto. A rocker pinch valve manufactured by the Z-Man Corporation is an exemplary rocker pinch valve suitable for use in the flow control assembly 930. As shown in FIGS. 41A-41D, the rocker pinch valve 935 is engaged with the spring 936 so that in a first position (ON position) of the rocker 935, shown in FIG. 41A, the spring 936 is biased in a direction away from the suction pipe 913 and in a second position (OFF position) of the rocker 935, shown in FIG. 41D, the spring 936 is biased in a direction of the suction pipe 913 so that the pinching member 936 is brought into contact with the suction pipe 913 to pinch the suction pipe 913 closed. FIGS. 41A-C show the rocker 935 and the spring 936 being moved from the first position in FIG. 41A toward the second position, wherein in FIGS. 41B and 41C, the rocker 935 applies a force to the spring 936 to bias the spring 936 toward the suction pipe 913. The rocker pinch valve 935 may be any suitable rocker valve, such as an ON-OFF rocker pinch valve manufactured by Z-man corporation.

FIGS. 42A-42D show other views of the flow control assembly 930 of FIGS. 41A-41D. FIGS. 42A and 42C show a portion of the suction tube body 901 viewed from the outside with the rocker pinch valve 935 visible from the outside. In FIG. 42A, the rocker pinch valve 935 is in the first position (ON position) that allows suction, and in FIG. 42C, the rocker pinch valve 935 is in the second position (OFF position) that pinches the suction tube closed. FIG. 42B shows a more detailed view of the rocker pinch valve 935 together with the spring 936, including the pinching member 936a, being biased away from the suction tube (not shown), corresponding to the view of FIG. 42A. FIG. 42D shows a more detailed view of the rocker pinch valve 935 together with the spring 936 being biased toward the suction tube so as to pinch the suction tube closed, corresponding to the view of FIG. 42C. As shown in FIGS. 42B and 42D, the spring 936 is coupled to the rocker pinch valve 935 by passing the spring 936 between two holding projections on the surface of the rocker pinch valve 935. This engagement between the rocker pinch valve 935 and the spring 936 is exemplary and any other suitable coupling mechanisms may be used.

FIGS. 43A and 43B show another flow control mechanism 1030 which includes a push-through button 1035 for controlling the ON-OFF suction through the suction tube. In FIG. 43A, the push-through button 1035 is pushed up so that the suction flow through the suction tube is allowed (ON position), while in FIG. 43B, the push-through button 1035 is pushed down in order to turn off the suction through the suction tube (OFF position). It is contemplated that in other embodiments, the ON and OFF positions may be reversed. Inside the body 1001 of the suction device, the push-through button 1035 is connected to a valve or a barrier which is moved to block the suction through the suction tube when the button is moved to the OFF position, and moved out of the flow path when the button is in the ON position. The push-through button 1035 may be coupled with a bistable inversion mechanism to decrease throw required for switching between the ON and OFF positions.

FIGS. 44A and 44B show another flow control mechanism 1130 in which the suction is controlled using a pen click button 1135 for switching between the ON and OFF positions, with the pen click button being connected to a valve or a barrier which is moved to block the suction through the suction tube when the button is in the OFF position and moved away from the flow path to allow suction in the ON position. In addition, the button may be coupled with a mechanism to decrease throw. In FIG. 44A, the pen click button 1135 is in the OFF position, in which the suction is turned off, and in FIG. 44B, the pen click button 1135 is in the ON position, in which suction is turned on. However, these positions may be reversed in other embodiments.

FIGS. 45A-45E show a suction device 1200 with another illustrative flow control assembly 1230 for pinching the suction tube 1213 that uses a pivot cam follower mechanism. As shown, the flow control assembly 1230 includes a cam 1235 which has a predetermined profile designed to engage with a pivoting follower 1236 so as to cause the follower 1236 to pivot between a first position (ON position) away from the suction tube 1213 and a second position (OFF position) in which the follower 1236 pinches the suction tube 1213 closed. In the illustrative embodiment of FIGS. 45A-45E, the cam 1235 includes a controller projection 1235a thereon that projects from the body 1201 of the suction device 1200 so that the user can move the controller projection 1235a to rotate the cam 1235 between the ON and OFF positions.

As shown in FIGS. 45A and 45B, the cam 1235 and follower 1236 are at the ON position so that the follower 1236 abuts a recessed surface of the cam 1235 with a smaller radius and extends substantially along the suction tube 1213 without pinching the tube 1213. In FIGS. 45C and 45D, the cam 1235 is rotated to the OFF position by moving the controller projection 1235a in a direction of a proximal end of the suction device 1200. As the cam 1235 is rotated toward the OFF position, the radius of the cam 1235 at the point of contact with the follower 1236 increases pushing the follower 1236 toward the suction tube 1213 so as to pinch the suction tube 1213. As shown in FIG. 45D, the cam 1235 pivots and/or rotates between the ON and OFF positions around a first pivot point 1235b, while the follower 1236 pivots between the ON and OFF positions around a second pivot point 1236a. When the cam 1235 is rotated, friction between the faces of the cam 1235 and the follower 1236 holds the cam 1235 in place at all positions so that continuous flow adjustment can be achieved.

In some embodiments, a biasing member 1237, such as a spring, may be added between the cam 1235 and the body 1201 of the suction device, as shown in FIG. 45E. The spring 1237 biases against the sidewall of the cam 1235 in a direction substantially perpendicular to the rotation of the cam 1235. The spring 1237 adds friction to the face of the cam 1235 to lock it in place and to prevent it from rotating back to the open position.

Figures 47A, 47B:
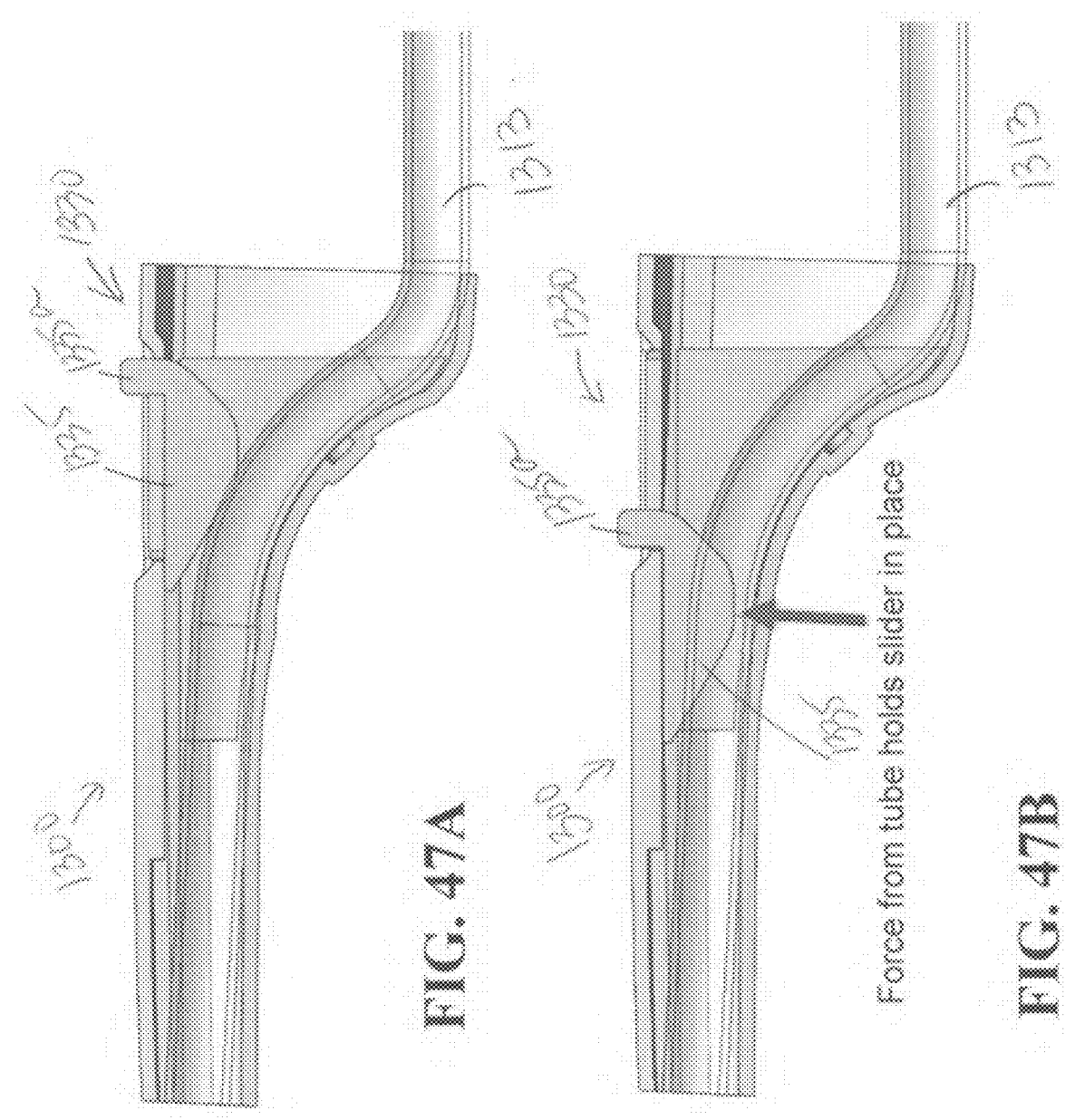

FIGS. 47A-B show a portion of a suction device 1300 with another flow control assembly 1330 which uses a wedge slider 1335 that is configured to pinch the suction tube 1313 closed in one position (OFF position) and to open the suction tube 1313 in another position (ON position). As shown, the slider 1335 has a wedge shape and an operating projection 1335a extending therefrom or connected thereto which can be operated by a user to slide the slider 1335 between the ON and OFF positions. In FIG. 47A, the wedge slider 1335 is in the ON position so that the wedge portion of the slider 1335 does not interfere with the suction tube 1313 and does not pinch the suction tube 1313. In FIG. 47B, the wedge slider 1335 is in the OFF position so that the wedge portion of the slider 1335 pinches the suction tube 1313 closed to block the flow of air therethrough.

FIGS. 48A-48B show a suction device 1400 with a flow control assembly 1430 that is configured to pinch the suction tube 1413 from the side rather than from the top. In the exemplary embodiment of FIGS. 48A-48B, the flow control assembly 1430 includes a cam wheel 1435 that has substantially flat side surfaces and a pinching projection 1436 on one side surface that abuts the suction tube 1413. The cam wheel 1435 also has an operating projection 1435a that can be operated by a user to move the cam wheel from an ON position, as shown in FIGS. 48A-48B, to an OFF position. In the ON position of the cam wheel 1435, the pinching projection 1436 does not abut or engage with the suction tube 1413 so that suction can be provided through the suction tube 1413. In the OFF position of the cam wheel, the pinching projection 1436 is moved to abut the suction tube 1413 and to pinch the suction tube 1413 closed so as to block suction through the suction tube 1413. In this embodiment, the direction of the spring return force from the suction tube is changed so that it is not actively creating a moment around the axis of the cam wheel 1435.

Figure 49C:
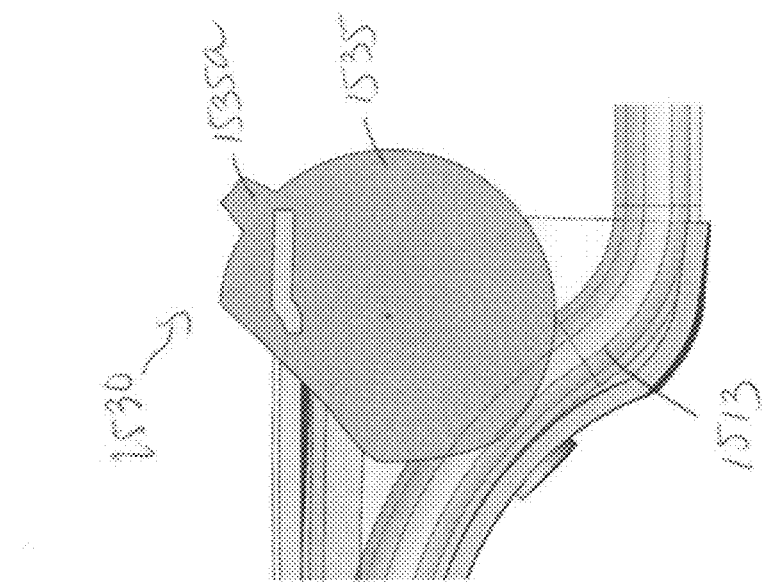
Figure 49B:
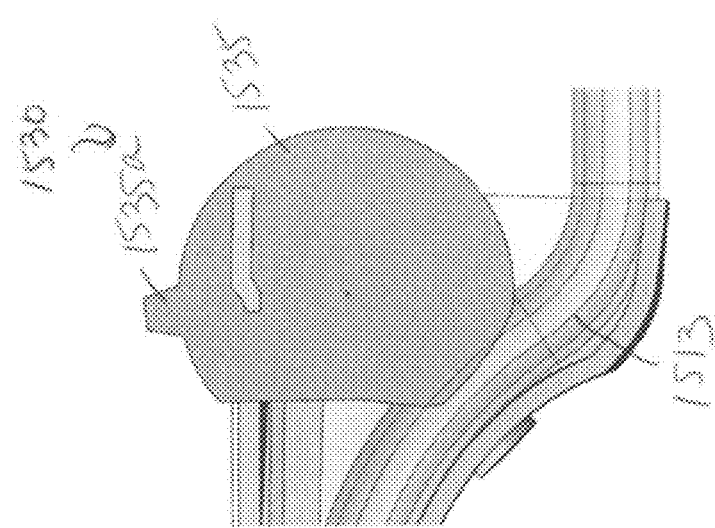
Figure 49A:
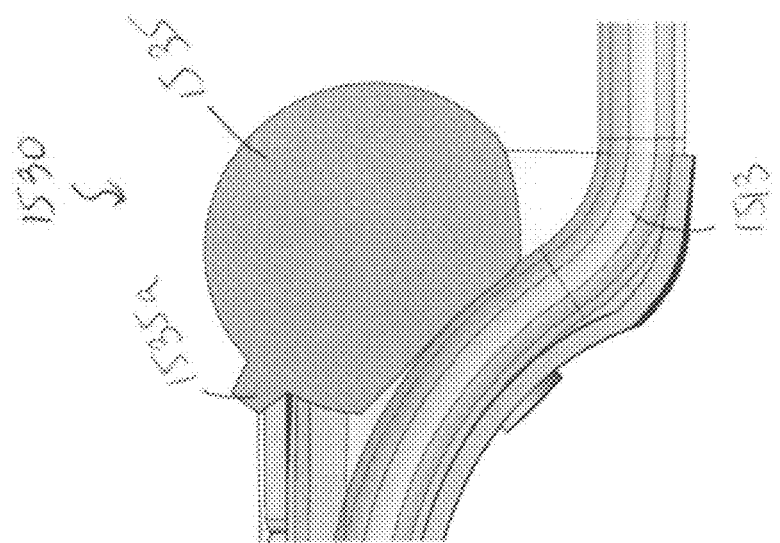

FIGS. 49A-49C show another illustrative embodiment of a flow control assembly 1530 that uses a cam wheel 1535 that directly interacts with the suction tube 1513 so as to pinch the suction tube 1513 closed in an OFF position, as shown in FIG. 49C. The cam wheel 1535 in this embodiment has a cam profile so that in an ON position, as shown in FIG. 49A, the cam wheel 1535 abuts the suction tube, or is adjacent to the suction tube, at a location where the radius of the cam wheel 1535 is the smallest so that the cam wheel does not pinch the suction tube 1513. As shown in FIG. 49B, when an operating projection 1535a on the cam wheel 1535 is moved from the ON position toward the OFF position, the radius of the cam wheel 1535 at a point of abutment with the suction tube 1513 increases to partially pinch the suction tube 1513 until the cam wheel 1535 is rotated to the OFF position in which the cam wheel 1535 pinches the suction tube 1513 closed.

FIGS. 50A and 50B show an illustrative flow control assembly 1630 that uses a rack and pinion mechanism. The flow control assembly 1630 of this embodiment includes a slider 1635 with an operating member 1635a on one side for operation by a user and rack (or linear gear) 1635b on another side configured to engage with a pinion (circular gear) 1636. The pinion 1636 has a cam 1637 attached thereto, which rotates together with the pinion 1636 as the rack 1635b slides with the slider 1635. The cam 1637 interacts with a follower 1638 which is moved between a first position (ON position) shown in FIG. 50A and a second position (OFF position) shown in FIG. 50B as the cam 1637 rotates with the pinion 1636. The geometry or profile of the cam 1637 causes the follower 1638 to move toward the suction tube 1613 as the slider 1635 moves from the ON position to the OFF position. In the present illustrative embodiment, the length of the slider is around 15 mm and the active circumference of the pinion 1636 is 335 degrees. The shape of the cam and follower is not limited to those shown in FIGS. 50A and 50B and may be adjusted based on the size and operating force requirements of the flow control assembly.

Figures 51A, 51B:
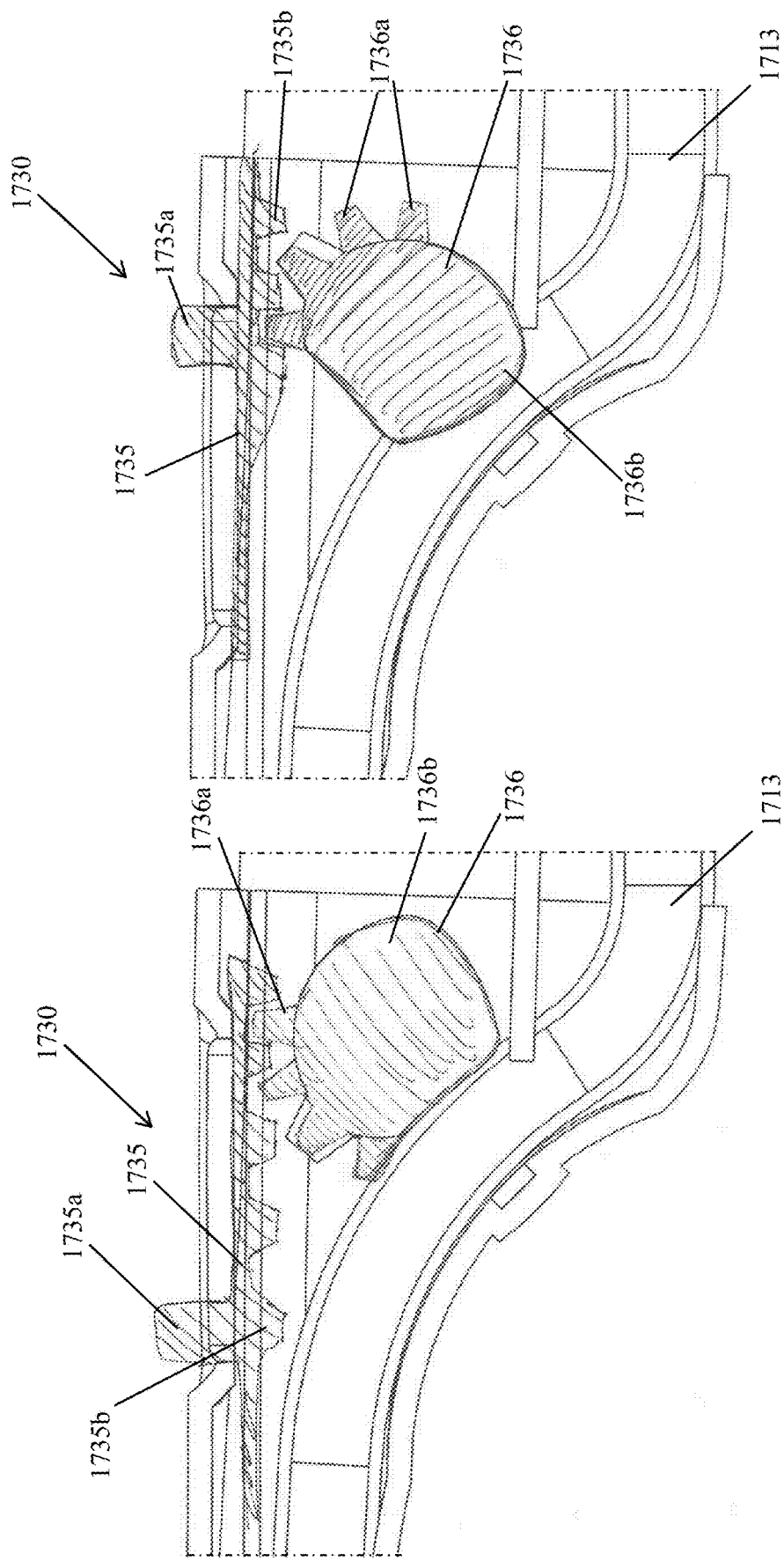

FIGS. 51A-51B show another illustrative flow control assembly 1730 that uses a rack and pinion mechanism. In this embodiment, the flow control assembly 1730 includes a slider 1735 with an operating member 1735a and a rack 1735b thereon, and a pinion cam 1736 which includes a plurality of teeth 1736a around a portion of its circumference and a cam surface 1736b that interacts with the suction tube 1731. The slider 1735 is configured to move between a first position (ON position) shown in FIG. 51A in which the cam surface 1736b of the pinion cam 1736 does not pinch the suction tube 1713, and a second position (OFF position) shown in FIG. 51B in which the cam surface 1736b of the pinion cam 1736 pinches the suction tube 1713 closed. The geometry of the pinion cam 1736 is configured to gradually pinch the suction tube 1713 as the slider 1735 moves between the first and second positions.

Figure 52A:
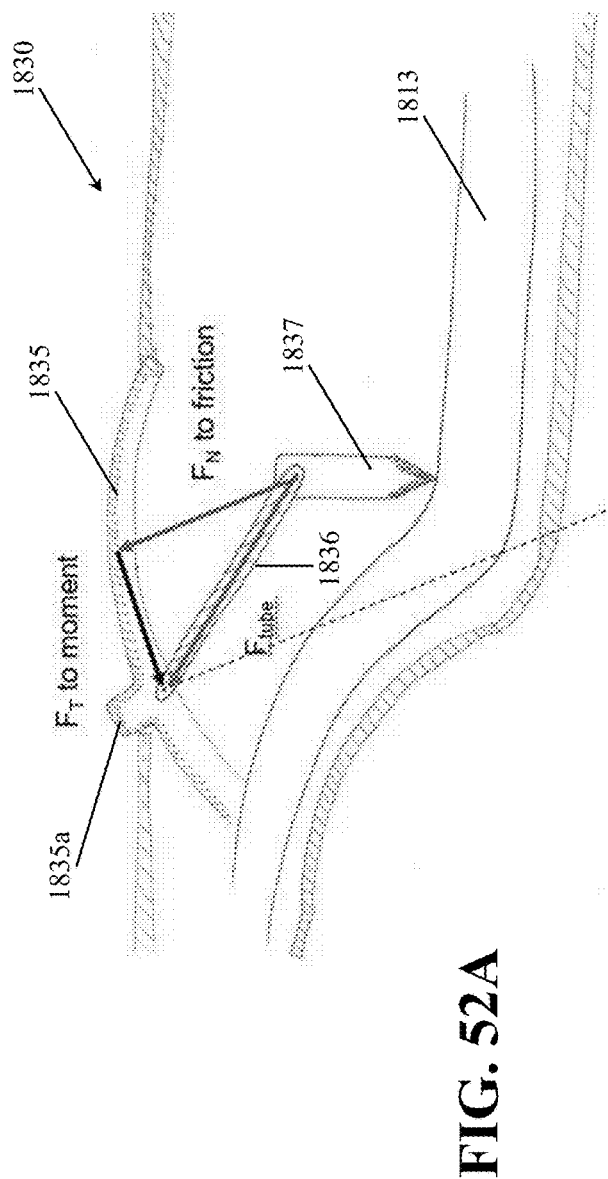
Figure 52B:
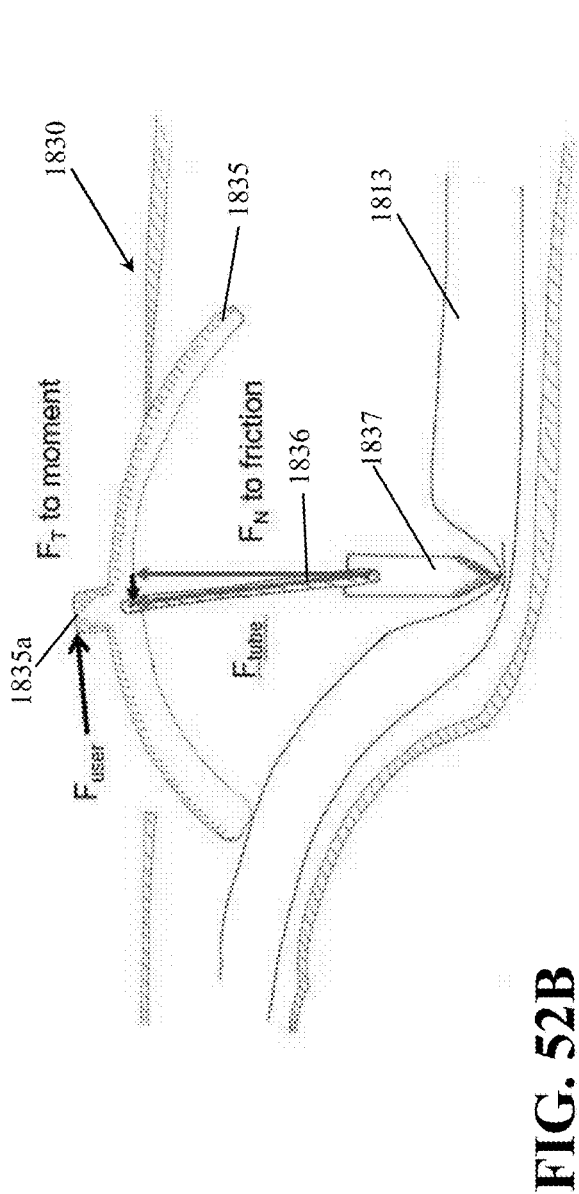

FIGS. 52A-52B show a further embodiment of a flow control assembly 1830 which includes an arcuate slider 1835, a first arm 1836 hingedly connected to the arcuate slider 1835, and a pinching arm 1837 hingedly connected to the first arm 1836. The arcuate slider 1835 includes an operating projection 1835a which can be operated by a user to move the slider 1835 from an ON position shown in FIG. 52A to an OFF position shown in FIG. 52B. When the arcuate slider 1835 is in the ON position, the first arm 1836 is positioned at an angle with respect to the pinching arm 1837 such that the pinching arm 1837 is retreated from the suction tube 1813 and does not pinch the suction tube 1813. When the slider 1835 is moved toward the OFF position, the first arm 1836 is rotated relative to the pinching arm 1837 and applies a force on the pinching arm 1837 in a direction of the suction tube 1813 so that the pinching arm 1837 moves from a first position (ON position) in a direction toward the suction tube 1813 to a second position (OFF position) so as to pinch the suction tube 1813 closed. When the slider 1835 is in the OFF position, the return force of the suction tube 1813 trying to open up does not create a momentum to push the arc of the slider back to the ON position. That is, the flow control mechanism of this invention is self-locking. In some embodiments, a spring or another biasing member may be added to the flow control assembly 1830 to provide friction relief to allow the user to more easily move the operating projection 1835a between the ON and OFF positions.

The above described flow control assemblies can be used with the suction device of the present invention so as to provide suction control during use. The embodiments of the flow control assemblies described above are provided within the neck portion of the body of the suction device. However, in other embodiments, the flow control assembly may be provided in other portions of the body of the suction device, depending on the space available within the body. Moreover, the flow control assemblies of described above may be used in other medical devices that provide suction or fluids, including surgical retractors, catheters, electrocautery devices, etc. Moreover, the flow control assembly configurations are not limited to those specifically shown and described above and may be customized or modified for the specific geometry and requirements of the device in which it is used.

Although certain embodiments have been described in considerable detail herein, other embodiments, variations, and modifications that fall within the spirit and scope of the invention will be apparent to those skilled in the art. Therefore, the scope of any claims allowed for this application should not be limited to any specific embodiments or to any non-claimed details of the embodiments described herein.

We claim:

1. An illuminated suction device comprising:
   an outer housing having a suction tube extending therefrom; and
   an illumination assembly comprising at least one direct light source oriented to emit light radially away from a central axis of the suction device and at least one reflector configured to reflect light from the at least one direct light source toward a target area external to the outer housing without requiring the suction tube to provide illumination to the target area.

2. The illuminated suction device in accordance with claim 1, wherein the illumination assembly does not include a waveguide.

3. The illuminated suction device in accordance with claim 1, wherein the suction tube includes a proximal end and a distal end, said suction tube extending from the outer housing to the distal end, and wherein the target area is adjacent the distal end of the suction tube.

4. The illuminated suction device in accordance with claim 3, wherein the at least one reflector is a concave multi-faceted reflector and wherein the direct light source is positioned within a concavity of the at least one reflector.

5. The illuminated suction device in accordance with claim 3, wherein the illumination assembly further includes at least one lens for refracting light reflected from the at least one reflector toward the target area.

6. The illuminated suction device in accordance with claim 3, wherein the at least one direct light source includes a first direct light source oriented to emit light radially away from the central axis of the suction device in a first direction and a second direct light source oriented to emit light radially away from the central axis of the suction device in a second direction different from the first direction, and wherein the at least one reflector reflects light emitted from the first direct light source and light emitted from the second direct light source toward the same target area.

7. The illuminated suction device in accordance with claim 6, wherein the first direction is opposite to the second direction.

8. The illuminated suction device in accordance with claim 1, wherein the light source is one or more of: (a) protrudes through a cutout in a metallic heat sink; and (b) mounted on the metallic heat sink.

9. The illuminated suction device in accordance with claim 1, wherein the at least one direct light source is positioned so as to maintain an air gap between the suction tube and the at least one direct light source.

10. An illuminated suction device comprising:
    an outer housing having a suction tube extending therethrough; and
    an illumination assembly including a plurality of direct light sources and a built-in power source for supplying power to the plurality of direct light sources, said power source being housed within the outer housing,
    wherein the illumination assembly directs light toward a target area external to the suction tube without requiring the suction tube to provide illumination to the target area.

11. The illuminated suction device in accordance with claim 10, wherein each of the plurality of direct light sources is provided at a different location around the suction tube.

12. The illuminated suction device in accordance with claim 11, wherein the plurality of direct light sources include a first direct light source provided adjacent to one side of the suction tube and a second direct light source provided adjacent to another side of the suction tube.

13. The illuminated suction device in accordance with claim 10, wherein the illumination assembly further includes one or more optical elements, said optical elements including one or more of a reflector and a lens.

14. The illuminated suction device in accordance with claim 13, wherein each of the plurality of direct light sources emits light radially away from the suction tube and the one or more optical elements are configured to direct light emitted from the plurality of direct light sources toward the target area adjacent to a distal tip of the suction tube.

15. The illuminated suction device in accordance with claim 14, wherein the one or more optical elements include at least one concave reflector configured to reflect light emitted from the at least one direct light source toward the target area.

16. The illuminated suction device in accordance with claim 10, wherein the outer housing includes a proximal end and a distal end, the suction tube extends from the proximal end of the outer housing and beyond the distal end of the outer housing, and wherein the built-in power source is provided adjacent the proximal end of the outer housing.

17. The illuminated suction device in accordance with claim 10, further comprising a heat sinking assembly for conducting heat generated by the plurality of direct light sources, the heat sinking assembly comprising one or more heat sinking members thermally connected to the direct light sources.

18. The illuminated suction device in accordance with claim 17, wherein the heat sinking assembly comprises a plurality of heat sinking members, each said heat sinking member being thermally connected with a direct light source and each said heat sinking member comprising a metallic plate having a high thermal conductivity.

19. An illuminated suction device comprising:
    an outer housing having a suction tube extending therefrom; and
    an illumination assembly including one or more direct light sources and one or more optical elements, said illumination assembly being configured to provide substantially shadowless, substantially uniform light to a target area adjacent a distal end of the suction tube without requiring the suction tube to provide illumination to the target area.

20. The illuminated suction device in accordance with claim 19, wherein the one or more optical elements include one or more of a reflector and a lens.

21. The illuminated suction device in accordance with claim 20, wherein the illumination assembly includes a plurality of direct light sources and the one or more optical elements includes at least one concave reflector for reflecting light emitted from the plurality of direct light sources toward the target area, said plurality of direct light sources being positioned within a concavity of the at least one concave reflector.

22. The illuminated suction device of claim 21, wherein each of the direct light sources is oriented so as to emit light radially in a direction away from a central axis of the suction tube.

23. The illuminated suction device of claim 22, wherein the plurality of direct light sources include a first light source positioned adjacent a first side of the suction tube and a second light source positioned adjacent a second side of the suction tube opposite of the first side.

24. The illuminated suction device of claim 22, wherein the one or more optical elements further includes at least one lens for refracting light reflected from the at least one concave reflector.

25. An illuminated medical device comprising:
an outer housing;
an illumination assembly at least partially enclosed by the outer housing and including a plurality of direct light sources for providing illumination from the outer housing; and
a heat sinking assembly comprising a plurality of heat sinking members, each heat sinking member being thermally coupled with a corresponding direct light source,
wherein each heat sinking member extends along a majority portion of a length of the outer housing.

26. The illuminated medical device in accordance with claim 25, wherein each heat sinking member comprises a metallic plate member including one or more through openings, each of said through openings being configured to accommodate one of the direct light sources.

27. The illuminated medical device in accordance with claim 26, wherein the plurality of direct light sources are mounted on one or more flexible circuits and wherein each flexible circuit is thermally coupled to a corresponding heat sinking member using adhesive thermal tape.

28. The illuminated medical device in accordance with claim 26, wherein a thickness of the metallic plate member is not greater than a thickness of the corresponding direct light source and the through opening in the metallic plate member self-aligns the corresponding direct light source.

29. The illuminated medical device in accordance with claim 25, wherein the medical device is a suction device including a suction tube extending from the outer housing.

30. The illuminated medical device in accordance with claim 29, wherein the suction tube extends within the outer housing and along at least a substantial portion of a length of the outer housing and wherein the outer housing includes projections therein for maintaining an air gap between the suction tube and the plurality of heat sinking members.

* * * * *